(12) United States Patent
Ferber

(10) Patent No.: US 9,481,894 B2
(45) Date of Patent: Nov. 1, 2016

(54) METHODS OF INDUCING REGULATED PANCREATIC HORMONE PRODUCTION IN NON-PANCREATIC ISLET TISSUES

(71) Applicant: Sarah Ferber, Tel Aviv (IL)

(72) Inventor: Sarah Ferber, Tel Aviv (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 0 days.

(21) Appl. No.: 14/330,965

(22) Filed: Jul. 14, 2014

(65) Prior Publication Data
US 2015/0017727 A1  Jan. 15, 2015

Related U.S. Application Data

(63) Continuation of application No. 10/843,801, filed on May 12, 2004, now Pat. No. 8,778,899.

(51) Int. Cl.
| | |
|---|---|
| *C12N 5/00* | (2006.01) |
| *C12N 15/85* | (2006.01) |
| *A61K 38/17* | (2006.01) |
| *A61K 48/00* | (2006.01) |
| *C12N 15/86* | (2006.01) |

(52) U.S. Cl.
CPC ........... *C12N 15/85* (2013.01); *A61K 38/1709* (2013.01); *A61K 48/00* (2013.01); *C12N 15/86* (2013.01); *C12N 2710/10343* (2013.01); *C12N 2830/008* (2013.01); *C12N 2830/85* (2013.01)

(58) Field of Classification Search
CPC ..................................................... C12N 15/85
USPC ........................................................ 435/377
See application file for complete search history.

(56) References Cited

U.S. PATENT DOCUMENTS

| | | | |
|---|---|---|---|
| 4,522,811 | A | 6/1985 | Eppstein et al. |
| 4,737,323 | A | 4/1988 | Martin et al. |
| 4,837,028 | A | 6/1989 | Allen |
| 4,837,316 | A | 6/1989 | Sekine et al. |
| 4,980,286 | A | 12/1990 | Morgan et al. |
| 5,082,670 | A | 1/1992 | Gage et al. |
| 5,328,470 | A | 7/1994 | Nabel et al. |
| 5,424,286 | A | 6/1995 | Eng |
| 5,703,055 | A | 12/1997 | Felgner et al. |
| 5,741,673 | A | 4/1998 | Montminy et al. |
| 5,849,989 | A | 12/1998 | Edlund |
| 5,942,435 | A * | 8/1999 | Wheeler ............... 435/325 |
| 6,242,666 | B1 | 6/2001 | Sarvetnick et al. |
| 6,716,824 | B1 | 4/2004 | Brunicardi |
| 2003/0219894 | A1 | 11/2003 | Susumu et al. |

FOREIGN PATENT DOCUMENTS

| | | |
|---|---|---|
| EP | 0 264 166 | 4/1988 |
| EP | 1 354 942 A1 | 10/2003 |
| WO | WO 94/08598 | 4/1994 |
| WO | WO 95/05463 | 2/1995 |
| WO | WO 97/20075 | 6/1997 |
| WO | WO 97/49728 | 12/1997 |
| WO | WO 00/72885 A2 | 12/2000 |
| WO | WO 03/033697 | 4/2003 |
| WO | WO 03/078636 | 9/2003 |
| WO | WO 2004/098646 | 11/2004 |

OTHER PUBLICATIONS

Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Ferber et al. (2000, Nature Med., vol. 6(5), pp. 568-572).*
Wang et al. (2001, JBC, vol. 276(27), pp. 25279-25286).*
Yang et al. (2002, PNAS, vol. 99(12), pp. 8078-8083).*
Okitsu et al. (Jan. 2004, Diabetes, vol. 53, pp. 105-112).*
Thowfeequ, S. et al., "Transdifferentiation in Developmental Biology, Disease, and in Therapy", *Developmental Dynamics*, 2007, pp. 3208-3217, vol. 236, Wiley-Liss, Inc.
Ahlgren et al., "The morphogenesis of the pancreatic mesenchyme is uncoupled from that of the pancreatic epithelium in IPF1/PDX1-deficient mice", *Oev.* 122:1409-1416 (1996).
Amann et al., "Tightly regulated tac promoter vectors useful for the expression of unfused and fused proteins in *Escherichia coli*", *Gene*, 69:301-315 (1988).
Anderson, "Human gene therapy", *Nature*, 392:25-30 (1998).
Baldari et al., "A novel leader peptide which allows efficient secretion of a fragment of human interleukin 1β in *Saccharomyces cerevisiae*", *EMBO J.*, 6(1):229-234 (1987).
Banerji et al., "A lympocyte-specific cellular enhancer is located downstream of the joining region in immunoglobulin heavy chain genes", *Cell*, 33:729-740 (1983).
Bonner-Weir et al., "New sourves of pancreatic β-cells", *Nature Biotech.*, 23(7):857-861 (2005).
Byrne et al., "Multiplex gene regulation: a two-tiered approach to transgene regulation in transgenic mice", *Proc. Nat/. Acad. Sci. USA*, 86:5473-5477 (1989).
Calame et al., "Transcriptional controlling elements in the immunoglobulin and T cell receptor loci", *Adv. Immunol.*,43:235-275 (1988).
Camper et al., "Postnatal repression of the a-fetoprotein gene is enhancer independent", *Gene Dev.*, 3:537-546 (1989).
Campos et al., 1994, *Endocrinology*, 134: 2156-2164
Caplan, AI. "Adult Mesenchymal Stem Cells for Tissue Engineering Versus Regenerative Medicine." *Journal of Cellular Physiology*, 213:341-347 (2007).
Chen et al., "Gene therapy for brain tumors: regression of experimental gliomas by adenovirus-mediated gene transfer in vivo", *Proc. Nat/. Acad. Sci. U.S.A.*, 91:3054-3057 (1994).
Dunbar et al., 1999, *Biochem J.*, 344: 713-721.
Edlund et al., "Cell-specific expression of the rat insulin gene: evidence for role of two distinct 5' flanking elements", *Science*. 230:912-916 (1985).

(Continued)

*Primary Examiner* — Anoop Singh
*Assistant Examiner* — David A Montanari
(74) *Attorney, Agent, or Firm* — Mark S. Cohen; Pearl Cohen Zedek Later Baratz LLP

(57) ABSTRACT

Disclosed are methods and pharmaceutical compositions for inducing pancreatic hormone production.

9 Claims, 38 Drawing Sheets

(56) References Cited

OTHER PUBLICATIONS

Ferber et al., "Pancreatic and duodenal homeobox gene 1 induces expression of insulin genes in liver and ameliorates streptozotocin-induced hyperglycemia," *Nature Med,*, 6:568-572 (2000).
GenBank Accession No. AAA88820.1, Feb. 20, 1996
GenBank Accession No. AAC41260.1, Mar. 6, 1998.
GenBank Accession No. AAA18355.1, May 25, 1994.
GenBank Accession No. AF036325.1 Mar. 6, 1998.
GenBank Accession No. U35632.1, Feb. 21, 1996.
Goldspiel et al., "Human gene therapy", *Clin. Pharm.*, 12:488-505 (1993).
Goke et al., 1993, *The Journal of Biological Chemistry*, 268: 19650-19655.
Gottesman, S., "Minimizing proteolysis in *Escherichia coliu*: genetic solutions", *Meth. Enzimol.*, 185:119-129 (1990).
Grosset al., "Increased suceptibility of islets from diabetes-prone psammomys obesus to the deleterious effects of chronic glucose exposure", *Endocrinology*, 137(12):5610-5615 (1996).
Hamaguchi et al. "Comparison of Cytokine Effects on Mouse Pancreatic Alpha-Cell and Beta-Cell Lines." *Diabetes*. 39.4(1990):415-425.
Horb et al., *Curr. Biol.*, 13(2):105-115 (2003).
Howard III, et al., "Intracerebral drug delivery in rats with lesion-induced memory deficits", *J. Neurosurg.*, 71;105-112 (1989).
Hsu et al. "Molecular Cloning of a Novel Splice Variant of the Alpha Subunit of the Mammalian Go Protein." *J. Biol. Chem.* 265.19(1990):11220-11226.
International Search Report for PCT/IB2004/001973, mailed Oct. 19, 2004.
Joliot et al., "Antennapedia homeobox peptide regulates neural morphogenesis", *Proc. Nat/. Acad. Sci. USA*, 88:1864-1868 (1991).
Jonsson et al., "Insulin-Promoter-Factor 1 is Required for Pancreas Development in Mice, " *Nature*, 371:606-609 (1994).
Kahn et al., 1999, Diabetes, 48: 241-253.
Kahn, A., "Converting hepatocytes to 13-cells-a new approach for diabetes?" *Nature Med.*, 6:505-506 (2000).
Kajimoto et al., "Suppression of Transcription Factor PDX-1/IPF1/STF-1 Causes No Decrease in Insulin mRNA in MIN6 Cells", *J. Clin. Invest.*, 100:1840-1846 (1997).
Kaufman et al., "Translational efficiency of polycistronic mRNAs and their utilization to express heterologous genes in mammalia cells", *EMBO J.* 6(1):17-193 (1987).
Kessel et al., "Murine developmental control gene", *Science*, 249:374-379 (1990).
Kojima, H. et al, "Combined expression of pancreatic duodenal homeobox 1 and islet factor 1 induces immature enterocytes to produce insulin." *Diabetes*, 51(5): 1398-408, (2002).
Kojima et al., "NeuroD-betacullulin gene therapy induces islet neogenesis in the liver and reverses diabetes in mice", *Nat. Med.*, 9(5):596-603 (2003).
Koller et al., "Inactivating the 132-microglobulin locus in mouse embryonic stem cells by homologous recombinant", *Proc. Nat/. Acad. Sci. USA*, 86:8932-8935 (1989).
Koya et al., "Reversal of Streptozotocin-Induced Diabetes in Mice by Cellular Transduction With Recombinant Pancreatice Transcription Factor Pancreatic Duodenal Homeobox-1. A Novel Protein Transduction Domain-Based-Therapy", *Diabetes*, 57:757-769 (2008).
Kurjan et al., "Structure of a yeast phermone gene (MFa): a putative a-factor precursor contains four tandem copies of mature a-factor", *Cell*, 30:933-943 (1982).
Marshak et al., "Purification the B-cell glucose-sensitive factor that transactivates in normal and transformed islet cells", *Proc. Nat'l, Acad. Sci., U.S.A.*, 93:15057-15062 (1996).
Milewski et al., "Conversion of PDX-1 Structure, Function, and Expression in Zebrafish", *Endocinol.*, 139:1440-1449 (1998).
Miller et al., "IDX-1: a new homeodomain transcription factor expressed in rat pancreatic islets and duodenum that transactivates the somatostation gene," *EMBO J.*, 13:1145-1156 (1994).

Mitanchez, D. et al. Regulated expression of mature human insulin in the liver of transgenic mice. *FEBS Letters*, vol. 421, No. 3, pp. 285-289. 1998.
Muzzin et al., "Hepatic insulin gene expression as treatment for type 1 diabetes mellitus in rats," *Mol. Endocrinol.*, 11:833-387 (1997).
Novolin R [online], 2005-2010 [retreived on Apr. 4, 2010]. Retreived from the Internet:<URL:http://www.drugs.com/pro/novolin-r.html>, pp. 1-15.
Li et al., "In vitro transdifferentiation hepatoma cells into functional pancreatic cells", *Mech. Dev.*, 122:835-847 (2005).
Loeffler et al., "Gene transfer into primary and established mammalian cell lines with lipopolyamine-coated DNA", *Meth. Enzimol.*, 217:599-618 (1993).
Luckow et al., "High level expression of nonfused foreign genes with Autographa californica nuclear polyhedrosis virus expression vectors", *Virology*, 170:31-39 (1989).
Nakajima-Nagata et al., "Pdx-1 enables insulin secretion by regulating synaptotagmin 1 gene expression", *Biochem. Biophys. Res. Comm.*, 318:631-635 (2004).
Nir et al., "How to make pancreatic β cells-prospects for cell therapyin diabetes", *Curr. Opin. Biotech.*, 16:524-529 (2005).
Noguchi et al., "Mechanisim of PDX-1 protein transduction", *Biochem. Biophys. Res. Comm.*, 332:68-74 (2005).
Noguchi et al., "PDX-1 protein containing its own antennapedia-like protein transdujction domain can transducer pancreatic duct islet cells", *Diabetes*, 52:1732-1737 (2003).
Offield et al., "PDX-1 is required for pancreatic outgrowth and differentiaon of the rostral duodenum", *Development*, 122:983-995 (1996).
Ohneda, K et al., "The Homeodomain of PDX-1 Mediates Multiple Protein-Protein Interactions in the Formation of a Transcriptional Activation Complex on the Insulin Promoter." *Molecular and Cellular Biology*, vol. 20, pp. 900-911. 2000.
Otonkoski et al., "Stem cells in the treatment of diabetes", *Ann. Med.*, 37:513-520 (2005).
Ozcan et al., "Functional expression and analysis of the pancreatic transcription factor PDX-1 in yeast", *Biochem. Biophys. Res. Comm.*, 295:724-729 (2002).
Peers et al., Biosis Online, Accession No.: PREV199598090886 (1994).
Pinkert et al., "An albumin enhancer located 10 kb upstream functions along with its promoter to direct efficient, liver-specific expression in transgenic mice", *Genes Dev.*, 1:268-276 (1987).
Queen et al., "Immunoglobin gene transcription is activated by downstrea, sequence elements", *Cell*, 33:741-748 (1983).
Rheinwald et al., "Epidermal growth factor and the multiplication of cultured human epidermal keratinocites", *Nature*, 265:421-424 (1977).
Ross, M.F., "Protein power: Researchers trigger insulin production in diabetic mice", U FLA NEWS, Yang Press Release, http://news.ufl.edu/2008/01/08/pdx1/, 2 pages, Jan. 8, 2008.
Salomaa et al., 1995, *Circulation*, 1432-1443.
Sakurai et al., 2007, *Journal of Controlled Release*, 117: 430-437.
Saudek et al., "A preliminary trial of the programmable implantable medication system for insulin delivery", *N. Engl. J. Med.*, 321(9);574-579 (1989).
Schmidt et al., 1990, *Molecular and Cellular Biology*, 10:4406-4411.
Schultz et al., "Expression and secretion in yeast of a 400-kDa envelope glyocprotein derived from Espstein-Barr virus", *Gene*, 54:113-123 (1987).
Seed, B., "An LFA-3 eDNA encodes a phospholid-linked membrane homologous to its receptor C02", *Nature*, 329:840-842 (1987).
Seijffers et al., "Increase in PDX-1 levels suprpresses insulin gene expression in RIN 1046-38 Cells", *Endocrinology*, 140(7):3311-3317 (1999).
Serup et al., 1996, *PNAS*, USA, 93:9015-9020.
Shamblott et al., "Cell therapies for type 1 diabetes mellitus", *Exp. Opin.*, 4(3)269-277 (2004).
Smith et al., "Production of human beta interferon in insect cells infected with a baculovirus expression vector", *Mol. Cell. Biol.*, 3(12):2156-2165(1983).

(56) References Cited

OTHER PUBLICATIONS

Smith et al., "Single-step purification of polpeptides expressed in *Escherichia coli*, as fusion with glutathione S-transferase", *Gene*, 67:31-40 (1988).

Stemple et al., "Isolation of a stem cell for nerons and glia from the mammalian neural crest", *Cell*, 71:973-985 (1992).

Stoffel et al., "Localization of human homeodomain transcription factor insulin promoter factor 1 (IPF1) to chromosome band 13q12. 1" ,*Genomics*, 28(1):125-126 (1995)

Studier et al., in *Gene Ecpression Technology: Methods in Enzymology*, 185, Academic Press, San Diego, CA, pp. 60-89 (1990).

Trehin et al., "Chances and pitfalls of cell penetrating peptides for cellular drug delivery", *Eur. J. Pharm. Biopharm.*, 58:209-223 (2004).

Tur-Haspa et al., 1986, *Molecular and Cellular Biology*, 6: 716-718.

Verma et al., "Gene therapy—promises, problems and prospects", *Nature*, 389:239-242 (1997).

Vieau et al., "Mouse Insulinoma Beta TC3 Cells Express Prodynorphin Messenger Ribonucleic Acid and Derived Peptides: A Unique Cellular Model for the Study of Prodynorphin Biosynthesis and Processing." *Endocrinol.* 136.3(1995):1187-1196.

Wada et al., "Codon usage tabulated from the GenBank genetic sequence data", *Nucl. Acids. Res.*, 20(suppl.):2111-2118 (1992).

Wang et al., 1999, *Endocrinology*, 140: 4904-4097.

Weintraub et al., "Anti-sense RNA as a molecular tool for genetic analysis", *Reviews—Trends in Genetics*, 1(1):22-25 (1985).

Winoto et al., "A novel, inducible and T cell-specific enhancer located at the 3' end of the T cell receptor a locus", *EMBO J.*, 8(3):729-733 (1989).

Wu et al., "Receptor-mediated in Vitro gene transformation by a soluble DNA carrier system", *J. Biol. Chem.*, 262(10):4429-4432 (1987).

Yamada et al., "In Vitro Transdifferentiation of Mature Hepatocytes into Insulin-Producing Cells", *End. J.*, 53(6):789-795 (2006).

Yang et al. *PNAS*, 99(12):8078-8083 (2002).

Office Action for U.S. Appl. No. 10/852,994 mailed on Feb. 19, 2009.

Office Action for U.S. Appl. No. 10/852,994 mailed on May 14, 2008.

Office Action for U.S. Appl. No. 10/852,994 mailed on Sep. 7, 2007.

Watada et al.: "Involvement of the Homeodomain-Containing Transcription Factor PDX-1 in Islet Amyloid Polypeptide Gene Transcription", 1996, Biochemical and Biophysical Research Communications, 229, pp. 746-751.

\* cited by examiner

MICROARRAY CHIP ANALYSIS: PDX-1 TREATED LIVER CELLS & CONTROL CELLS

262 GENES ANALYZED WERE UP-REGULATED BY ECTOPIC PDX-1 EXPRESSION

207 GENES ANALYZED ARE DOWN-REGULATED BY ECTOPIC PDX-1 EXPRESSION

PDX-1 INDUCES CHANGES IN THE EXPRESSION OF ABOUT 500 GENES WHEN ECTOPICALLY EXPRESSED IN LIVER CELLS, IN-VITRO

PDX-1 REPRESSES THE HEPATIC MASTER REGULATOR C/EBPβ GENE EXPRESSION
DNA MICROARRAY ANALYSIS
|  | Liver | Pancreas | Control Cells | Insulin Cells | PDX-1 Cells | Pancreas/ Liver | PDX-1 /Control |
|---|---|---|---|---|---|---|---|
| C/EBPβ | 2021 | 891 | 1700 | 1400 | 902 | -1.5 | -1.2 |
Fig. 30A
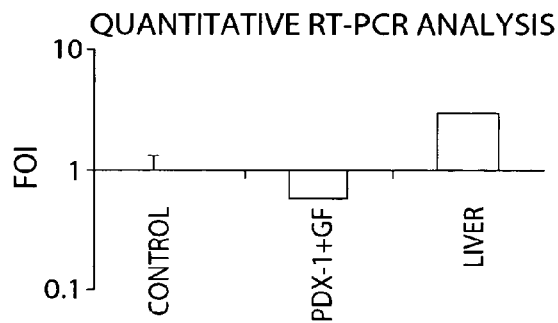
Fig. 30B
WESTERN BLOT ANALYSIS
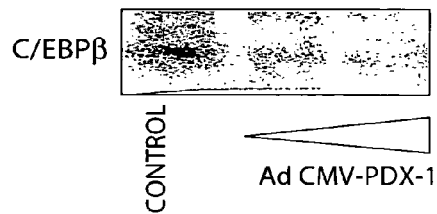
Fig. 30C

METHODS OF INDUCING REGULATED PANCREATIC HORMONE PRODUCTION IN NON-PANCREATIC ISLET TISSUES

RELATED APPLICATIONS

This application is a continuation of U.S. patent application Ser. No. 10/843,801, filed May 12, 2004 now U.S. Pat. No. 8,778,899. The content of this application is incorporated herein by reference in its entirety.

INCORPORATION-BY-REFERENCE OF SEQUENCE LISTING

The contents of the text file named "ORGS-701_C02US 322115-2025_ST25.txt", which was created on Sep. 26, 2014 and is 10 KB in size, are hereby incorporated by reference in their entireties.

FIELD OF THE INVENTION

This invention relates generally to methods of inducing a pancreatic endocrine phenotype and function including pancreatic hormone production in a non-endocrine tissue and in particular to methods and pharmaceutical compositions for treating endocrine related disorders.

BACKGROUND OF THE INVENTION

The endocrine pancreas consists primarily of islet cells that synthesize and secrete the peptide hormone glucagon, insulin, somatostatin and pancreatic polypeptide. Insulin gene expression is restricted to pancreatic islet β-cells of the mammalian pancreas through control mechanisms mediated in part by specific transcription factors. In other cells the insulin, other pancreatic hormones and specific peptidases genes are tranicriptionally silent. The homeodomain protein PDX-1 (Pancreatic and Duodenal Homeobox gene-1, also known as IDX-1, IPF-1, STF-1 or IUF-1) plays a central role in regulating pancreatic islet development and function. PDX-1 is either directly or indirectly involved in islet-cell-specific expression of various genes such as for example insulin, glucagon somatostatin, proinsulin convertase 1/3 (PC1/3), GLUT-2 and glucokinase. Additionally, PDX-1 mediates insulin gene transcription in response to glucose.

SUMMARY OF THE INVENTION

The invention is based in part on the discovery that ectopic expression of pancreatic and duodenal homobox gene 1 (PDX-1) in liver induces the expression of the silent pancreatic hormone genes and the processing machinery, which converts the prohormones into mature biologically active hormones.

The invention provides methods of inducing the expression of a pancreatic gene in a cell by introducing to the cell a PDX-1 inducer compound. The invention further provides a method of converting a non-pancreatic cell to a pancreatic cell, by contacting the non-pancreatic cell with a PDX-1 inducer compound. The non-pancreatic cell is contact with the PDX-1 inducer compound in an amount to induce the expression of endogenous PDX-1, an embryonic marker, insulin, glucogon, or somatostatin in repress the expression of C/EBPβ, albumin or ADH-1 in said non-pancreatic cell. An embryonic marker is for example, alpha-1 fetoprotein or Gata-4.

A PDX-1 inducer compound is any compound that induces the expression of endogenous PDX-1. A PDX-1 inducer compound is a nucleic acid, polypeptide or small molecule. Exemplary PDX-1 inducer compounds include, a nucleic acid encoding a pancreatic and duodenal homobox 1 (PDX-1) polypeptide, a neuroD polypeptide or a betacellulin polypeptide.

The nucleic acid is operably linked to a promoter such as for example, cytomegalovirus (CMV) promoter, a BOS promoter, a transthyretin promoter, a glucose 6-phosphatase promoter, an albumin intestinal fatty acid binding protein promoter, a thyroglobulin promoter, a surfactant A promoter, a surfactant c promoter or a phosphoglycerate kinase 1 promoter. The method of nucleic acid is present in a plasmid or a vector. The vector is a viral vector such as an adenovirus vector or a lentivirus vector. The adenovirus vector is for example a gutless recombinant adenovirus vector.

By "induces the expression" it is meant that expression of the gene is increased in the presence of the compound compared to the absence of the compound. to said cell a composition comprising a nucleic acid encoding a pancreatic and duodenal homobox 1 (PDX-1) polypeptide, in an amount sufficient to induce said gene expression in said cell. By "represses the expression" it is meant that expression of the gene is decreased in the presence of the compound compared to the absence of the compound.

A pancreatic gene includes for example a pancreatic transcription factor such as PDX-1, beta 2, ISL-2, NRx6.1, Ngn3.1, or NKx2.2, an endocrine gene such is SCG2, SGNE1, CHGN, PTPRN, AMPH, NBEA, NeuroD or folistatin or an exocrine gene such as serine protease inhibitor, Kazal type 1, Elastase, factor-p48, regenerating islet-derived 1 alpha.

The cell is provide in vivo, in vitro or ex vivo from a mammalian subject. The cell is a non-pancreatic cell. The cell is a differentiated cell. The cell is an ectodermal cell, endodermal cell, or mesodermal cell. For example the cell is a liver cell, a skin cell, or a bone marrow cell. Optionally, the cell is further contacted with a transfection agent or a composition containing nicotinamide, epidermal growth factor, activin A, hepatic growth factor, exendin, GLP-1 or betacellulin.

The invention provides methods of inducing pancreatic hormone, e.g., insulin, glucagon and somatostatin levels in a subject. In one aspect, the method includes administering to a subject in need thereof a compound which increases PDX expression or activity in an amount sufficient to induce pancreatic hormone production in the subject. In another aspect, the method includes providing a cell capable of expressing a pancreatic hormone, contacting the cell with a compound which increases PDX expression or activity and introducing the cell into a subject, thereby inducing pancreatic hormone production in the subject.

Also provided in the invention is a method of treating, alleviating a symptom of or delaying the onset of a pancreatic-related disorder such as diabetes, e.g., Type I or Type II in a subject. The method includes administering to a subject a therapeutically effective amount of a compound which increases PDX expression. For example the compound a nucleic acid encoding a pancreatic and duodenal homobox 1 (PDX-1) polypeptide. Symptoms of diabetes include hyperglycemia, elevated blood glucose (blood sugar), frequent urination excessive thirst, extreme hunger, unusual weight loss, increased fatigue, irritability, or, blurry vision. Diabetes is diagnosed for example by fasting plasma glucose test or random blood glucose test.

In another aspect the invention provides a method of inducing a pancreatic islet gene expression profile in a subject. The method includes administering to a subject in need thereof a compound which increases PDX expression or activity in an amount sufficient to induce pancreatic islet gene expression.

In yet a further aspect of the invention is a method inducing or enhancing a pancreatic islet cell phenotype in a cell. The method includes contacting a cell with compound which increases PDX expression or activity in an amount sufficient to induce or enhance pancreatic islet cell phenotype in said cell.

Also included are pharmaceutical composition that includes a compound which increases PDX expression and a pharmaceutically acceptable carrier.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 30A is a table showing PDX-1 repression of C/EBPβ gene expression in liver pancreas, human liver cells-control, human liver cells treated by Ad-CMV-hInsulin, and human liver cells treated by PDX-1 by DNA microarray analysis.

FIG. 30B is a bar chart showing PDX-1 repression of C/EBPβ gene expression by Quantitative RT-PCR analysis.

FIG. 30C is a photograph of a Western Blot showing PDX-1 repression of C/EBPβ intracellular protein levels.

DETAILED DESCRIPTION OF THE INVENTION

Figure 1:
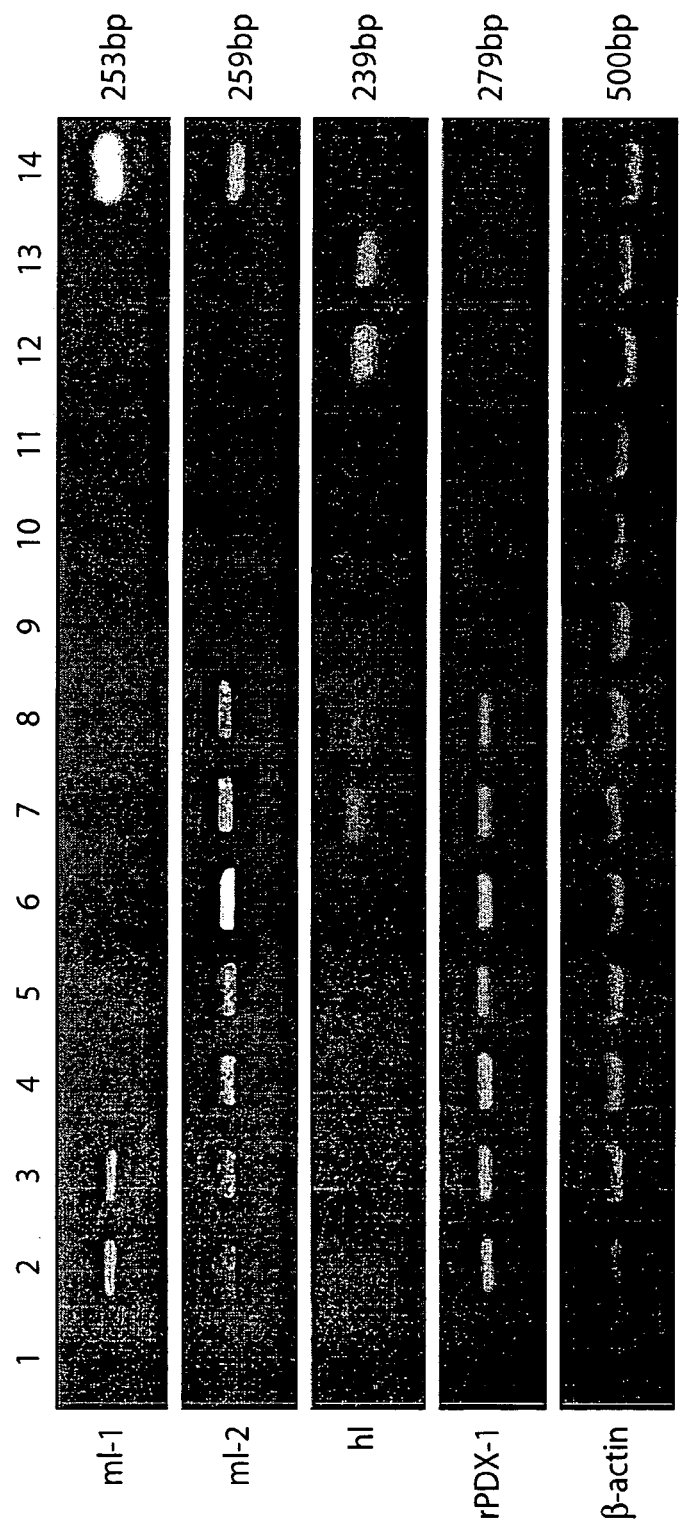
FIG. 1 is an illustration demonstrating detection of mRNA in Balb/c mice liver tissue for mouse insulin I (mI-1), mouse insulin II (mI-2), human insulin, PDX-1 and β-actin after adenovirus treatment as determined by RT-PCR. Lane 1: no DNA (negative control for PCR); lanes 2-6: livers from AdCMV-PDX-1 treated mice lanes 7, 8: livers from AdCMV-PDX-1+AdRIP-1-hIns-treated mice; lanes 9-11: livers from control AdCMV-β-gal+AdRIP-1-hIns-treated mice; lanes 12, 13: livers from AdCMV-hIns-treated mice; lane 14: normal mouse pancreas.

The invention is based in part on the discovery that ectopic expression of pancreatic and duodenal homobox gene 1 (PDX-1) in liver and skin induces a pancreatic islet cell phenotype in liver and skin cells and results in the expression, production and processing of pancreatic hormones. PDX-1 is also known as IDX-1, IPF-1, STF-1 and IUF-1, all of which are collectively referred to herein as "PDX". Additionally, the invention provides methods and pharmaceutical compositions for treating pancreatic disorders.

Recent advance in the outcome of clinical pancreatic islet transplantation for diabetes suggests that continuous control of blood glucose levels could be achieved by pancreatic islet cells implantation. However this successful therapeutic method is severely restricted by limited tissue supply from cadaveric donors, and by the need for lifelong immunosuppression. Islet cell implantation, as a treatment for diabetic patients will be widely available only when new sources of islets or β-cells are found. The optimal source of tissue engineered to replace β-cell function in type I autoimmune diabetes should be easily isolated, largely expanded, and preferentially resists autoimmune attack; these cells may potentially reside in extra-pancreatic tissues.

Ectopic expression of PDX-1 in-vivo delivered by first generation E1 deleted recombinant adenovirus (Ad-CMV-PDX-1) induced both the endocrine and exocrine pancreatic repertoire of gene expression and the production and secretion of processed, biologically active insulin. These results demonstrate that PDX-1 ectopically expressed in a mature fully differentiated organ, PDX-1 functions as a pancreatic differentiation factor. Moreover, although PDX-1 was delivered by in-vivo using the first generation of recombinant adenoviruses, the expression and production of pancreatic hormones persisted more than eight months after treatment.

This surprising capacity of liver to serve as a potential source of tissue for generating functional endocrine pancreas was first demonstrated by us in mice in-vivo using ectopic PDX-1 gene expression. It was shown that short term expression of PDX-1 transgene in mice induced a comprehensive, irreversible and functional transdifferentiation process (i.e., is converting one mature cell characteristics and function into another fully differentiated cell) in a subpopulation of liver cells. In addition is was demonstrated that freshly isolated, adult as well as fetal human liver cells under controlled conditions in in-vitro culture can be induced to transdifferentiate into functional insulin producing tissue. About 50% of the liver cells that expressed the PDX-1 transgene activated the otherwise inactive insulin promoter. Transdifferentiated human liver cells produced the hormone, stored it in secretory granules and released processed insulin in a glucose-regulated manner. Insulin-producing human liver cells were functional and restored normoglycemia in diabetic immunodeficient mice and yclophosphamide-acceleratted diabetes induced in non-obese diabetic mice.

In its various aspects and embodiments, the a invention includes administering to a subject or contacting a cell with a compound (also referred to herein as a PDX inducer compound) that increases PDX expression or activity. PDX expression or activity is increased for example by the compound activating endogenous PDX expression. The compound can be, e.g., (i) a PDX, a NeuroD or a betacellulin polypeptide; (ii) a nucleic acid encoding a PDX, a NeuroD or a betacellulin polypeptide; (iii) a nucleic acid that increases expression of a nucleic acid that encodes a PDX polypeptide and, and derivatives, fragments, analogs and homologs thereof. A nucleic acid that increase expression of a nucleic acid that encodes a PDX polypeptide includes, e.g., promoters, enhancers. The nucleic acid can be either endogenous or exogenous. Optionally, the cell is further contacted with nicotinamide, epidermal growth factor, activin A, hepatic growth factor, exendin, GLP-1 or betacellulin.

As used herein, the term "nucleic acid" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded. Preferably, the nucleic acid is a DNA. A nucleic acid that increase expression of a nucleic acid that encodes a PDX polypeptide includes, e.g., promoters, enhancers. The nucleic acid can be either endogenous or exogenous.

Suitable sources of nucleic acids encoding PDX include for example the human PDX nucleic acid (and the encoded protein sequences) available as GenBank Accession Nos. U35632 and AAA88820, respectively. Other sources include rat PDX nucleic acid and protein sequences are shown in GenBank Accession No. U35632 and AAA18355, respectively, and are incorporated herein by reference in their entirety. An addition source include zebrafish PDX nucleic acid and protein sequences are shown in GenBank Accession No. AF036325 and AAC41260, respectively, and are incorporated herein by reference in their entirety.

The compound can be administered to the subject either directly (i.e., the subject is directly exposed to the nucleic acid or nucleic acid-containing vector) or indirectly (i.e., cells are first transformed with the nucleic acid in vitro, then transplanted into the subject). For example, in one embodiment mammalian cells are isolated from a subject and the PDX nucleic acid introduced into the isolated cells in vitro. The cells are reintroduced into a suitable mammalian subject. Preferably, the cell is introduced into an autologous subject. The routes of administration of the compound can include e.g., parenteral, intravenous, intradermal, subcutaneous, oral (e.g., inhalation), transdermal (topical), transmucosal, and rectal administration. In one embodiment the compound is administered intravenous. Preferably, the compound is implanted under the kidney capsule or injected into the portal vein.

The cell can be any cell that is capable of producing pancreatic hormones, e.g., bone marrow muscle, spleen, kidney, blood, skin, pancreas, or liver. In one embodiment the cell is capable of functioning as a pancreatic islet cell, i.e., store, process and secrete pancreatic hormones, preferably insulin upon an extracellular trigger. In another embodiment the cell is a hepatocyte, i.e., a liver cell. In additional embodiments the cell is totipotent or pluripotent. In alternative embodiments the cell is a hematopoietic stem cell, embryonic stem cell or preferably a hepatic stem cell.

The subject is preferably a mammal. The mammal can be, e.g., a human, non-human primate, mouse, rat, dog, cat, horse, or cow.

Methods of Inducing Pancreatic Hormone Production

In various aspects, the invention provides methods of inducing pancreatic hormone production in a subject. For example, the method can include administering to a subject a compound that increases PDX expression or activity in an amount sufficient to induce pancreatic hormone production.

In another aspect, the method includes providing a cell from a subject, contacting the cell with a compound which increases PDX expression in an amount sufficient to increase pancreatic hormone production and introducing the cell into a subject. In one embodiment pancreatic hormone production occurs in-vitro and in-vivo, upon introducing the cell into the subject. In an alternative embodiment, pancreatic hormone production occurs in-vivo upon introducing the cell in the subject.

The pancreatic hormone can be e.g., insulin, glucogon, somatostatin or islet amyloid polypeptide (IAPP). Insulin can be hepatic insulin or serum insulin. In another embodiment the pancreatic hormone is hepatic insulin. In an alternative embodiment the pancreatic hormone is serum insulin (i.e., a fully processed form of insulin capable of promoting, e.g., glucose utilization, carbohydrate, fat and protein metabolism).

In some embodiments the pancreatic hormone is in the "prohormone" form. In other embodiments the pancreatic hormone is in the fully processed biologically active form of the hormone. In other embodiments the pancreatic hormone is under regulatory control i.e., secretion of the hormone is under nutritional and hormonal control similar to endogenously produced pancreatic hormones. For example, in one aspect of the invention the hormone is under the regulatory control of glucose.

The cell population that is exposed to, i.e., contacted with, the compound can be any number of cells, i.e., one or more cells, and can be provided in vitro, in vivo, or ex vivo.

Methods of Treating or Preventing Pancreatic Related Disorders

Also included in the invention is a method of treating, i.e., preventing or delaying the onset or alleviating a symptom of pancreatic related disorders in a subject. In various aspects the method includes administering to the subject a compound which modulates the PDX expression or activity. "Modulates" is meant to include increase or decrease PDX expression or activity. Preferably, modulation results in alteration of the expression or activity of PDX in a subject to a level similar or identical to a subject not suffering from the pancreatic disorder. In other aspects the method includes administering to the subject a compound which induces a non-pancreatic cell with pancreatic islet cell function, e.g., capable of expressing insulin, somatostatin or glucagon. In one embodiment the compound modulates PDX expression or activity.

The pancreatic disorder can be any disorder associated with the pancreas. For example, the method may be useful in treating pancreatic hormone insufficiencies, (e.g., diabetes (Type 1 and Type II), insulinomas, and hyperglycemia. Essentially, any disorder, which is etiologically linked to PDX activity, would be considered susceptible to treatment.

A subject suffering from or at risk of developing diabetes is identified by methods known in the art such as determining blood glucose levels. For example, a blood glucose value above 140 mg/dL on at least two occasions after an overnight fast means a person has diabetes. A person not suffering from or at risk of developing diabetes is characterized as having fasting sugar levels between 70-110 mg/dL.

Symptoms of diabetes include fatigue, nausea, frequent urination, excessive thirst, weight loss, blurred vision, frequent infections and slow healing of wounds or sores, blood pressure consistently at or above 140/90, HDL cholesterol less than 35 mg/dL or triglycerides greater than 250 mg/dL, hyperglycemia, hypoglycemia, insulin deficiency or resistance. Diabetic or pre-diabetic patients to which the compounds are administered are identified using diagnostic methods know in the art.

The herein-described PDX modulating compound when used therapeutically are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the present invention including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. *J Biol Chem* 262:4429-4432); (iv) construction of a Therapeutic nucleic acid as part of a retroviral, adenoviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, e.g.: a delivery pump (See, e.g., Saudek, et al., 1989. *New Engl J Med* 321:574 and a semi-permeable polymeric material (See, e.g., Howard, et al., 1989. *J Neurosurg* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Boca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. *Proc Natl Acad Sci USA* 88:1864-1868), and the like. Alternatively, a nucleic acid Therapeutic can be introduced intracellularly and incorporated within host cell DNA for expression, by homologous recombination or remain episomal.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally about 20-500 micrograms (μg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The duration of intravenous therapy using the Therapeutic of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Cells may also be cultured ex vivo in the presence of therapeutic agents or proteins of the present invention in order to proliferate or to produce a desired effect on or activity in such cells. Treated cells can then be introduced in vivo for therapeutic purposes.

Methods of Inducing Islet Cell Phenotype and Function

The invention also includes a method of inducing or enhancing a one or more pancreatic islet cell phenotypes in a cell. In one embodiment the pancreatic cell phenotype is induced in a non-islet cell type. For example, a non-pancreatic cell is converted (i.e., transdifferentiated) to a pancreatic cell by contacting a cell with a PDX-1 inducer compound. The cell is contacted with a PDX inducer in an amount to induce the expression of endogenous PDX-1, an embryonic marker, insulin, glucogon, or somatostatin in the non-pancreatic cell. Alternatively the cell is contacted with a PDX inducer in an amount to repress the expression of C/EBPβ, albumin or ADH-1 in the non-pancreatic cell. The method includes contacting a cell with a compound that modulates islet cell specific transcription factors, e.g., PDX-1, beta 2, ISL-2, Nkx6.1, Ngn3.1, or NKx2.2. in an amount sufficient to induce or enhance the pancreatic islet cell phenotype, e.g., beta, alpha and delta islet cells. Preferably, the compound increases PDX expression (e.g. endogenous PDX-1 expression), production or activity. Preferably the method induces a pancreatic islet β-cell phenotype.

By "pancreatic islet cell phenotype" is meant that the cell displaying one or more characteristics typical of pancreatic islet cells, i.e. hormone production, processing, storage in secretory granules, nutritionally and hormonally regulated secretion or characteristic islet cell gene expression profile. The pancreatic islet cell phenotype can be determined for example by measuring pancreatic hormone production, e.g., insulin, somatostatin or glucagon. Hormone production can be determined by methods known in the art, e.g. immunoassay, western blot, receptor binding assays or functionally by the ability to ameliorate hyperglycemia upon implantation in a diabetic host.

The cell can be any cell that is capable of expressing a pancreatic islet cell phenotype, e.g., muscle, bone marrow, spleen, kidney, skin, pancreas, or liver. In one embodiment the cell is capable of functioning as a pancreatic islet cell, i.e., store, process and secrete pancreatic hormones, preferably insulin upon an extracellular trigger. In another embodiment the cell is a hepatocyte, i.e., a liver cell. The cell is a mature cell, i.e., a differentiated cell. In additional embodiments the cell is totipotent or pluripotent. In alternative embodiments the cell is a hematopoietic stem cell, embryonic stem cell or preferably a hepatic stem cell.

The cell population that is exposed to, i.e., contacted with, the compound can be any number of cells, i.e., one or more cells, and can be provided in vitro, in vivo, or ex vivo.

Methods of Inducing a Pancreatic Islet Gene Expression Profile

The invention also includes a method of inducing or enhancing a pancreatic islet gene expression profile in a subject or a cell. By "pancreatic gene expression profile" is meant to include one or more genes that are normally transcriptionally silent in non-endocrine tissues, e.g., a pancreatic transcription factor an endocrine gene, or an exocrine gene. For example, expression of PC1/3, insulin, glucagon, somatostatin or endogenous PDX-1. The method includes administering to a subject a compound that increases PDX expression or activity in an amount sufficient to induce a pancreatic islet or endocrine gene expression profile. In one embodiment the method induces PC1/3 gene expression in a subject.

Induction of the pancreatic gene expression profile can be detected using techniques well known to one of ordinary skill in the art. For example, pancreatic hormone RNA sequences can be detected in, e.g., northern blot hybridization analyses, amplification-based detection methods such as reverse-transcription based polymerase chain reaction or systemic detection by microarray chip analysis. Alternatively, expression can be also measured at the protein level, i.e., by measuring the levels of polypeptides encoded by the gene. In a specific embodiment PC1/3 gene or protein expression can be determined by its activity in processing prohormones to their active mature form. Such methods are well known in the art and include, e.g., immunoassays based on antibodies to proteins encoded by the genes, or HPLC of the processed prohormones.

Methods of Identifying Genes the Expression of which is Modulated by Pdx

The invention also includes a method of identifying nucleic acids the expression of which modulated by PDX. The method includes measuring the expression of one or more nucleic acids in a test cell population exposed to a compound that modulates PDX activity or expression. Expression of the nucleic acid sequences in the test cell population is then compared to the expression of the nucleic acid sequences in a reference cell population, which is a cell population that has not been exposed to the compound, or, in some embodiments, a cell population exposed the compound. Comparison can be performed on test and reference samples measured concurrently or at temporally distinct times. An example of the latter is the use of compiled expression information, e.g., a sequence database, which assembles information about expression levels of known sequences following administration of various agents. For example, alteration of expression levels following administration of compound can be compared to the expression changes observed in the nucleic acid sequences following administration of a control agent, such a PDX nucleic acid.

An alteration in expression of the nucleic acid sequence in the test cell population compared to the expression of the nucleic acid sequence in the reference cell population that has not been exposed to the compound indicates expression of the nucleic acid is modulated by PDX.

The test cell can be taken from any tissue capable of being modulated by PDX, e.g., pancreas, liver, spleen, or kidney. In one embodiment the cell is from a non-endocrine tissue. Preferably, the cell is liver tissue.

Preferably, cells in the reference cell population are derived from a tissue type as similar as possible to test cell, e.g., liver tissue. In some embodiments, the control cell is derived from the same subject as the test cell, e.g., from a region proximal to the region of origin of the test cell. In other embodiments, the control cell population is derived from a database of molecular information derived from cells for which the assayed parameter or condition is known.

Expression of the nucleic acids can be measured at the RNA level using any method known in the art. For example, northern hybridization analysis using probes which specifically recognize one or more of these sequences can be used to determine gene expression. Alternatively, expression can be measured using reverse-transcription-based PCR assays. Expression can be also measured at the protein level, i.e., by measuring the levels of polypeptides encoded by the gene products. Such methods are well known in the art and include, e.g., immunoassays based on antibodies to proteins encoded by the genes.

When alterations in gene expression are associated with gene amplification or deletion, sequence comparisons in test and reference populations can be made by comparing relative amounts of the examined DNA sequences in the test and reference cell populations.

The invention also includes PDX modulated nucleic acids identified according to this screening method, and a pharmaceutical composition comprising the PDX modulated nucleic acids so identified.

PDX Recombinant Expression Vectors and Host Cells

Another aspect of the invention pertains to vectors, preferably expression vectors, containing a nucleic acid encoding a PDX protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentivirus, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PDX proteins, mutant forms of PDX, fusion proteins, etc.).

The recombinant expression vectors of the invention can be designed for expression of PDX in prokaryotic or eukaryotic cells. For example, PDX can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111-2118). Such alteration of nucleic acid sequences of the invention can be carried out by standard DNA synthesis techniques.

In another embodiment, the PDX expression vector is a yeast expression vector. Examples of vectors for expression in yeast S. cerevisiae include pYepSec1 (Baldari, et al., (1987) *EMBO J*6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, PDX can be expressed in insect cells using baculovirus expression vectors. Baculovirus vectors available for expression of proteins in cultured insect cells (e.g., SF9 cells) include the pAc series (Smith et al. (1983) *Mol*

*Cell Biol* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268-277), lymphoid-specific promoters (Calame and Eaton (1988) *Adv Immunol* 43:235-275), in particular promoters of T cell receptors (Winoto and Baltimore (1989) *EMBO J* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374-379) and the α-fetoprotein promoter (Campes and Tilghman (1989) *Genes Dev* 3:537-546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PDX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX, and may either maintain or loose original characteristics.

A host cell can be any prokaryotic or eukaryotic cell. For example, PDX protein can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. integration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding PDX or can be introduced on a separate vector. Cells stably transfected with the introduced nucleic acid can be identified by drug selection (e.g., cells that have incorporated the selectable marker gene will survive, while the other cells die). In another embodiment the cells modulated by PDX or the transfected cells are identified by the induction of expression of a endogenous reporter gene. In a specific embodiment, the promoter is the insulin promoter driving the expression of green fluorescent protein (GFP).

In one embodiment the PDX nucleic acid is present in a viral vector. In another embodiment the PDX nucleic acid is encapsulated in a virus. In some embodiments the virus preferably infects pluripotent cells of various tissue type, e.g. hematopoietic stem, cells, neuronal stem cells, hepatic stem cells or embryonic stem cells, preferably the virus is hepatotropic. By "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

Gene Therapy

In one aspect of the invention a nucleic acid or nucleic acids encoding a PDX polypeptide, or functional derivatives thereof, are administered by way of gene therapy. Gene therapy refers to therapy that is performed by the administration of a specific nucleic acid to a subject. In this aspect of the invention, the nucleic acid produces its encoded peptide(s), which then serve to exert a therapeutic effect by modulating function of an aforementioned disease or disorder. e.g., diabetes. Any of the methodologies relating to gene therapy available within the art may be used in the practice of the present invention. See e.g., Goldspiel, et al., 1993. *Clin Pharm* 12: 488-505.

In a preferred embodiment, the therapeutic comprises a nucleic acid that is part of an expression vector expressing any one or more of the aforementioned PDX polypeptides, or fragments, derivatives or analogs thereof, within a suitable host. In a specific embodiment, such a nucleic acid possesses a promoter that is operably-linked to coding region(s) of a PDX polypeptide. The promoter may be inducible or constitutive, and, optionally, tissue-specific. The promoter may be, e.g., viral or mammalian in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932-8935. In yet another embodiment the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599-618. The chosen technique should provide for the stable transfer of the nucleic acid to the cell, such that the nucleic acid is expressible by the cell. Preferably, said transferred nucleic acid is heritable and expressible by the cell progeny. In an alternative embodiment, the transferred nucleic acid remains episomal and induces the expression of the otherwise silent endogenous nucleic acid.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle which is suitable for administration to an animal e.g., physiological saline. A therapeutically effective amount is an amount which is capable of producing a medically desirable result, e.g., an increase or decrease of a PDX or gene product in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. For example the DNA is administers at approximately $2 \times 10^{12}$ virions per Kg.

Pharmaceutical Compositions

The compounds, e.g., PDX polypeptides, nucleic acid encoding PDX polypeptides, or a nucleic acid that increases expression of a nucleic acid that encodes ad PDX polypeptide. (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PDX polypeptide or PDX encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the bather to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *PNAS* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

The invention will be further described in the following examples, which do not limit the scope of the invention described in the claims.

EXAMPLE 1

General Methods

The following general methods were used to perform the experiments described herein.

Recombinant Adenoviruses

AdCMVPDX-1 was constructed as described in by R. Seijffers et al. *Endocrinology* 140:1133 (1999). It contains the STF-1 cDNA, the rat homolog of PDX-1 ligated into BamH1 site of pACCMVpLpA vector.

AdCMVβ-gal, contains the nuclear localization signal for β-galactosidase.

AdCMV-hIns, contains the human insulin cDNA under the control of the heterologous cytomegalovirus promoter.

AdRIP-1-hIns, contains the human insulin cDNA under the control of the rat insulin promoter-1 (RIP-1). RIP-1, is 410 bases of the 5' flanking DNA region of the rat insulin-1 gene.

All first-generation recombinant adenoviruses were constructed according to Becker et al.[39]. The gene of interest was ligated into the pACCMV.pLpA plasmid, followed by co-transfection with the adenovirus plasmid pJM17 and followed by harvesting the recombinant virions from HEK-293 cells. Ad-CMV-PDX-1 carries the rat homologue of PDX-1 while Ad-CMV-hIns carries the human insulin cDNA, distal to a CMV promoter[40]. Ad-RIP-GFP-CMV-PDX-1 is a bi-functional recombinant adenovirus that was prepared by insertion of 410 nucleotides of the 5'-flanking region of the rat insulin-1 gene (supplied by Dr. Larry Moss) in place of the viral CMV promoter in the pACCMV.pLpA plasmid to drive GFP gene expression (HindIII/PstI), followed by NotI/NotI insert containing CMV-mPDX-1 (mouse homologue of PDX-1) from pACCMV-PDX-1.pLpA plasmid[40]. The specific function of the recombinant virus was analyzed in insulinoma cell lines compared to non-β cell lines. Preparation of viral stocks was performed as previous described[40].

Cell Culture

The mouse pancreatic derived cell line β-TC-1, α-TC-1 and the rat pancreatic cell line RIN1046-38 were cultured according to previously published conditions (21,22).

Animals and Recombinant Adenoviruses

Mice were housed in an air-conditioned environment, under a 12-hour light/dark cycle, and handled according to institutional animal welfare regulation. Balb/c mice (8-9 weeks old, 24-27 gr.). were treated by $1-5 \times 10^{10}$ moi of the indicated recombinant adenoviruses by systemic injection into the tail vein (in a volume of 200-300 µl physiological saline). Blood was drawn from the tail, for determination of glucose concentration (Accutrend® GC, Boehringer Mannheim, Mannheim, Germany). Liver was harvested for immunohistochemical staining (fixed in 4% formaldehyde and embedded in paraffin), for analysis of gene expression (total RNA), and for determination of pancreatic hormone content in liver. For the last two analyses, hepatic specimens were immediately frozen in liquid nitrogen, and stored at −70° C.

Male NOD/LtJ and NOD/Scid mice were maintained under pathogen-free conditions in the Animal Breeding Center of the Weizmann Institute of Science. Experiments were carried out under the supervision and guidelines of the Animal Welfare Committee. The mice were 1 month old at the start of the experiments.

Human Liver Cells

Adult human liver tissues were obtained from 8 different liver transplantation surgeries from 4-10 years old children, and two over forty years old individuals.

Fetal human livers were obtained from 4 different deliberate abortions of 20-22 weeks gestation. Both adult and fetal liver tissues were used with approval from the Committee on Clinical Investigations (institutional review board).

Cell Harvest and Culture Conditions

Isolation of human hepatocytes was performed as previously described[41]. In short: Liver samples were irrigated at cold Hank's Balanced Salt solution (HBSS), cut into thin slices (1-2 mm thick), and digested by 0.03% Collagenase type I (Worthington Biochemical Corp.) for 20 minutes at 37° C. Dissociated cells were collected, washed twice in HBSS+EGTA (5 mM) and collected by centrifugation at 500×g for 5 minutes at 4° C. The cells were resuspended in Dulbecco's minimal essential medium (1 gr/L glucose) supplemented with 10% FCS, 100 U/ml penicillin, 100 µg/ml streptomycin and 250 ng/ml amphotericin B (Biological Industries, Israel). Cell viability and number were determined and cells were plated on fibronectin (3 µg/cm$^2$, Biological Industries, Israel) pre-coated plates at $1-2 \times 10^5$ cells/ml. The medium was changed daily during the first three days in order to remove non-adherent cells. Confluent cultures were split 1:3 using 0.05% trypsin-EDTA solution. The cells were kept at 37° in a humidified atmosphere of 5% $CO_2$ and 95% air.

Viral Infections and Growth Factors Treatment

Liver cells were cultured in Dulbecco's minimal essential medium (1 gr/L glucose) with or without growth factors as indicated separately (EGF 20 ng/ml, Cytolab Ltd.; Nicotinamide 10 mM, Sigma), and were infected by recombinant adenoviruses (500 moi) for 5 days. The recombinant adenoviruses used in this study: Ad-RIP-GFP-CMV-PDX-1, Ad-CMV-PDX-1, Ad-CMV-hIns[40], Ad-CMV-GFP (Clontech, BD Biosciences).

RNA Isolation and RT-PCR Analysis.

Total RNA was isolated from frozen tissues using Tri-Reagent (Molecular Research Center, Ohio). RNA samples were treated by 10 units of RQ1 RNase-free DNaseI (Promega), for 60 minutes. cDNA was prepared by reverse transcription (Native AMV Reverse Transcriptase, Chimerx), using 4 µg DNA-free total RNA and 0.5 µg oligo(dT)$_{15}$. PCR was performed using T3 Thermocycler (Biometra, Gottingen, Germany) and products were separated on 1.8% agarose gels and visualized with ethidium bromide. The sequence of the primers used for PCR and reactions conditions were as listed in table 1 and in table 3. Note that in order to discriminate between expression of the endogenous mouse PDX-1 and the ectopic rat homologue, two sets of specific oligonucleotide primers were designed (see table 1 and table 3).

Real Time PCR

RT-PCR was performed on the LightCycler (Roche Applied Science, Mannheim, Germany), using SYBR-Green I dye.

Amplification conditions included initial denaturation at 95° C. 10 minutes, followed by 55 cycles for both mouse and rat PDX-1, or 30 cycles for β-actin. For both PDX-1 homologues, each cycle included denaturation at 95° C. for 15 seconds, annealing at 59° C. and extension at 72° C. for 15 seconds. Annealing for β-actin was performed at 56° C. for 10 seconds. The fluorescent signal was monitored 5 seconds after each cycle at 90° C. for β-actin, 87° C. for mouse PDX-1 and 88° C. for rat PDX-1. Melting curve program was carried out at 68° C. for 40 seconds, to analyze the specificity of the generated products.

The RT-PCR for mouse PDX-1 was performed 3 times and for rat PDX-1 2 times.

Both rat and mouse PDX-1 levels were normalized to the respective β-actin mRNA levels, in the same samples.

Alternatively, quantitative real-time RT-PCR, was performed using ABI Prism 7000 sequence Detection system (Applied Biosystems).

The TaqMan™ fluorogenic probes, Assay-On-Demand (Applied Biosystems) used in this study were: Human β-actin Hs99999903_m1; Human Insulin Hs00355773_m1; Human Glucagon Hs00174967_m1; Human Somatostatin Hs00356144_m1; Human PDX-1 Hs00173014_m1; Human Glut-2 Hs00165775_m1; Human Glucokinase Hs00175951_m1; Human PC2 Hs00159922_m1; Human SCG2 Hs00185761_m1; Human SGNE1 Hs00161638_m1.

Amplification conditions included initiation at 50° C. for 2 minutes, denaturation at 95° C. for 10 minutes, followed by 40 cycles, each cycle included denaturation at 95° C. for 15 seconds and annealing at 60° C. for 1 minute, using the TaqMan PCR Master Mix (Applied Biosystems). Relative quantitative analysis was according to ABI prism 7000 SDS software, using the $2^{(-\Delta Ct)}$ equation. The mRNA levels were corrected for human β-actin mRNA.

Pancreatic Hormones Immunohistochemistry.

Slides of 4 µm paraffin-embedded sections were deparaffinized, incubated in 3% $H_2O_2$, and were incubated in blocking solution (for both Insulin and Glucagon detection), using the commercially available Histomouse™-SP Kit (Zymed laboratories, South San Francisco, Calif.). Sections were then incubated for 1 h at 37° C. with monoclonal antibodies against human insulin and against human glucagon (Sigma), both at a dilution of 1:200. Slides were exposed to the secondary biotinylated IgG for 30 minutes at room temperature and then incubated in strepavidin-peroxidase followed by a chromogen peroxide solution. A control using only secondary without primary antibodies followed by strepavidin-peroxidase and a chromogen peroxide solution was performed to rule out possible background of the system.

Radioimmunoassay (RIA) for Pancreatic Hormones.

Pancreas and livers were isolated, immediately frozen in liquid nitrogen, and stored at −70° C. Frozen tissues were homogenized in 0.18N HCl/35% ethanol. The homogenates were extracted overnight at 4° C. with continuous stirring, and the supernatants were lyophilized. Samples were dissolved in 0.8 ml RIA Assay Buffer, supplemented by a cocktail of protease inhibitors (Sigma). Hepatic insulin and glucagon levels were determined using rat radioimmunoassay (RIA, catalog no. SRI-13K and GL-32K, Linco, Mo., USA, and Coat-A-Count, DPC; CA, USA). Somatostatin concentrations were determined by RIA (Euro-diagnostica, Sweden). Hepatic content of pancreatic hormones was normalized to the weight of the extracted tissue.

Determination of Hepatic Function.

Serum biochemistry profile consisting of albumin, AST (Aspartate aminotransferase), ALT (Alanine aminotransferase) and total billirubin was determined using Olympus AU 2700 Apparatus (Olympus, Germany) in serum samples.

Insulin and C-Peptide Detection

Insulin and C-peptide secretion and content from primary adult liver cells were measured by static incubation of 48 hours after 3 days of initial viral and growth factors treatment. Insulin secretion into the media was measured by RIA using the Ultra Sensitive Human Insulin RIA kit (Linco Research) and C-peptide secretion was measured by Human C-Peptide RIA kit (Linco Research).

Insulin content was measured after homogenizing the cell pellet in 0.18 N HCl, 35% ethanol. The homogenates were extracted overnight at 4° C. with continuous stirring, and the supernatants were lyophilized. Samples were dissolved in 0.5 ml PBS containing 0.2% BSA and Protease Inhibitory cocktail (Sigma). 100 µl sample were used for the RIA. Insulin content was normalized to total cellular protein, measured by the Bio-Rad Protein Assay kit.

Glucose Challenge Assay

Adult liver cells were treated with Ad-CMV-PDX-1 and growth factors for 5 days. The cells were plated in 6-well plates at $10^5$ cells per well.

For time course analysis the cells were preincubated for 2 hours in Krebs-Ringer buffer (KRB) containing 0.1% BSA, followed by incubation for the indicated period in media containing 2 mM or 25 mM glucose. At each time point media samples were analyzed for insulin (Ultra Sensitive Human Insulin RIA kit—Linco Research) and C-peptide secretion (Human C-Peptide RIA kit—Linco Research).

Glucose dose response; Cells were preincubated for 2 hours with KRB containing 0.1% BSA, washed and challenged thereafter with increasing concentrations of D-Glucose or 2-deoxy-Glucose (0-25 mM) for 2 hours. At the end of the incubation period at 25 mM glucose, the cells were washed with KRB and incubated for additional 2 hours in 2 mM glucose containing media.

Electron Microscopy

Liver cells were fixed in 2.5% Gluteraldehyde, osmificated, dehydrated with a graded series of ethanol and propylene oxide, and embedded in Araladite solution (Polyscience Inc.). Ultra-thin sections were cut in an ultramicrotome, stained with 2% uranyl acetate and Reynolds' lead citrate solution. For post-embedding immunogold reactions, 50-90 nm liver sections were put on nickel grids. The grids were incubated with antibody against insulin (guinea-pig polyclonal; 7.8 µg/ml, Dako) at room temperature for O.N and then incubated with immunogold-conjugated antibody against guinea-pig IgG (15-nm gold; diluted 1:40, Dako) for 1.5 hours at room temperature. The sections were observed under an electron microscope (Jeol 1200EX2).

Cell Transplantation

Five-weeks-old nonobese diabetic severe combined immunodeficient (SCID-NOD) male mice (Weizmann Institute, Israel) were rendered hyperglycemic by intra-peritoneal injection of streptozotocin (Sigma) at 180 mg/kg of body weight. When blood glucose reached levels of about 300 mg/dl on two consecutive measurements, mice were transplanted under the kidney capsule, with $3 \times 10^6$ human liver cells pretreated with PDX-1 and growth factors for 5 days in 50 µl of Matrigel (Sigma) by using a 30-gauge needle. Blood was drawn from the tail twice a week, for determination of glucose concentration (Accutrend® GC, Roche Applied Science). Serum was collected in blood of fed mice for C-peptide and insulin levels analyses, by using the Ultrasensitive Human C-Peptide ELISA kit (Mercodia) with 0% cross reactivity to mouse C-peptide and the mouse Insulin ELISA kit (Mercodia) with 0% cross reactivity to human insulin, according to the manufacturers' instructions. Kidney and pancreas were harvested for immunohistochemical analysis.

Histology and Staining

Kidney and pancreas were fixed in 4% formaldehyde and embedded in paraffin. Sections of the 5 m in thickness paraffin-embedded tissues were deparaffinized, incubated in 3% $H_2O_2$, and then were either microwaved in citrate buffer for antigen retrieval before being incubated in blocking solution (PDX-1 detection) or immediately exposed to the blocking solution (insulin detection), using Histomouse™-SP Kit (Zymed laboratories). For detection of PDX-1, sections were incubated overnight at 4° C. with antiserum raised against the N-terminal portion of frog PDX-1 (1:5000, a gift from C.V.E. Wright). For detection of insulin, sections were incubated for 1 h at 37° C. with a monoclonal antibody against human insulin (1:100; Sigma). Slides were exposed to the secondary biotinylated IgG for 30 min and then incubated in streptavidin-peroxidase followed by a chromogen peroxide solution.

Cyclophosphamide-accelerated diabetes (CAD)

Diabetes onset was accelerated as previously described (3) with cyclophosphamide (Sigma, Rehovot, Israel). Male NOD mice received an i.p. injection of 200 mg/kg of cyclophosphamide at the age of 4 weeks. If the mice did not become diabetic within the following 2 weeks, they were given a second i.p. injection (200 mg/kg) of Cy, and the process was repeated once more, after a week. Diabetic mice were removed from the SPF and housed in an air-conditioned environment, under a 12-hour light/dark cycle, where they were allowed to acclimatize for 72 h before a new measurement of glycemia was taken to confirm diabetes.

Hyperglycemia

Blood glucose was measured twice weekly using an Accutrend® GC Glucose Analyzed (Boehringer Mannheim, Mannheim, Germany). A mouse was considered diabetic when its blood glucose concentration was higher than 300 mg/dl on two consecutive examinations Virus Injection Diabetic NOD mice 8-10 weeks old (weighting 20-22 gr.) received $1.5 \times 10^{10}$ pfu of the indicated recombinant adenovirus by systemic injection into the tail vein. The viruses were administered in a volume of 200-300 µl of PBS.

Pancreas Histology

Pancreata and livers were fixed in 4% formaldehyde, embedded in paraffin, cut and stained by standard hematoxylin and eosin Immunohistochemical staining, slides of 4 µm paraffin-embedded sections were deparaffinized, blocked and analyzed using the Histomouse™-SP Kit (Zymed laboratories, South San Francisco, Calif.), as described in (21). Sections were incubated with a 1/100 dilution of a monoclonal antibody to human insulin (Sigma, Rehovot, Israel). Slides were developed using an anti-mouse IgG biotinylated antibody in combination with streptavidin-peroxidase followed by a chromogen peroxide solution Control slides were developed in parallel following the same protocol but without adding the insulin-specific antibody.

EXAMPLE 2

Determination of PDX-1 Induced Endogenous Insulin Gene Expression and Activation of Ectopically Co-Delivered Insulin Promoter To assess the effect of ectopic PDX-1 expression in the liver, male Balb/c and C57BL/6 mice (11-14 week old) were injected with $2 \times 10^9$ plaque forming units (in 0.2 ml saline) of AdCMV-PDX-1 recombinant adenovirus into the tail vein. As controls, mice were similarly injected with AdCMV-β-gal, or AdCMV-hIns and AdRIP-1-hIns recombinant adenoviruses. The animals were housed in an air-conditioned environment, under a 12-hour light/dark cycle, on a regular unrestricted diet, and sacrificed one week following virus administration. The liver, spleen, pancreas and kidney were dissected and were immediately frozen in liquid nitrogen, and stored at –70° C. for total RNA isolation.

PDX-1 and insulin gene expression was determined by RT-PCR. Total RNA was isolated from frozen tissues using RNAzol (CINNA-BIOTEX). RNA samples were treated by 10 ul of DNase I (Promega). cDNA was prepared by reverse transcription, using 1 µg DNA-free total RNA and 0.5 µg oligo(dT)$_{15}$. 1.5 µl of RT reaction was amplified using primers and PCR conditions as indicated in Table 1 below. PCR was carried out in a GeneAmp PCR system 2400 (Perkin Elmer), and products were separated on 1.7% agarose gel. A separate PCR reaction was carried out for each RNA sample without reverse transcriptase, to ensure that the amplified product was not due to DNA contamination. The primers were designed to detect the only the ectopic rat PDX-1 expression not the mouse homolog. The primers for ml-2 amplification are located on different exons. The first step of sample denaturation was identical for all amplified genes: 94° C. for 1 minute.

Analysis of the total RNA revealed that AdCMV-PDX-1 administration resulted in PDX-1 expression mainly in liver. Spleen, pancreas and kidney from the same mice tested negative by RT-PCR for the rat homolog of PDX-1.

75% (25 of 35) of the mice that tested positive for the ectopic rat PDX-1 message expressed the mI-2 gene whereas 35% of the mice expressed mI-1 gene (FIG. 1). To determine whether this disparity of expression between mI-2 and mI-1 was due the mI-1 promoter being differentially effected by the identity or the levels of transcription factors present in PDX-1 expressing liver cells, AdRIP-1-hIns recombinant adenovirus was co-delivered with AdCMV-PDX-1 to mice as described above. As demonstrated in FIG. 1, in livers where PDX-1 induced only the expression of the endogenous mI-2, it also activated the rate insulin-1 promoter (RIP-1). This suggests that the different levels of DNA methylation or distinct chromatin structure could be the cause of the low efficiency of the activation of the endogenous nil-1 expression by PDX-1 expression in the liver. Furthermore these data demonstrate the capacity to activate the β-cell specific insulin promoter in liver when co-delivered with PDX.

The expression of the endogenous mouse insulin and the ectopic human insulin genes was not induced by treatment with the same concentration of the control recombinant adenoviruses AdCMV-β-gal, or AdCMV-hIns and AdRIP-1hIns, respectively (n=20). These results demonstrate that PDX-1 is essential and sufficient to induce expression of the endogenous insulin genes and to activate RIP-1 in an extra-pancreatic tissue.

EXAMPLE 3

Determination of PDX-1 Induced Somatostatin Gene Expression and Protein Production In-Vivo Animals were treated with recombinant adenovirus as described in EXAMPLE 2. Somatostatin gene expression was determined by RT-PCR as described in EXAMPLE 2, according to the conditions described in Table 1.

Figure 3:
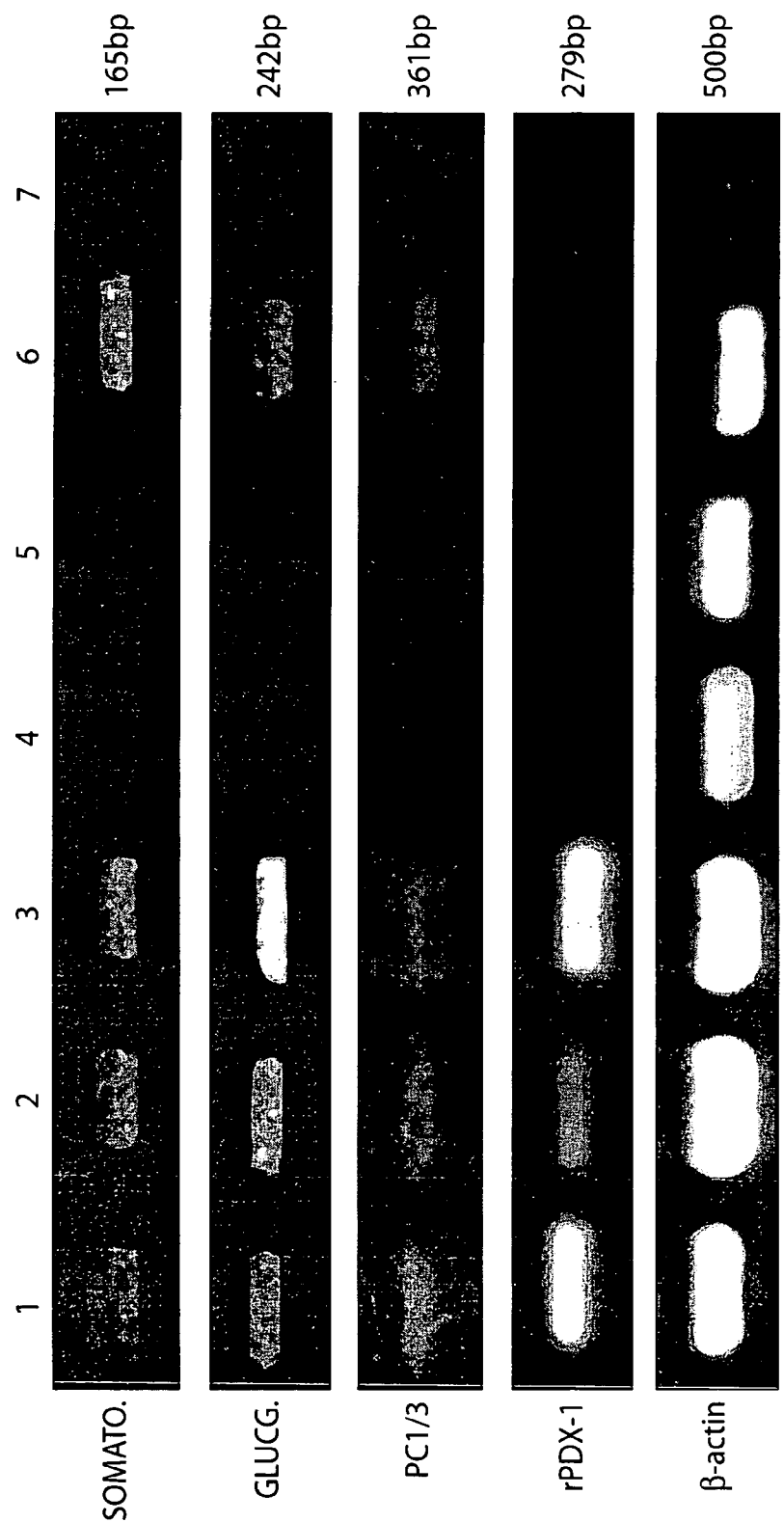
FIG. 3 is an illustration demonstrating detection of mRNA for PDX-1, somatostatin Somato), proinsulin convertase PC1/3 (PC1/3), glucagon (Glucg) and β-actin determined by RT-PCR: Total RNA extracted from PDX-1 and control treated mice was reverse-transcribed using a PC1/3 specific primer. lanes 1-3: mice treated by AdCMV-PDX-1; lanes 4-5: mice treated by AdCMV-β-gal; lane 6: pancreas; lane 7: no cDNA, (control for PCR).

As demonstrated in FIG. 3 livers in mice treated with AdCMV-PDX-1 exhibited somatostatin gene expression. Mice treated with AdCMV-PDX-1 exhibited positive staining for the somatostatin protein in liver tissue analyzed by immunochemistry. Mice treated with AdCMV-β-gal did not express somatostatin.

EXAMPLE 4

Determination of PDX-1 Induced Glucagon Gene Expression

Animals were treated with AdCMVPDX-1 recombinant adenovirus as described in EXAMPLE 2 Glucagon gene expression was determined by RT-PCR as described in EXAMPLE 2, using conditions and primers as described in Table 1.

As demonstrated in FIG. 3 livers in mice treated with AdCMV-PDX-1 exhibited glucagon gene expression. Mice treated with AdCMV-β-gal did not express glucagon.

EXAMPLE 5

Determination of Prohormone Convertase 1/3 Induced Gene Expression

Animals were treated with recombinant adenovirus as described in EXAMPLE 2. Prohormone convertase 1/3 (PC1/3) gene expression was determined by RT-PCR as described in EXAMPLE 2 with the exception that cDNA was reverse-transcribed using a gene specific oligonucleotide (TCCAGGTGCCTACAG GATTCTCT) (SEQ ID NO:1) instead of oligo $(dT)_{15}$). As demonstrated in FIG. 3 only livers from animals treated with PDX-1 exhibited the induction of PC1/3 expression, a member of the Kexin family proteases, PC1/3 expression is restricted to endocrine and neuroendocrine cells with regulated secretory pathway. Taken together with the capacity to retain the produced hormones in intracellular compartments suggests a PDX-1 dependent induction of an endocrine phenotype which includes the induction of a regulated pathway for hormone production, processing, storage and secretion.

TABLE 1

RT-PCR analysis for determination of PDX-1 induced gene-expression.

| Gene | Primer Sequences 5'-3' | PCR Product | Annealing °C. | sec | Extension °C. | sec | Cycles |
|---|---|---|---|---|---|---|---|
| Rat PDX-1 (ectopic) | F: CCAGTTTGCAGGCTCGCTGG (SEQ ID NO: 2) R: GCTGCGTATGCACCTCCTGC (SEQ ID NO: 3) | 279 bp | 62 | 60 | 72 | 60 | 31 |
| Human Insulin (ectopic) | F: CTTTGTGAACCAACACCTGTGC (SEQ ID NO: 4) R: GCAGATGCTGGTACAGCATTGT (SEQ ID NO: 5) | 239 bp | 63 | 60 | 72 | 60 | 38 |
| Mouse Insulin I | F: TTGCCCTCTGGGAGCCCAAA (SEQ ID NO: 6) R: CAGATGCTGGTGCAGCACTG (SEQ ID NO: 7) | 253 bp | 62 | 60 | 72 | 60 | 38 |
| Mouse Insulin II | F: TCTTCCTCTGGGAGTCCCAC (SEQ ID NO: 8) R: CAGATGCTGGTGCAGCACTG (SEQ ID NO: 9) | 259 bp | 62 | 60 | 72 | 60 | 38 |
| Mouse β-actin | F: ATGGATGACGATATCGCT (SEQ ID NO: 10) R: ATGAGGTAGTCTGTCAGGT (SEQ ID NO: 11) | 500 bp | 56 | 45 | 72 | 60 | 35 |

TABLE 1 -continued

RT-PCR analysis for determination of PDX-1 induced gene-expression.

| Gene | Primer Sequences 5'-3' | PCR Product | PCR Conditions | | | | |
|---|---|---|---|---|---|---|---|
| | | | Annealing | | Extension | | |
| | | | °C. | sec | °C. | sec | Cycles |
| Mouse PC1/3 | F: CTGGTTGTCTGGACCTCTGAGTA (SEQ ID NO: 12) R: CCAACAGCAGAA GTGAGTGTGAC (SEQ ID NO: 13) | 361 bp | 55 | 45 | 72 | 60 | 38 |
| Mouse PDX-1 (endogenous) | F: CAAGCTCGCTGGGATCACTGGAGCAG (SEQ ID NO: 14) R: GATGTGTCTCTCGGTCAAGTTCAACATC (SEQ ID NO: 15) | 421 bp | 58 | 45 | 72 | 60 | 38 |
| Mouse & Rrat somatostatin | F: CCTGGCTTTGGGCGGTGTCA (SEQ ID NO: 16) R: CTCGGGCTCCAGGGCATCATTC (SEQ ID NO: 17) | 165 bp | 68 | 45 | 72 | 60 | 38 |
| Mouse glucagon | F: ACCAGCGACTACAGCAAATACCTC (SEQ ID NO: 18) R: AGCAATGGCGACTTCTTCTGG (SEQ ID NO: 19) | 242 bp | 60 | 45 | 72 | 60 | 38 |
| rat insulin-1 | F: GTGACCAGCTACAATCATAG (SEQ ID NO: 20) R: AGTTCTCCAGTTGGTAGAGG (SEQ ID NO: 21) | 370 bp | 57 | 45 | 72 | 60 | 38 |
| Rat β-actin | F: CGTAAAGACCTCTATGCCAA (SEQ ID NO: 22) R: AGCCATGCCAAATGTGTCAT (SEQ ID NO: 23) | 350 bp | 57 | 45 | 72 | 60 | 35 |

TABLE 3

Primer sequences and PCR conditions:

| Gene | Primer sequences | CDNA (µl) | Product (bp) | Annealing | | Cycles |
|---|---|---|---|---|---|---|
| | | | | °C. | sec | |
| β actin | F: ATGGATGACGATATCGCT (SEQ ID NO: 26) R: ATGAGGTAGTCTGTCAGGT (SEQ ID NO: 27) | 1 | 570 | 56 | 45 | 35 |
| Rat PDX-1* | F: CCAAAACCGTCGCATGAAGTG (SEQ ID NO 28) R: CAGCTCGCCTGGTGGCTGT (SEQ ID NO: 29) | 1 | 628 | 60 | 60 | 35 |
| Mouse PDX-1** | F: CCTTCGGGCCTTAGCGTGTC (SEQ ID NO: 30) R: CGCCTGCTGGTCCGTATTG (SEQ ID NO: 31) | 3 | 396 | 59 | 90 | 38 |
| Insulin I | F: TTGCCCTCTGGGAGCCCAAA (SEQ ID NO: 32) R: CAGATGCTGGTGCAGCACTG (SEQ ID NO: 33) | 1 | 253 | 62.6 | 60 | 38 |
| Insulin II | F: TCTTCCTCTGGGAGTCCCAC (SEQ ID NO: 34) R: CAGATGCTGGTGCAGCACTG (SEQ ID NO: 35) | 1 | 259 | 62.6 | 60 | 36 |
| Somatostatin | F: CAGACTCCGTCAGTTTCTGC (SEQ ID NO: 36) R: ACAGGATGTGAAAGTCTTCCA (SEQ ID NO: 37) | 3 | 262 | 54 | 90 | 38 |

TABLE 3 -continued

Primer sequences and PCR conditions:

| Gene | Primer sequences | CDNA (µl) | Product (bp) | Annealing °C. | sec | Cycles |
|---|---|---|---|---|---|---|
| Glucagon | F: ATCATTCCCAGCTTCCCAGA (SEQ ID NO: 38) R: CGGTTCCTCTTGGTGTTCAT (SEQ ID NO: 39) | 2 | 161 | 52 | 60 | 38 |
| IAPP | F: CCACTTGAGAGCTACACCTG (SEQ ID NO: 40) R: GGATTCCCTATTTGGATCC (SEQ ID NO: 41) | 2 | 205 | 54 | 60 | 37 |
| Ad-CMV-PDX-1 | F: CTCAATGGGAGTTTGTTTTGG (SEQ ID NO: 42) R: GGGGGATTAGCACTGAACTCT (SEQ ID NO: 43) | 1 (DNA) | 569 | 8 | 0 | 26 |
| Elastase | F: GGGCACAAACAGACCATCAC (SEQ ID NO: 44) R: GGGATGGGTAAGAAGGTGGT (SEQ ID NO: 45) | 2 | 298 | 5 | 0 | 38 |
| P48 | F: GAAGGTTATCATCTGCCATCG (SEQ ID NO: 46) R: GGGTGGTTCGTTCTCTATGTT (SEQ ID NO: 47) | 3 | 211 | 4 | 0 | 38 |

RT-PCR reaction conditions:
denaturation at 94° C. for 1 min; annealing as presented in the table and extension at 72° C. for 1 min.
*specific primer to rat PDX-1, no recognition of mouse PDX-1
**specific primer to mouse PDX-1, no recognition of rat PDX-1

EXAMPLE 6

PDX-1 Induced Proinsulin Synthesis in Liver S

Animals were treated with recombinant adenovirus as described in EXAMPLE 2. Liver, spleen, pancreas and kidney were dissected. Portions of the tissue fixed in 4% formaldehyde and embedded in paraffin for immunohistochemical staining. The remaining liver and pancreatic tissues were homogenized in 70% ethanol-0.18N HCl, lyophilized and resuspended in PBS (phosphate buffered saline) for RIA determination of IRI content.

Immunohistochemistry

Five µm sections of paraffin-embedded tissues were deparaffinized, incubated in 3% $H_2O_2$, and then, either microwaved in citrate buffer for antigen retrieval prior to incubation in blocking solution (PDX-1 detection), or immediately exposed to the blocking solution (insulin detection). (Histomouse™-SP Kit, Zymed laboratories, CA, USA).

PDX-1 detection: sections were incubated overnight at 4° C. with antiserum raised against the N-terminal portion of frog PDX-1.

Insulin detection: sections were incubated for 1 hour at 37° C. with a monoclonal anti-human-insulin (Sigma, St. Louis Mo.).

Slides were exposed to the secondary biotinylated IgG for 30 minutes, incubated in streptavidin-peroxidase followed by chromogen-peroxide solution.

Immunohistochemical analysis of liver sections from mice treated with PDX-1, revealed expression of the homeoprotein in 30-60% of hepatocyte nuclei, with 0.1-1% of the liver cells staining positive for (pro)insulin. Control AdCMVβ-gal treated livers, did not stain positive for (pro) insulin although β-galactosidase activity was evident in 50% of the nuclei. Livers from mice treated by AdCMV-hIns, did not stain positive for insulin in the hepatic sections, although serum IRI from the same mice was three fold increased, as were serum IRI levels in PDX-1 treated mice. The fact that the ectopic expression of PDX-1 but not of insulin resulted in positive immunostaining for (pro)insulin may suggest the induction of a cellular modulation which supports insulin retention in a small subpopulation of liver cells, (secretory vesicles which belong to the regulated pathway, characteristic to endocrine cells, but not to liver cells), which may have shifted toward a β-cell phenotype.

Radioimmunoassay

To determine whether hepatic insulin mRNA is effectively translated into protein, immunoreactive insulin (IRI) content was tested in extracts derived from hepatic tissue by radioimmunoassay (RIA). Livers from PDX-1 treated mice that tested positive for insulin gene expression by RT-PCR (FIG. 1) contained about 25 fold more IRI than livers of animals treated by a control virus (Table 2). Mean IRI levels in extracts derived from PDX-1 treated livers was 20.7±3.97 µU/mg protein, while in control livers, IRI was only 0.78±0.25 µU/mg protein. The background level of insulin measured in control liver samples possibly represents insulin (of pancreatic origin) bound to its receptors which are abundant in this organ. While IRI detected in PDX-1 treated liver extracts was <1% of the levels detected in pancreatic extracts (Table 2), serum IRI levels in PDX-1 treated mice were almost 3-fold higher compared to controls (323±48.4 vs. 118.2±23.7 µU/ml, respectively (Table 2)), indicating that insulin was being synthesized and a large portion of it secreted into the blood stream. These data indicate that the insulin gene expression induced by the molecular manipulation is successfully translated into specific hepatic production of the pro/hormone.

Immunoreactive insulin detected in PDX-1 treated livers was less than 1% of IRI levels in pancreatic extracts (Table 2). The IRI values determined by radioimmuno-assay (RIA) in liver extracts may under-estimate the actual insulin production in this organ. The antibody we used for RIA preferentially binds the processed hormone, and has only 60% cross-reactivity with proinsulin, which is expected to be present mainly in hepatocytes and to a much lower extent in pancreas.

EXAMPLE 7

Blood Glucose and Serum Insulin Levels

Animals were treated with recombinant adenovirus as described in EXAMPLE 2. Prior to sacrifice, blood was drawn from the inferior vena cava for determination of glucose concentration (Accutrend® GC, Boehringer Mannheim, Mannheim, Germany) and insulin levels by radioimmunoassay (Coat-a-count, DPC, Los-Angeles, Calif., USA, using rat insulin standards, (Linco), the anti-insulin antibody used has only 60% cross-reactivity with human proinsulin).

Mice treated by AdCMV-PDX-1 recombinant adenoviruses were not hypoglycemic, however, their blood glucose levels were significantly lower than of mice treated by AdCMV-β-gal or AdCMV-Luc[197±11.2 vs. 228±15.74 mg/dl, respectively (Table 2). Plasma immunoreactive insulin levels were significantly higher in PDX-1 treated mice compared to controls [323±48.4 vs. 118.2±23.7 µU/ml respectively (Table 2).

The three fold increase in serum IRI levels in PDX-1 treated mice, cannot by itself explain the twenty-fivefold increase (Table 2) in hepatic IRI content demonstrated in PDX-1 treated liver extracts. Thus, the increase in hepatic pro/insulin content originates from local production.

TABLE 2

Blood glucose and immunoreactive insulin
(IRI) levels in serum and liver extracts.

|  | Control virus treated mice | AdCMV-PDX-1 treated mice |
|---|---|---|
| Blood glucose, mg/dl | 228 ± 15.74 (n = 18) | 197 ± 11.2 (n = 40) |
| Serum IRI, µU/ml | 118.2 ± 23.7 (n = 14) | 323 ± 48.4 (n = 26) |
| Liver extracts IRI µU/mg protein | 0.78 ± 0.25 (n = 10) | 20.7 ± 3.97 (n = 12) |
| Pancreas extracts IRI µU/mg protein | 2627 ± 24 (n = 6) |  |

EXAMPLE 8

HPLC Analysis of Insulin-Related Peptides

Animals were treated with recombinant adenovirus as described in EXAMPLE 2. Liver, and pancreas were dissected and homogenized in 70% ethanol-0.18N HCl, lyophilized and resuspended in 0.1 M HCl-0.1% BSA for HPLC analysis.

Insulin-related peptides from the liver and pancreatic extracts were resolved by reverse-phase HPLC using Lichrospher 100 RP-18 column (Merck, Darmstadt, Germany) and elution conditions as described by Gross et al. One ml fractions were collected into tubes containing 0.1 ml 0.1% BSA in water, dried in a Speed-Vac apparatus and reconstituted in 1 ml RIA buffer (0.1% BSA in PBS) for peptide determination by RIA. Guinea pig antiporcine insulin antibodies (Linco, St Charles, Mo.) with either rat or human insulin standards were used for determination of mouse or human IRI, respectively.

Figure 2A:
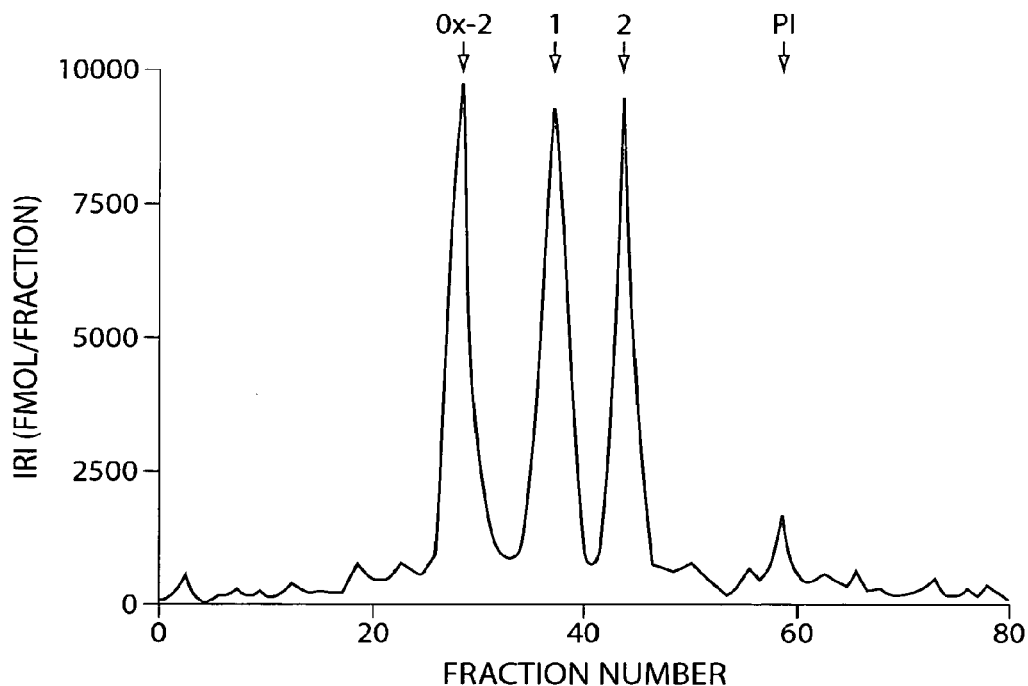
FIG. 2 is an illustration of the HPLC elution profiles of insulin related peptides extracted from murine tissue. Panel A shows the profile from the pancreas of a PDX-1 treated mouse. Panel B shows the profile from the liver of a PDX-1 treated mouse.
Figure 2B:
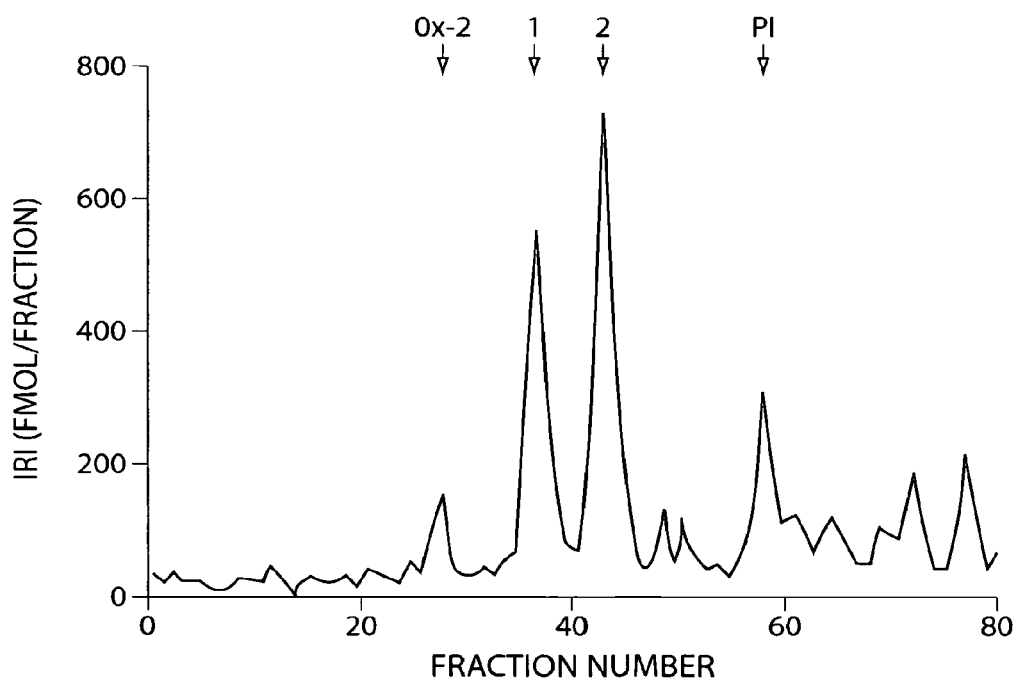

HPLC analysis of hepatic IRI content from PDX-1 treated mice revealed 59±7% (n=3) conversion into fully processed mI-1 and mI-2. In comparison, pancreatic extracts contained 85±5% (n=3) mature insulin (FIG. 2) Whereas, ectopic expression of human insulin (AdCMV-hIns) did not result in retention of IRI in the liver cells except for one liver in which most of the extracted IRI was immature insulin. This is in line with previous observations in transfected FAO cells in which no retention of the insulin gene product observed and most of it was secreted by the constitutive secretory pathway. These data demonstrates that ectopic PDX-1 expression in liver induces a cellular machinery, characteristic to endocrine tissue capable of processing the induced prohormone, and is not induced when only proinsulin is ectopically expressed in liver. Thus, inducing an extended n-cell phenotype in liver cells by ectopic PDX-1 expression.

EXAMPLE 9

Biological Activity of Hepatic Pro/Insulin Production

Figure 4:
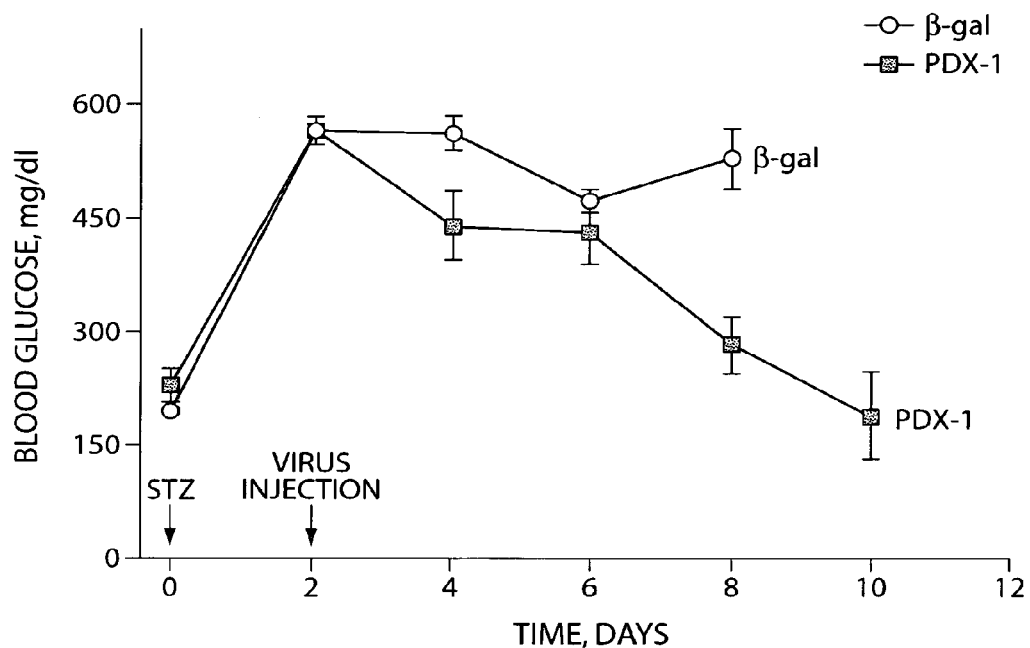
FIG. 4 is an illustration demonstrating ectopic PDX-1 expression in mice livers ameliorates STZ induced hyperglycemia: C57BL/6 males at 12-13 weeks were treated by 220 mg/kg STZ in citrate-buffer. 36-48 hour after STZ treatment mice were injected by AdCMVPDX-1 (n=15 mice), or as control by AdCMVβ-gal (n=22, however, 12 died 3-5 days after STZ treatment, additional 3 mice died 6-7 days after STZ treatment). No mortality occurred upon AdCMVPDX-1 treatment. Each treatment included systemic injection of $2\times10^9$ PFU (plaque forming units) of recombinant adenovirus in 200 μl saline. Glucose levels were determined in blood samples drawn from the ocular vein.

The ability of PDX-1-induced hepatic insulin production to control blood glucose levels in diabetic mice was studied. C57BL/6 mice were rendered diabetic (>600 mg/dl) with ketoacidosis, 24 hours after 200 mg/kg intraperitoneal STZ injection. 24-48 hours after STZ injection, mice were treated by either AdCMV-PDX-1 or by AdCMVβ-gal (control) recombinant adenoviruses administered via the tail vein, in saline solution. As demonstrated in FIG. 4, AdCMV-PDX-1 treated mice, exhibited gradual decrease in blood glucose levels from about 600 to 200-300 mg/dl starting two days after recombinant adenoviral treatment. In contrast, in the control AdCMVβ-gal treated mice, hyperglycemia persisted and was accompanied by increased rate of mortality, 12 out of 22 tested died, with severe ketoacidosis 1-3 days after adenovirus treatment. Furthermore, both groups lost weight after induction of hyperglycemia, and did not regain it back before mice were sacrificed. In summary, the data demonstrate that expression of PDX-1 is sufficient to induce mature, biologically active insulin production in liver which ameliorates hyperglycemia in mice bearing ablated β-cell function.

EXAMPLE 10

In-Vitro Activation of Insulin Promoter by Ectopic PDX-1 Expression

PDX-1 activates rat insulin-1 promoter when co-delivered with a recombinant adenovirus AdRip-1hIns in which human insulin expression is delivered by a rat insulin-1 promoter. (See, EXAMPLE 2 and FIG. 1. PDX-1 was shown to be sufficient to activate rat insulin promoter-1 in-vitro in rat liver cells. Primary cultures if mature and fetal hepatocytes were cultured on collagen-1 covered tissue culture dishes in serum free chemically defined media. Two days after plating cells were treated by either AdCMV-PDX-1& AdRIP-1hIns or by AdCMV β-gal & AdRIP-1hIns. 48 hours after adenoviral treatment, total RNA was extracted and proinsulin genes expression was assessed as described in EXAMPLE 2.

Figure 5:
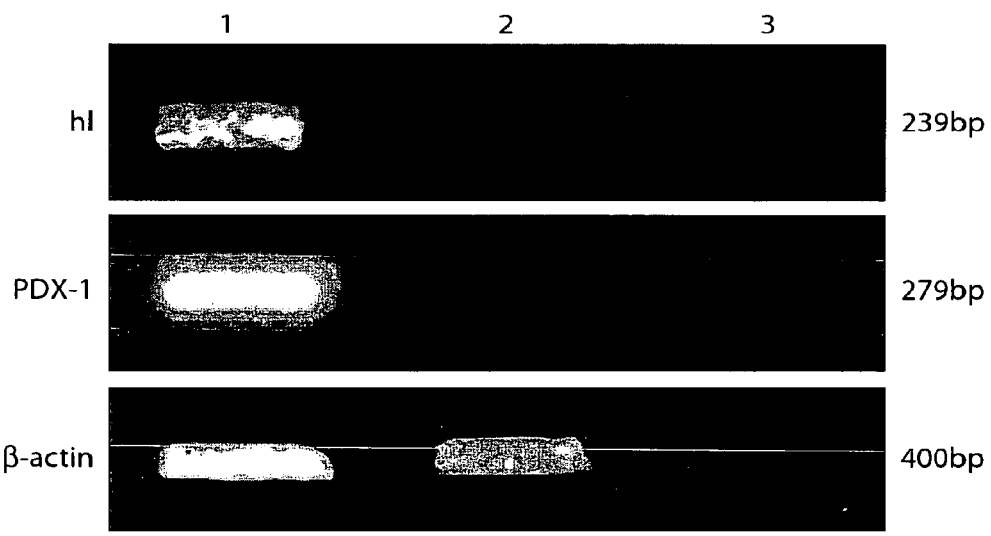
FIG. 5 is an illustration demonstrating ectopic PDX expression in mature hepatocytes in culture activates insulin promoter (rat insulin-1 promoter), co-delivered to the same cells by AdRIPhIns. Human insulin is detected as in FIG. 1. Lane 1: cells treated by AdCMV PDX-1+AdRIP hIns, lane 2: AdCMVβ-galactosidase+AdRIP hIns, lane 3: Control.

PDX-1 activated the ectopically expressed RIP-hIns (rat insulin promoter-1, 410 bps of this promoter, driving human insulin, introduced via recombinant adenovirus), while β-gal did not possess such a capacity. (FIG. 5)

EXAMPLE 11

In-Vitro Induction of Endogenous Somatostatin Gene Expression in Hepatocytes Primary cultures of hepatocytes isolated from fetal (E14-Fisher-344 rats) were cultured and treated by recombinant adenoviruses as described in EXAMPLE 9. Somatostatin gene expression was detected in reverse transcribed total RNA samples as described in EXAMPLE 2, using primers and RT-PCR conditions as described in Table 1.

Figure 6:
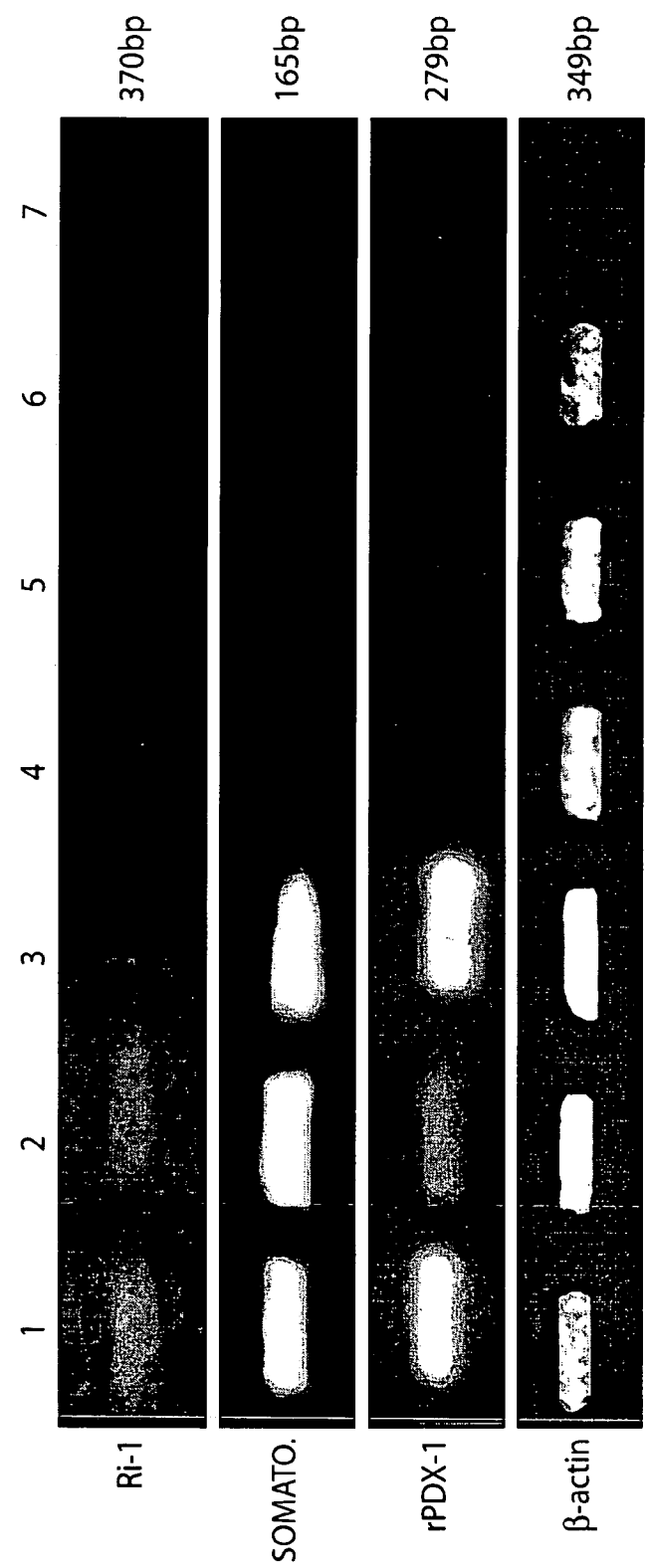
FIG. 6 is an illustration demonstrating the induction of Insulin 1 and Somatostatin gene expression in primary monolayer cultures of fetal Fisher rat (E14) hepatocytes. Fetal hepatocytes were isolated from Fisher 344 rat embryos at day 14 of gestation, and plated on collagen covered tissue culture dishes. Cells were infected by AdCMVPDX-1 at 2-5 MOI (multiplicity of infection=number of viral particles per cell). Total RNA was extracted from the culture 4 days after viral treatment and was analyzed for somatostatin gene expression by RT-PCR. RNA was reversed transcribed as in FIG. 1 using oligo $(dT)_{15}$ primers and amplification by PCR was performed using primers and conditions as elaborated in Table 1. Lanes 1-3: samples from cells treated by PDX-1, lanes 4-6: untreated samples (control) lane 7: no DNA, PCR products were resolved on 1.7% agarose gel electrophoresis.

The data demonstrate that ectopic PDX-1 expression in hepatocytes in-vitro induces the expression of the endogenous, otherwise silent somatostatin gene expression in hepatocytes, in-vitro (FIG. 6).

EXAMPLE 12

In-Vitro Induction of Endogenous Insulin Gene Expression in Hepatocytes

Primary cultures of fetal (E14-Fisher-344 rats) were cultured and treated by recombinant adenoviruses as described in EXAMPLE 10. Rat insulin 1 gene expression was detected in reverse transcribed total RNA samples as described in EXAMPLE 2, using primers and RT-PCR conditions as described in Table 1.

The data demonstrate that ectopic PDX-1 expression in primary culture of fetal hepatocytes in-vitro induces the expression of the endogenous, otherwise silent insulin gene expression (FIG. 6).

EXAMPLE 13

Ectopic PDX-1 Expression in Liver Cells Induces an Intracellular Compartment Characteristic of Endocrine and Neuroendocrine Cells which Allows the Retention of the Produced Hormones, and its Regulated Secretion Mice were treated with either Ad-CMVhIns or AdCMVPDX-1 as described in EXAMPLE 2. Treatment resulted in a three-fold increase serum IRI demonstrating human insulin production by liver cells (FIG. 1). Cells positive for the insulin protein by immunocytochemistry were detected only in AdCMVPDX-treatment. Moreover, HPLC analysis of liver extracts detected only trace levels of IRI in liver extracts all of it unprocessed in the Ad-CMVhIns treated mice compared to 25 fold increase in the AdCMVPDX-1 treated mice. Furthermore, 59% of the insulin produced in AdCMVPDX-1 treated mice was processed. In addition, only livers treated by AdCMVPDX-1 exhibited the induction of the prohormone processing enzyme PC1/3 which is characteristic only to cells capable of regulated pathway for insulin processing storage and regulated secretion. These data demonstrate that PDX induces the regulated secretion of insulin in liver cells

EXAMPLE 14

Identification of Nucleic Acids the Expression of which is Modulated by PDX

Nucleic acids modulated by PDX are identified by ectopic PDX expression. Nucleic acids that are not expressed in control treated extra-pancreatic islet tissue, as compared to pancreatic tissue are the nucleic acids modulated by PDX. These nucleic acids so identified are used as therapeutic compounds to treat pancreatic associated disorders.

Identification of the target genes is performed by either subtractive libraries, commercially available microarray Chips (Incyte, or Affimetrix), or membrane hybridizations (CLONTECH. Atlas™ expression arrays, or Multiple Tissue Northern (MTN®) Blots). RNA isolation from treated tissues, its purification, and cDNA probe synthesis is performed according to manufacturer instructions.

The genes which are expressed in the PDX treated non-pancreatic islet tissue and are also present in pancreatic islets probed membranes or chips, but not in control treated non-pancreatic islet tissue, are the direct and non-direct PDX target genes, which represent the islet cells characteristic profile of gene expression. Discrimination between direct or indirect is elucidated by candidate target gene promoter analysis by electromobility shift assay (EMSA) as in FIG. 7, and promoter footprinting (as described in Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

EXAMPLE 15

Figure 7:
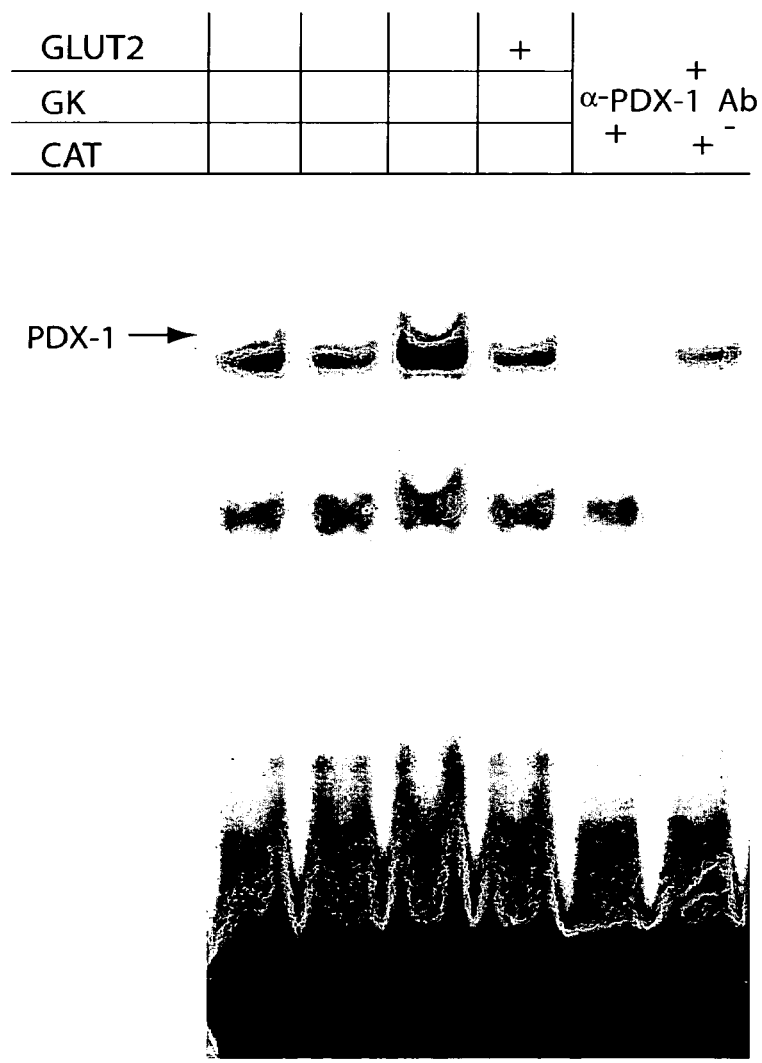
FIG. 7 is an illustration demonstrating the effect of effect of glucose on PDX-1 activation, manifested by its increased binding capacity to the insulin promoter. GLUT-2 and GK expression promote this activation by allowing glucose entry and metabolism. RIN-38 cells of intermediate passage were infected by AdCMV-GLUT2 or AdCMV-GK (lanes 4-6) or were not treated (lanes 1-3). 24 hours after viral treatment all cells were incubated in 0.2, 5 and 15 mM glucose.

Inducing Regulated Expression of a Desired Ectopically Expressed Gene in Host Tissue This EXAMPLE illustrates the induction of regulated expression of any reporter, in addition to insulin. When PDX activates the insulin promoter in non pancreatic islet tissue, and mediates its glucose and growth factors sensing ability, than, any additional promoter will be similarly regulated by glucose and growth factors. Thus, this invention can be utilized to nutritionally and hormonally regulate expression of numerous secreted/or non secreted factors such as, for example, glucagon, growth hormone, steroid hormones which are driven by the insulin promoter thus controlling their transcription, and regulated secretion, from an otherwise non-endocrine tissue. (FIG. 7.)

EXAMPLE 16

Identification of PDX Location in the Hierarchy of B or Islet Cell Specific Transcription Factors This EXAMPLE illustrates the identification of the PDX location in the hierarchy of β-cell or islet cell specific transcription factors. Every transcription factor expressed in pancreatic islets but is not induced by ectopic PDX-1 expression in liver, could cooperate with PDX for the induction of a more comprehensive, complete or close to complete β-cell phenotype in non-endocrine-pancreatic tissue, such as liver. The detection of induced expression of islet cell specific transcription factors in liver is performed as in EXAMPLE 2, using the appropriate primers and conditions the example of which is elaborated in Table 1.

An additional method to analyze the activity of transcription factors is performed by footprinting, and by Electro-Mobility Shift Assays (EMSA):

Nuclear extracts (3-4 µg of protein) were incubated on ice for 10 minutes in DNA binding mixture containing 10% Glycerol, 15 mM Hepes (pH 7.9), 150 mM KCl, 5 mM DTT and 0.3 µg of poly dIdC, poly dAdT (SIGMA St-Louis Mo.). After the first incubation, approximately 0.2 ng of the probe was added for an additional 25 minutes incubation on ice. The binding reaction was analyzed on a native 4% polyacrylamide gel.

Oligonucleotides (Probes)

Synthetic double-stranded oligonucleotides are end-labeled with [$\alpha^{32}$P]ATP using the Klenow fragment of DNA polymerase. The sequences of oligonucleotides A3/A4 which is an example for PDX-1 binding site (one of them) on the insulin promoter 5'GATCTGCC CCTTGT-TAATAATCTAATG 3' (SEQ ID NO:24). The sequence for A1 (additional PDX-1 binding site on insulin promoter) is 5' GATCCGCCCTTAATGGGCCAAACGGCA-3' (SEQ ID NO:25). The labeled oligos are used as probes for electromobility shift assays, as described in FIG. 7. The identity of PDX-1 is double estimated by supershift using a specific antibody which prevents the PDX-1 binding to its cognate locus on the promoter, or that increases the molecular weight of the complex separated on PAGE (antibody+pdx-1+probe) compared to that which includes only pdx-1+labeled probe (last two lanes in FIG. 7).

EXAMPLE 17

Figure 8:
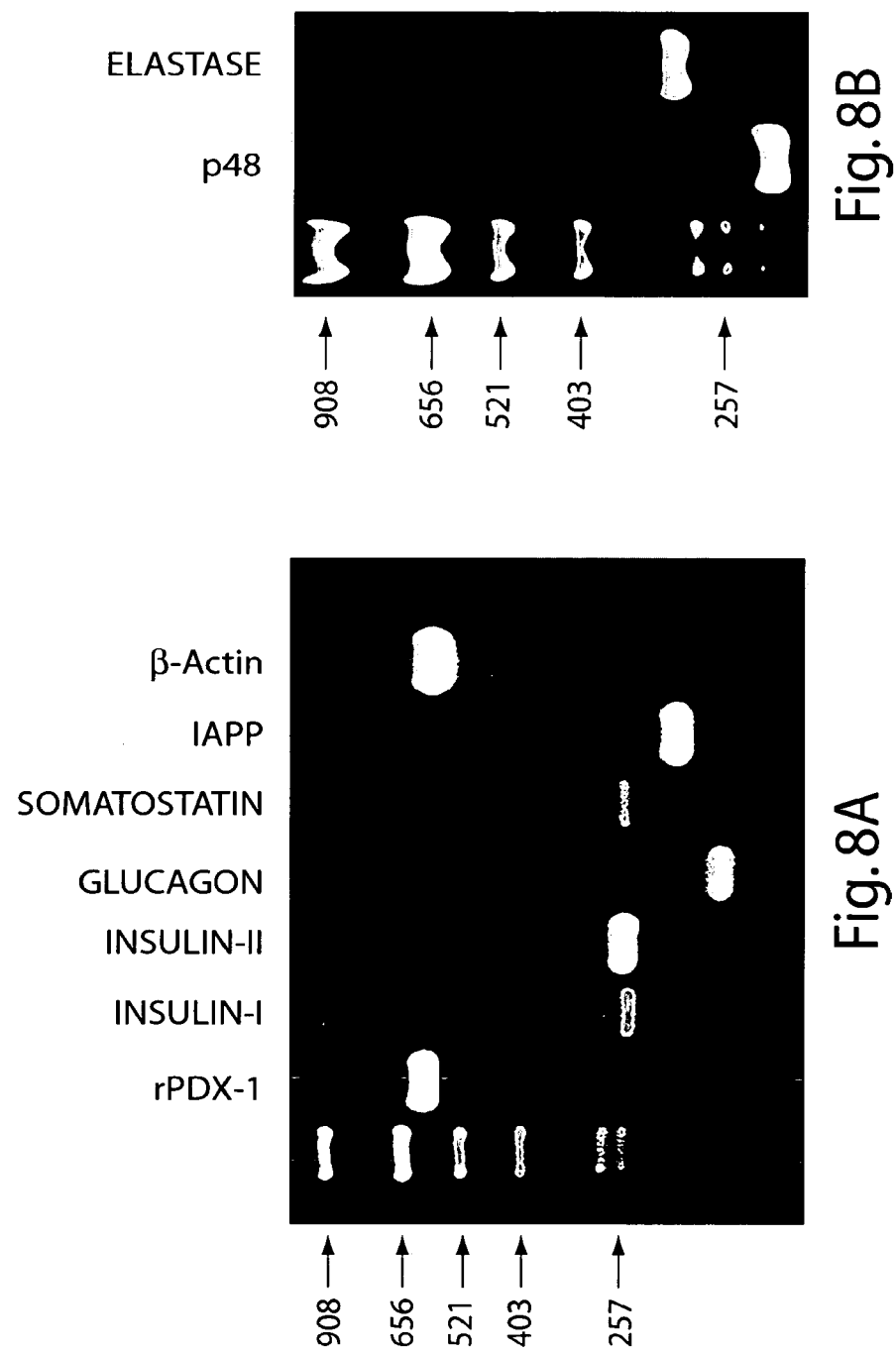
FIG. 8A is a photograph of RT-PCR analysis showing ectopic PDX-1 expression induces an endocrine repertoire of pancreatic gene expression in mature liver in-vivo.
FIG. 8B is a photograph of RT-PCR analysis showing ectopic PDX-1 expression induces an exocrine repertoire of pancreatic gene expression in mature liver in-vivo.

Ectopic PDX-1 Expression Induces Pancreatic Endocrine and Exocrine Markers in the Liver Ectopic PDX-1 expression in mature liver in-vivo activates a wide repertoire of pancreatic genes. Both endocrine and exocrine markers including the exocrine pancreas transcription factor p48 were uniquely expressed in response to ectopic PDX-1 expression in liver (FIG. 8). Control treated mice were mostly negative to pancreatic gene expression. While insulin gene expression was induced in close to 100% of mice treated by ectopic PDX-1, it was expressed at very low levels that were not translated into protein also in 20% of the control treated mice.

In the developing pancreas PDX-1 serves as an early molecular marker that temporally correlates with pancreatic commitment. This data demonstrates that that PDX-1 recapitulates its role in pancreas organogenesis, in a mature fully differentiated tissue, such as liver.

EXAMPLE 18

PDX-1 Triggers a Long-Lasting Process of Liver to Pancreas Developmental Shift

Insulin, glucagon, and somatostatin gene expression and protein production for six months after the initial, single adenovirus mediated PDX-1 administration to mice livers in-vivo was assessed.

Eight to nine weeks old mice were treated by systemic injection of Ad-CMV-PDX-1, a recombinant adenovirus that carries the rat PDX-1 gene (STF-1) under the control of the CMV promoter. Pancreatic gene expression in liver was analyzed in comparison to age-matched control mice (treated by either Ad-CMV-β-Galactosidase or untreated).

Figure 9:
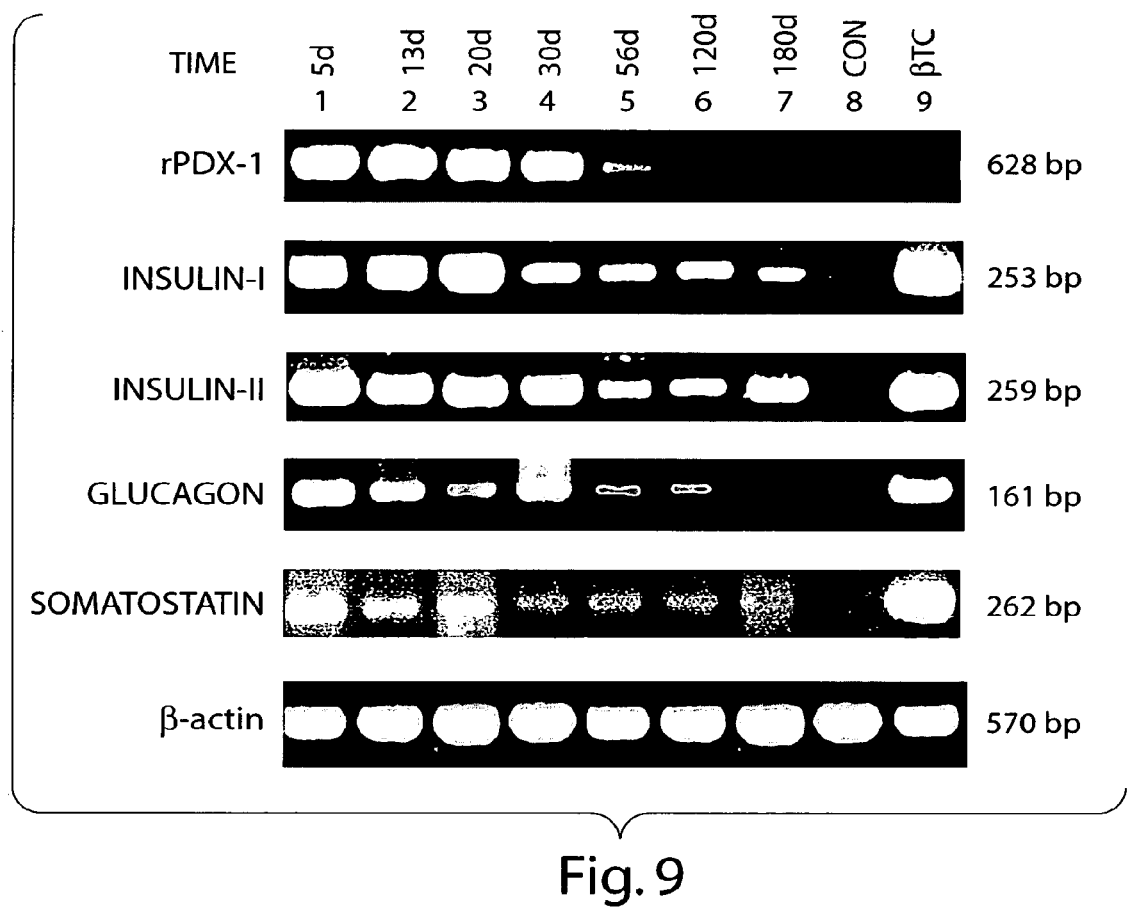
FIG. 9 is a photograph of RT-PCR analysis of pancreatic gene expression in PDX-1 treated livers as a function of time after one single administration of Ad-CMV-PDX-1, in-vivo.
Figure 10A:
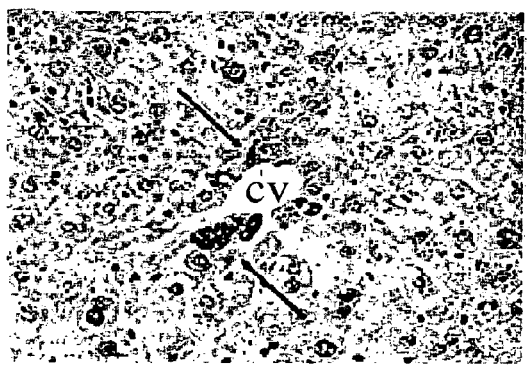
FIG. 10 are a series of photographs showing insulin and glucagon positive cells are located in the proximity of central veins (cv) four to six months after treatment. Panel A Insulin; Panel B glucagon 120 days; Panel C Insulin positive cells 180 days after Ad-CMV-PDX-1 administration; Panel D control.
Figure 10B:
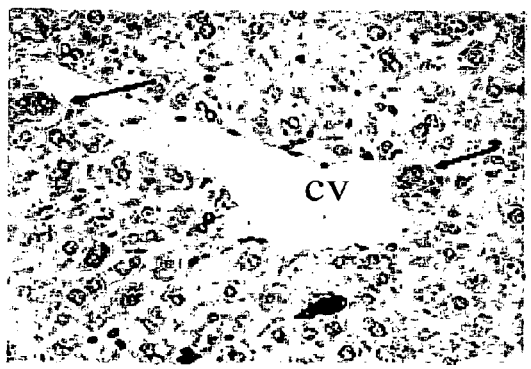
Figure 10C:
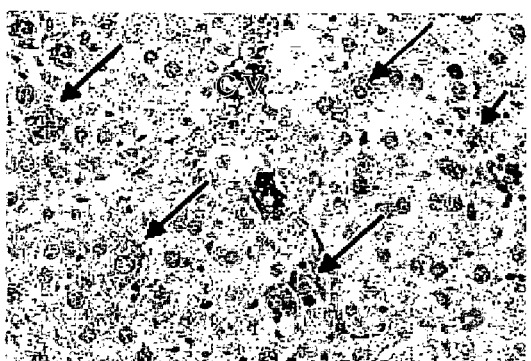
Figure 10D:
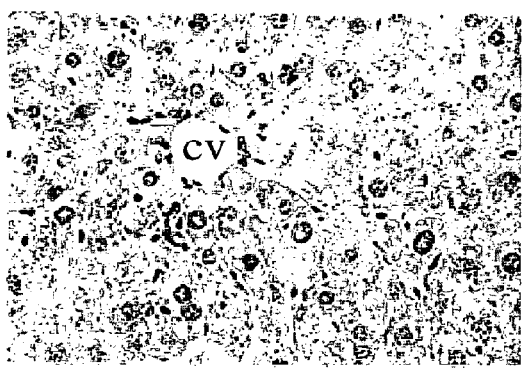
Figure 11A:
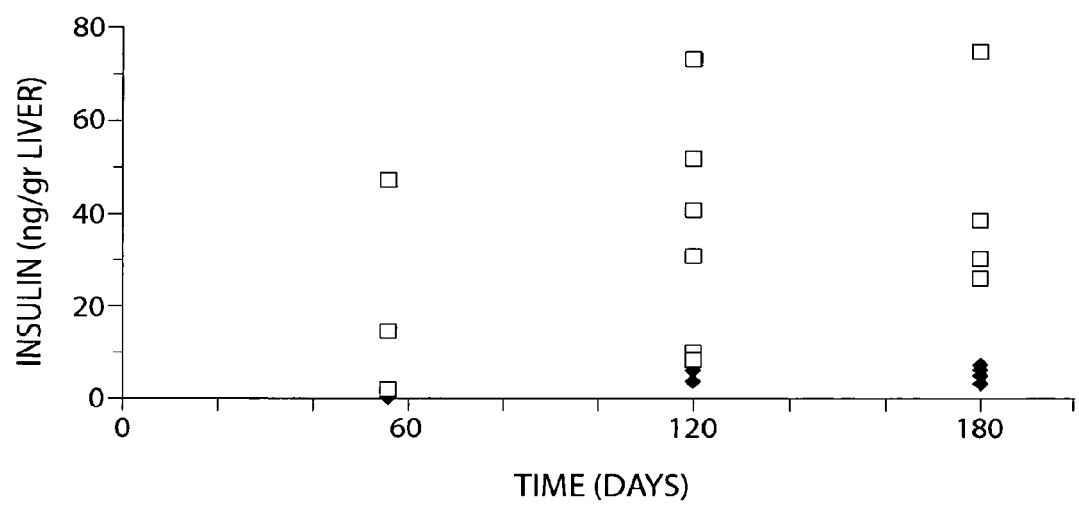
FIG. 11A is a scatter plot showing hepatic insulin content in individual mice as a function of time after systemic Ad-CMV-PDX-1 administration: at 56 days (PDX-1 treated, n=3, control, n=6), 120 days (PDX-1 treated, n=7, control, n=3) and 180 days (PDX-1 treated, n=4, control, n=5). Hepatic IRI content in PDX-1 treated (□) or control (♦) mice are presented separately for each individual mouse.
Figure 11B:
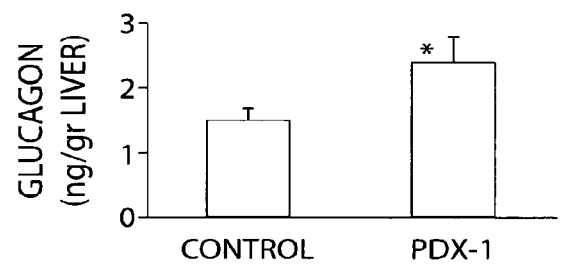
FIG. 11B is a bar chart showing hepatic glucagon content (PDX-1 treated, n=10, control, n=10) in Ad-CMV-PDX-1 treated mice.
Figure 11C:
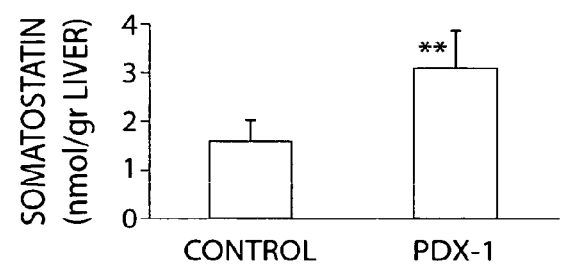
FIG. 11C is a bar showing hepatic somatostatin (PDX-1 treated, n=9, control, n=7) in Ad-CMV-PDX-1 treated mice.

Despite the expected transient PDX-1 expression achieved by adenovirus-mediated delivery of the gene to liver (expression of recombinant PDX-1 wanes between 30 and 56 days after viral injection), expression of insulin and somatostatin persisted for 6 months, at both the mRNA (FIG. 9) and protein levels (FIG. 11). Glucagon gene expression was evident during the first four months (FIGS. 9 & 10). Importantly, insulin I and insulin II genes expression was evident in 80-100% of PDX-1 treated mice even six-eight months after initial PDX-1 treatment.

The temporal differences between insulin and glucagon gene expression could reflect a unique phenomenon that characterizes pancreas organogenesis in mature liver, and suggests a more stable transconversion toward the β and δ cell phenotype. Glucagon gene is not a direct PDX-1 target gene, and its persistent expression in liver suggests that PDX-1 is functioning as a differentiation factor in this organ.

EXAMPLE 19

Quantitative Analysis of Insulin, Glucagon and Somatostatin Hormones Production in PDX-1 Treated Livers Immunohistochemical analysis (FIG. 10) localizes the insulin producing cells mainly in the proximity of central veins even four to six months after PDX-1 ectopic gene delivery (FIGS. 10A & 10C). Although glucagon positive cells are also localized in the proximity of central veins (FIG. 10B), immunohistochemical analysis of these two hormones performed on sequential slides suggest that these hormones do not co-localize within the same cell. Liver cells present in areas close to the central vein in liver are known to correspond to mature cells.

Quantitative analysis of hepatic insulin stored in liver of PDX-1 treated mice indicates that even four to six months after treatment, hepatic insulin content is about 30-75 ng/g tissue, compared to 1-9 ng/g tissue in age-matched control livers (FIG. 11A). A significant two-fold increase in hepatic pro/glucagon and somatostatin content was observed up to at least four months after initial Ad-CMV-PDX-1 administration (FIGS. 11 B & C). The substantial differences in hepatic content of insulin as compared to that of the other two pancreatic hormones following PDX-1 treatment may resemble the ratio of these hormones in the pancreas. Despite hepatic insulin production, serum insulin and glucose levels in PDX-1 treated mice, bearing normal pancreatic function were normal throughout the duration of the experiment (insulin: 1.0±0.5 vs. 0.9±0.4 ng/ml, and glucagon: 0.16±0.08 vs. 0.12±0.05 ng/ml in PDX-1 treated compared to controls, respectively).

The persistent production of pancreatic hormones in liver suggests that ectopic PDX-1 triggers a cascade of events that does not require the continuous presence of the PDX-1 transgene.

EXAMPLE 20

Ectopic PDX-1 Triggers the Expression of the Endogenous, Otherwise Silent PDX-1 Gene in Liver To evaluate the sustained developmental shift in liver, triggered by the transient ectopic PDX-1 expression, whether the transgene induces the expression of otherwise silent pancreatic transcription factors was analyzed.

To analyze the induction of the endogenous and otherwise silent PDX-1 gene in liver by the ectopic gene, mice were treated by systemic delivery of recombinant adenovirus that directs expression of the rat PDX-1 homologue, and used specific oligonucleotide primers to distinguish between the ectopic PDX-1 transgene (rat) mRNA (cDNA) and the endogenous mouse mRNA, by RT-PCR.

Figure 12A:
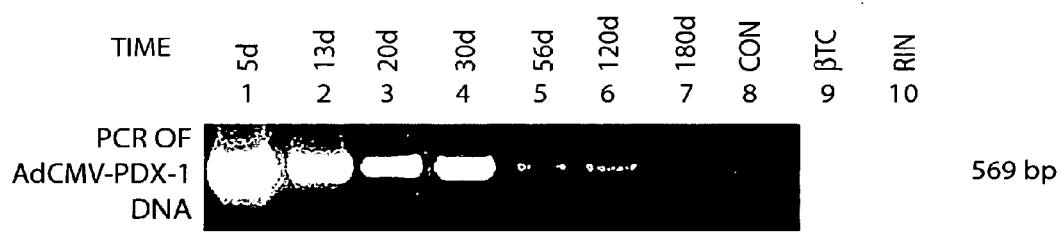
FIG. 12A is a photograph showing PCR of ectopic rat PDX-1 cDNA attached to CMV promoter, which reflects of the presence of viral Ad-CMV-PDX-1 DNA in treated liver as a function of time (in days) after adenoviral administration to mice in-vivo.

PCR analysis of DNA samples isolated from liver of Ad-CMV-PDX-1 treated mice confirms that the virally encoded transgene disappears between 30 and 56 days after adenovirus injection (FIG. 12A).

Figure 12B:
FIG. 12 B is a photograph showing RT-PCR analysis of rat PDX-1 (rPDX-1), mouse PDX-1 (mPDX-1) and β-actin gene expression in liver, as a function of time after Ad-CMV-PDX-1 administration, in-vivo.
FIG. 12C is a bar chart showing quantitation of ectopic (rat) vs. endogenous (mouse) PDX-1 expression as a function of time after initial Ad-CMV-PDX-1 treatment using real time PCR. Mouse PDX-1 (striped columns) and rat PDX-1 (solid black columns).

FIG. 12B demonstrates that the ectopic rat PDX-1 expression parallels the observed presence of delivered viral DNA in liver and also extinguishes after one month (FIG. 12A). The only homologue of PDX-1 expressed in treated livers for the whole duration of the experiment is the endogenous and otherwise silent mouse homologue (FIG. 12B). Endogenous PDX-1 expression is exclusive to mice that received the rat PDX-1 transgene, and was evident in 75% of ectopic PDX-1 treated mice (21 out of 28 mice), and in none of the 25 control treated livers analyzed. Using real time PCR the identity and quantitated the relative levels of mouse versus rat PDX-1 gene expression in liver was analyzed as a function of time after the initial treatment, using identical conditions (but different primers) and normalized it to β-actin within the same samples.

Figure 12C:
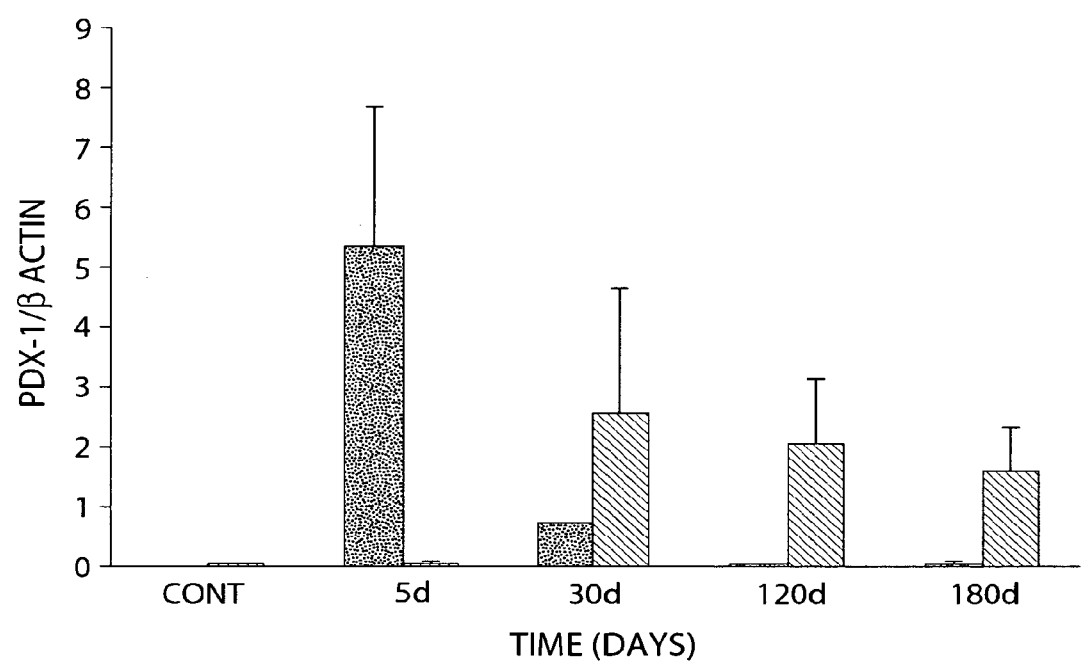

As shown in FIG. 12C, the mRNA encoding the ectopic rat PDX-1 is maximal at 5 days, drops by 85% at day 30 and disappears thereafter. By contrast, the endogenous mouse PDX-1 is expressed at substantial levels for the whole duration of the experiment. These data taken together, suggest an auto-induction of the endogenous and otherwise silent PDX-1 in liver, which suggests a mechanistic explanation for the long lasting mode of liver to pancreas transconversion process.

EXAMPLE 21

Insulin Produced in Liver in Response to PDX-1 Transgene Expression is Functional and Prevents STZ-Induced Hyperglycemia In order to determine whether PDX-1 gene delivery induces long-lasting production of biologically active insulin, whether it provides protection against STZ induced diabetes was analyzed. Eight months after the initial Ad-CMV-PDX-1 treatment, mice were treated by 220 mg/kg STZ, and the incidences of hyperglycemia were compared to these in age matched controls. Sixty percent of the control Balb/c mice developed hyperglycemia (6 out of 10), within 3-5 days of STZ injection. By contrast, only one out of five PDX-1 treated mice developed hyperglycemia in response to STZ treatment (20%), despite the fact that they were analyzed eight months after Ad-CMV-PDX-1 treatment.

Figure 13:
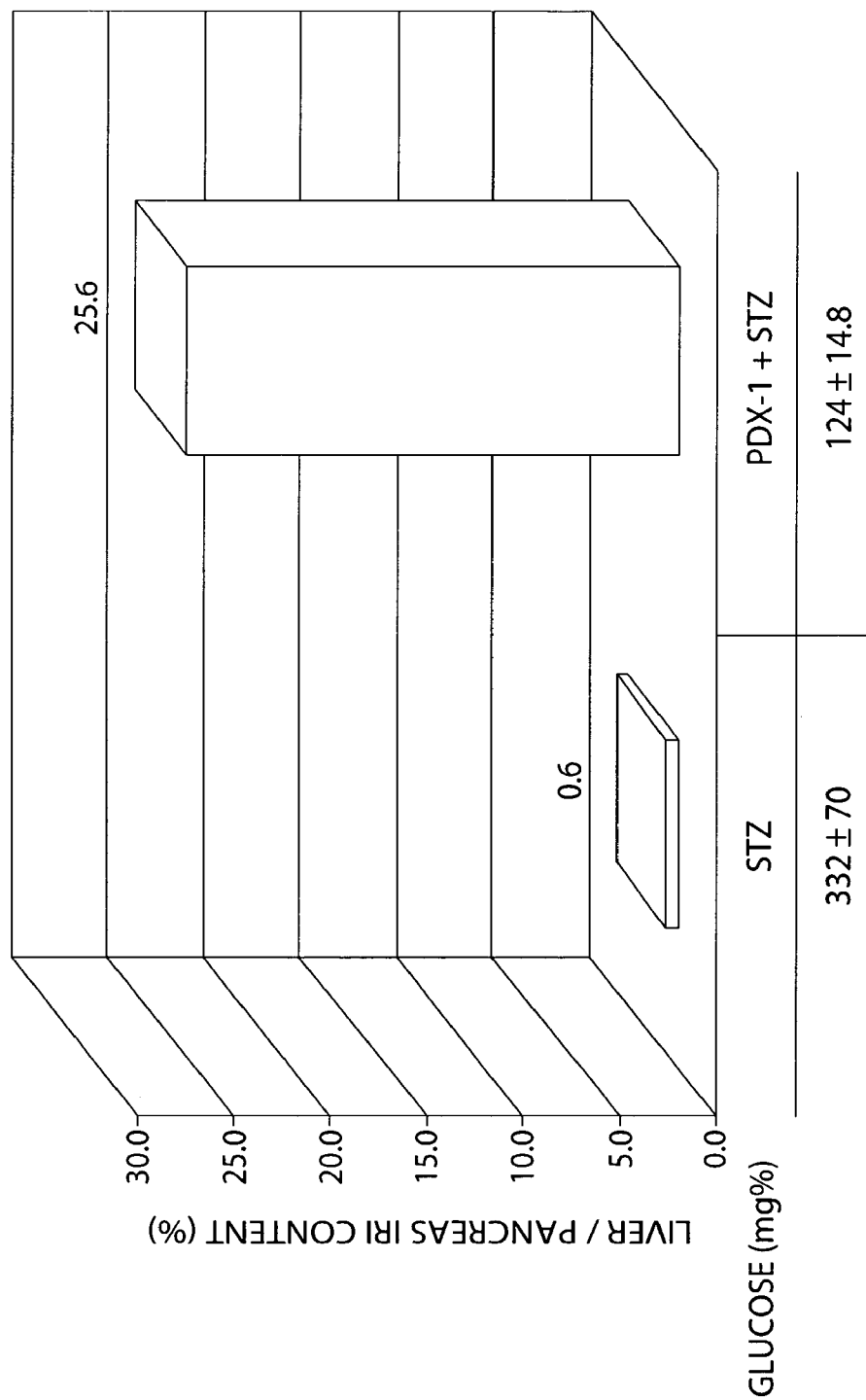
FIG. 13 is bar chart showing hepatic insulin production protects mice from STZ induced hyperglycemia, eight months after the initial Ad-CMV-PDX-1 treatment, and that transdifferentiated insulin producing cells in liver are resistant to STZ.
Figure 14:
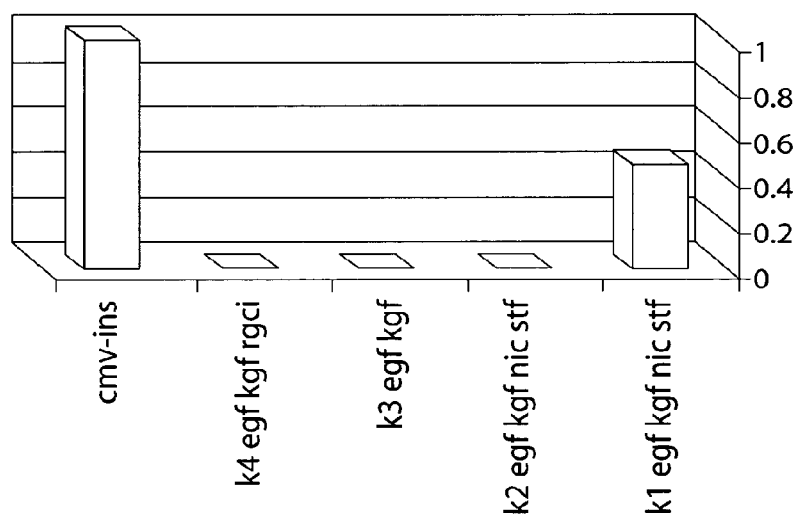
FIG. 14 is a bar chart depicting insulin gene expression in human keratinocytes, wherein PDX-1 treatment works in a dose dependent manner: 100 but not 10 moi (multiplicity of infection) were capable of activating insulin gene expression.

Immunohistochemical studies and quantitation of insulin content levels by RIA revealed that in response to STZ treatment, pancreatic β-cells were mostly destroyed and pancreatic insulin content in both control diabetic mice and importantly in PDX-1 treated mice (that remained normoglycemic) dropped by 95±1%. By contrast, hepatic immunoreactive insulin (IRI) content in PDX-1 treated mice was forty fold increased compared to control diabetic mice that were not treated by PDX-1 (FIG. 13). In healthy mice hepatic insulin is only about 1% of that produced in pancreas However, in response to STZ treatment, hepatic insulin production becomes 25.6% of the amount of immunoreactive insulin produced in STZ treated pancreas of the same mice.

These results demonstrate that the PDX-1 induced developmental shift is both long lasting and functional, the relatively modest IRI levels contributed by the liver, suggests that insulin produced in liver protects against STZ induced hyperglycemia also by efficient regulation of the balance between hepatic glucose production and glucose disposal. Importantly, it also suggests that developmentally shifted cells in liver resist β-cell specific toxins.

Importantly, despite the ongoing local insulin production in liver even six-eight month after initial viral infection, hepatic functions were not perturbed (Table 4a). Transient alterations in hepatic functions occurred in response to adenovirus administration, however, hepatic function returned back to normal levels within one-two months. Moreover, serum amylase levels were not increased at all time points despite endogenous PDX-1 and pancreatic hormones expression (table 4b). The rate of weight increase of PDX-1 treated mice was similar to that in age matched control mice.

TABLE 4

Hepatic function in Ad-CMV-PDX-1 treated mice

|  | ALB (gr/dl) | AST (IU/L) | ALT (IU/L) | T. bil (mg/dl) |
| --- | --- | --- | --- | --- |
| Control (10) | 2.5 ± 0.05 | 82 ± 5.75 | 36.6 ± 3.2 | 0.1 |
| PDX 5 days (5) | 2.5* | 121* | 102* | 0.1* |
| PDX 20 days (5) | 2.5 ± 0.05 | 111 ± 21 | 73 ± 10 | 0.1 |
| PDX 60 days (12) | 2.5 ± 0.05 | 101 ± 31 | 53.6 ± 13.6 | 0.1 |
| PDX 120 days (3) | 2.5 | 81.6 ± 29 | 29 ± 2 | 0.1 |
| PDX 180 days (3) | 2.5 ± 0.05 | 61 ± 7 | 21 ± 2 | 0.1 |

Blood biochemistry measurements (mean ± SEM) of mice after PDX administration. ALB: albumin; AST: aspartate aminotransferase; ALT: alanine aminotransferase; T. bil: total bilirubin. Data are mean ± SEM;
*pooled samples, numbers of mice analyzed are in parenthesis.

TABLE 4b

Serum Amylase levels in PDX-1 treated mice.

| Time after adenoviruses Administration | Amylase(IU/L) | |
| --- | --- | --- |
|  | Control | PDX-1 |
| 5 days | 1850 (3) | 1709 (2) |
| 60 days | 1909 (2) | 1876 (2) |
| 120 days | 2240 (3) | 1744 (7) |
| 180 days | 1978 (4) | 2477 (4) |
| 240 days | 2298 (6) | 2343 (4) |
| 280 days | 2634 (3) | 2570 (4) |

EXAMPLE 22

PDX-1 and Growth Factors Induced Transdifferentiation in Primary Culture of Human Keratinocytes Cell Culture Keratinocyte cultures were initiated from small biopsy specimens (2-4 cm$^2$) of split-thickness skin. After overnight (ON) incubation in trypsin-EDTA the epidermis was separated and epithelium disaggregated in trypsin-EDTA to form single cells suspension. The cell suspension was cultured in Keratinocyte Medium (Nature 265: 421-4, 1977), and the cell suspension was attached to falcon culture plates and used at passages 2-5. When cells reached 70% confluency, they were treated by the indicated treatments described below for 48-96 hours.

Gene Expression

Gene expression analyses were performed using Taqman real time PCR (ABI).

| Cell Treatment | |
| --- | --- |
| K1: EGF + KGF + NIC + PDX-1(100 moi) | K2: EGF + KGF + NIC + PDX-1(10 moi) |
| K3: EGF + KGF | K4: EGF + KGF + RGCI |

At all treatments: EGF, KGF are 20 ng/ml; NIC: 10 ng/ml
Controls

The control cells were treated with a non-relevant, Ad-CMV-Hinsulin, recombinant adenovirus that carried the expression of the human insulin gene under the control of the CMV promoter. RGCI is a bifunctional recombinant adenovirus construct—Ad-CMV-PDX-1-RIP-GFP that identified cells that had undergone PDX-1 mediated transdifferentiation toward insulin gene expression. PDX-1 expression in this virus was driven by CMV promoter, whereas GFP expression was driven by the tissue specific promoter for insulin (RIP).

Results

Figure 15:
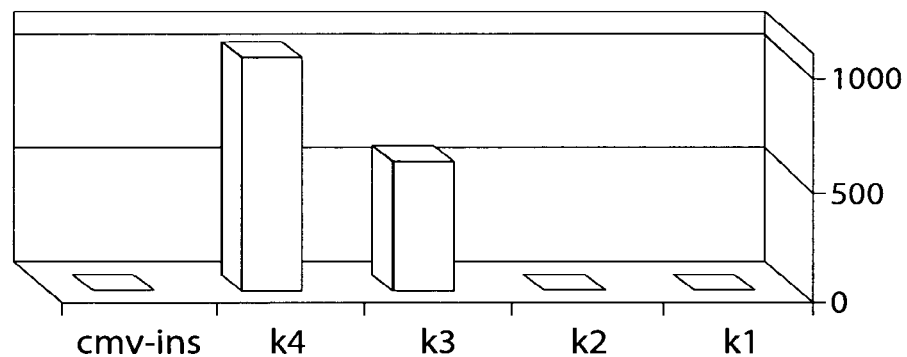
FIG. 15. is a bar chart depicting glucagon gene expression in human keratinocytes.
Figure 16:
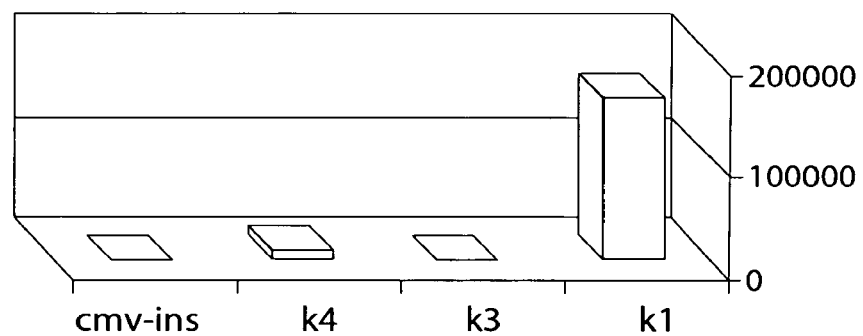
FIG. 16. is a bar chart depicting somatostatin gene expression in human keratinocytes.

In the treatments K1-K4, the endogenous otherwise silent pancreatic genes were expressed in keratinocytes. Interestingly, glucagon gene expression was induced by low levels of PDX-1 (K4) and importantly, by EGF+KGF treatment alone, with no need for ectopic PDX-1. (FIG. 15).

EXAMPLE 23

PDX-1 Activates the Insulin Promoter in Human Liver Cells

Figure 17A:
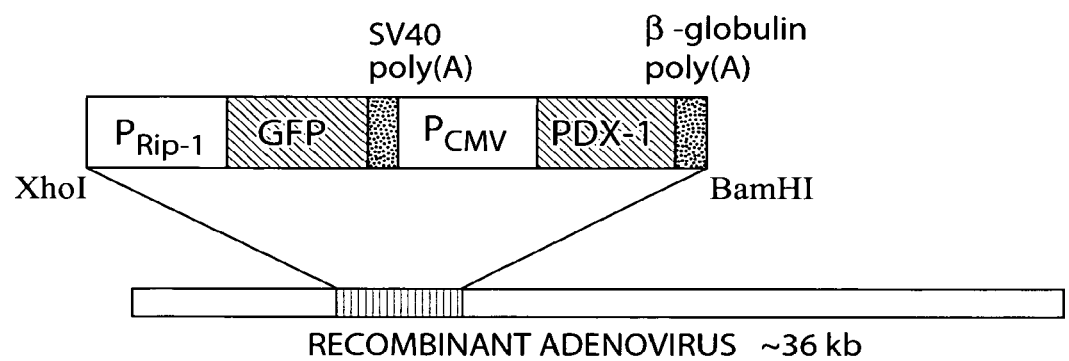
FIG. 17A is an illustration depicting an Ad-RIP-GFP-CMV-PDX-1 construct, this construct allows identifying cells that ectopic PDX-1 expression induces the activation of ectopic insulin promoter.
Figure 17B:
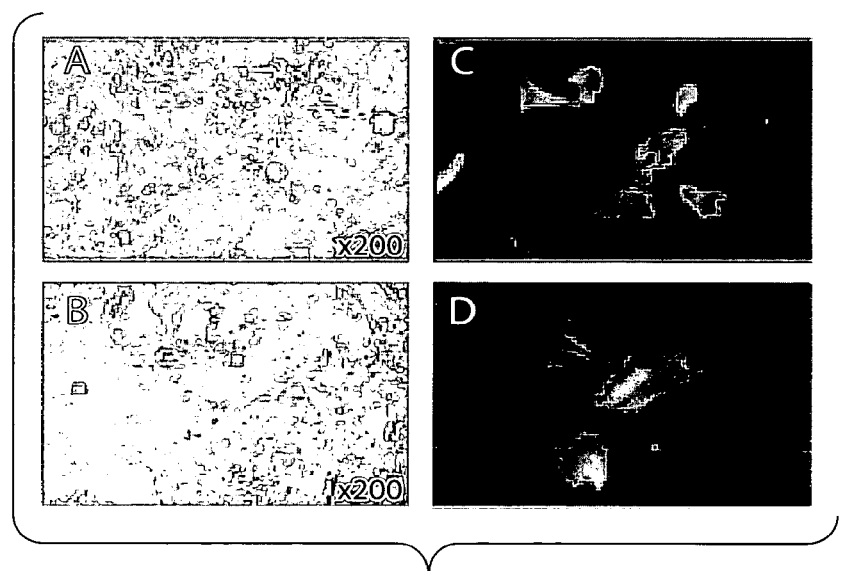
FIG. 17 B is a series photographs showing phase contrast morphology (A, C), and green fluorescence (B, D) of adult liver cells at passage 2 (A, B) and at passage 8 (C, D) infected by Ad-RIP-GFP-CMV-PDX-1 (magnification×200).
FIG. 17C is a bar chart showing the number of adult (black bars) and fetal (grey bars) liver cells that exhibit insulin promoter activation manifested by green fluorescence as a function of the passage number in-vitro (n≥20 random fields were counted at each passage).
FIG. 17D is a bar chart showing the transdifferentiation potential (lined bar) of adult liver cells is calculated as the percent of cells that exhibit the insulin promoter activation (Ad-RIP-GFP-CMV-PDX-1, black bar) divided by the total cell infection capacity, exhibited by fluorescing cells subsequent to Ad-CMV-GFP infection (grey bar, n>10), as a function of the passage number.
Figure 17C:
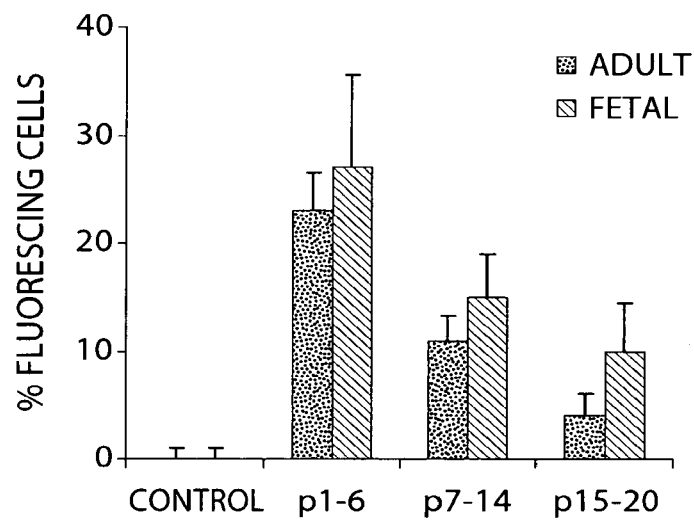

Human liver cells were isolated from both adult and fetal tissues. The cells exhibited a heterogeneous phenotype and proliferated efficiently in culture for up to 20 passages. It was analyzed whether human cells isolated from adult fully differentiated liver without any prior selection undergo a process of developmental re-direction towards pancreatic phenotype in response to ectopic PDX-1 expression. The first indication of pancreatic characteristics is the activation of the insulin promoter, which otherwise is inactive in liver. Cells were treated by the bi-functional recombinant adenovirus: Ad-RIP-GFP-CMV-PDX-1 which carries the expression of PDX-1 under the control of the heterologous CMV promoter, while the insulin promoter controls GFP expression (FIG. 17a), thereby Pdx-1 'responding' cells were identified by green fluorescence (FIG. 17b). The total capacity of adult human liver cells to be infected by recombinant adenovirus was examined using Ad-CMV-GFP infection; 40±7% of adult liver cells at passages 1-6 expressed green fluorescence in response to Ad-CMV-GFP infection. Surprisingly, about half of these cells (23±3.5%) responded to ectopic PDX-1 expression by activation of the pancreatic promoter (FIG. 17b), as was also determined by FACS analysis (data not presented). In order to determine whether the partial response is influenced and limited by the differentiation state of the adult liver cells, PDX-1 capacity to induce a developmental redirection of fetal human liver cells, being less differentiated and possibly contain more pluripotent cells than adult human liver cells was analyzed. Indeed, 27±7.8% of fetal human liver cells in culture (isolated from 22 weeks gestation) responded to ectopic PDX-1 expression by activation of the pancreatic promoter, while their response to Ad-CMV-GFP transduction was similar to that of cells isolated from adult liver (FIG. 17c). This modest increase in number of responding cells, may suggest that the differentiation state of the cells plays only a limited role in the developmental shift process induced by PDX-1.

Figure 17D:
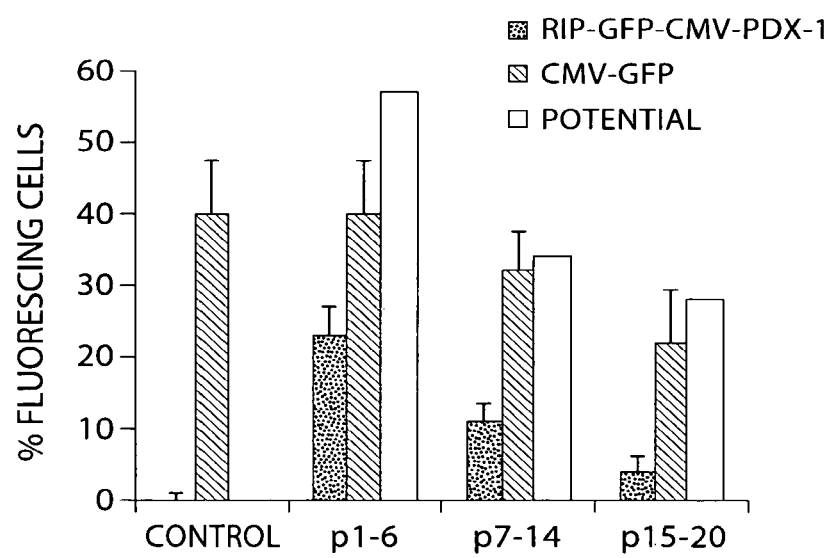

Three important observations emerge from the primary culture of human liver cells. First, both adult and fetal cells, when cultured in-vitro, proliferate efficiently for up to six months and are capable of activating the insulin promoter in response to PDX-1 treatment. However, their infection and 'transdifferentiation' capacities decrease with the increase in passage number (FIGS. 17c&d). Second, although fetal human hepatic tissue may consist a larger number of pluripotent cells than cells isolated from adult liver, they may possess similar capacities to undergo a transdifferentiation process towards pancreas (FIG. 17c). Third, the capacity to activate the insulin promoter in human liver cells that ectopically express PDX-1 does not occur in a rare population of cells, since half of the cells capable of being infected by recombinant adenovirus also activated the ectopic insulin promoter in a PDX-1 dependent manner at low passages in culture (FIG. 17d).

EXAMPLE 24

Soluble Factors Promote PDX-1 Induced Liver to Pancreas Transdifferentiation

A better indication for the extent of the transdifferentiation process is to analyze the induction of the endogenous otherwise silent pancreatic genes expression in PDX-1 treated liver cells.

Figure 18A:
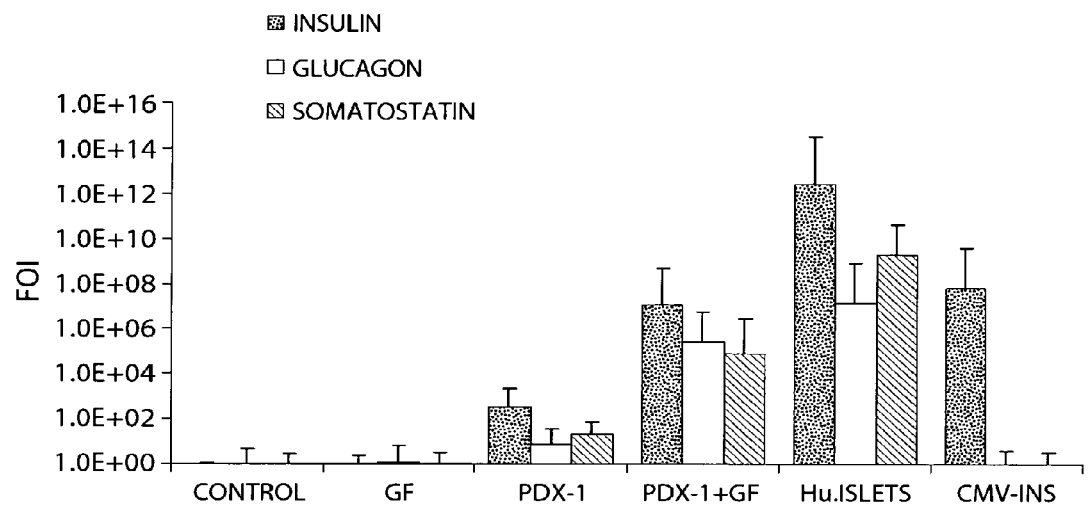
FIG. 18A is a bar chart showing pancreatic hormones gene expression in adult and fetal liver cells treated by Ad-CMV-PDX-1 with or without growth factors (GF) supplementation. Ad-CMV-hIns serves as positive control for insulin gene expression. $C_t$ (threshold cycle) values were all normalized to β-actin gene expression within the same RNA sample.

The expression of the three major pancreatic hormones genes expression was induced by PDX-1 more than two orders of magnitude, compared to control untreated liver cells (FIG. 18).

Figure 18B:
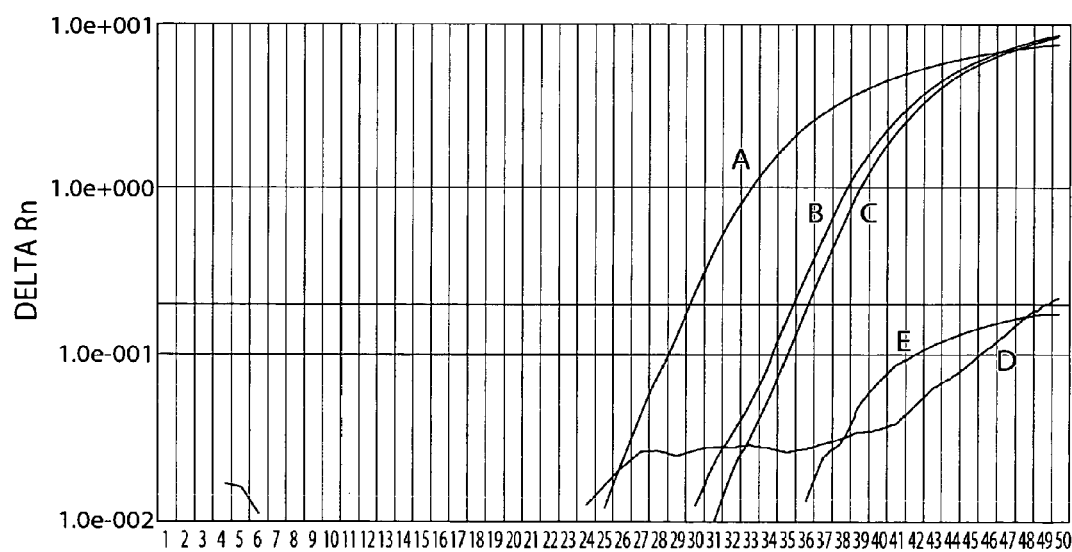
FIG. 18 B is a quantitative RT-PCR (Real-time) amplification curve of Insulin in human islets (RNA diluted 1:50, A), in Ad-CMV-PDX-1 and GF treated adult (B) and fetal (C) human liver cells, untreated adult (D) and fetal (E) liver cells (all with the same Ct-values for β-actin gene expression). The curves are presented as the ΔRn (fluorescentic units) versus the cycle number of the amplification reaction. Showing that mature liver cells are as efficient as fetal human liver cells in activating insulin gene expression in response to PDX-1

Nicotinamide and epidermal growth factor (EGF) are known to promote pancreatic endocrine differentiation of undifferentiated pancreatic cells, including that of embryonic pancreatic organ culture. Interestingly, when PDX-1 treatment was supplemented with nicotinamide and EGF (collectively called GF), pancreatic hormones gene expression was dramatically increased. Insulin gene expression in primary culture of adult liver cells was seven orders of magnitude increased compared to that in control untreated liver cells. Neither nicotinamide nor EGF alone or their combination exhibited PDX-1 independent effect on pancreatic gene expression in liver cells. These data suggest that PDX-1 is necessary to the process of liver to pancreas transdifferentiation, while the GF possess a synergistic effect on the process without being sufficient to independently induce it. Importantly, fetal and adult human liver cells exhibited similar levels of pancreatic gene expression in response to ectopic PDX-1 expression and GF treatment, as depicted by real-time PCR quantification for insulin gene expression in both cultures (FIG. 18b).

Culturing liver cells in the presence of GF for couple of weeks prior to PDX-1 treatment did not result in increased insulin gene expression compared to cells that were simultaneously treated by PDX-1 and GF. In contrast, excluding GF from pretreated cultures resulted in insulin gene expression at levels similar to that of PDX-1 alone. Taken together it is suggested that the promoting effect GF have on PDX-1 induced transdifferentiation is not due to inducing the proliferation of a rare subpopulation of cells susceptible to the process, but rather they contribute in an yet unknown fashion to possibly augment the intra-cellular signal transduction leading to the PDX-1 induced process. Similar multiplicity of infection of Ad-CMV-hIns, a recombinant adenovirus that carries the constitutive ectopic expression of human proinsulin cDNA under the control of the CMV promoter resulted in insulin gene expression at levels comparable to these in PDX-1 and GF treated cells (without inducing glucagon and somatostatin gene expression, as under PDX-1 treatment), Taking in consideration that the number of cells that express insulin when treated by Ad-CMV-hIns is twice the number of cells that express the PDX-1 induced endogenous insulin gene (since only up to 23% of the cells may undergo a transdifferentiation process, while 40% of the cells express the ectopic human insulin gene, see FIGS. 17c and 18c), suggests that the (endogenous) insulin promoter in PDX-1 treated liver cells is as active and potent as the heterologous CMV promoter.

EXAMPLE 25

PDX-1 Endows Adult Human Liver Cells with Endocrine Characteristics

Figure 19:
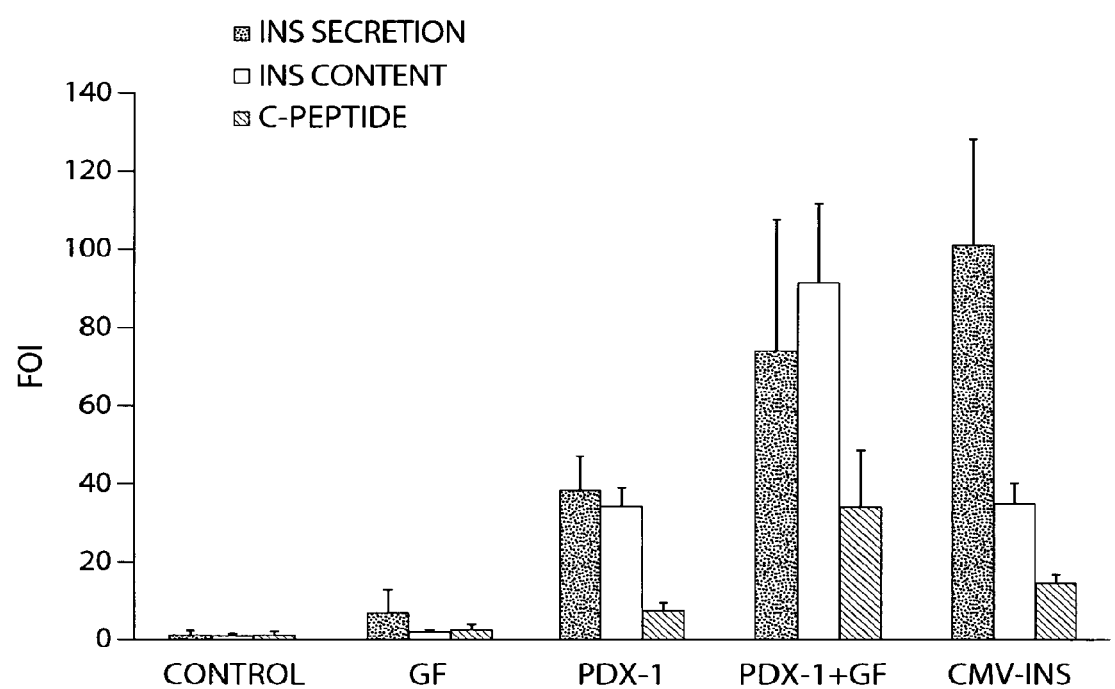
FIG. 19 is a bar chart showing insulin content, secretion and processing in adult primary liver cells that were treated by Ad-CMV-PDX-1, supplemented by growth factors and analyzed for insulin content (black bar; n≥10), insulin (lined bar; n≥25) and C-peptide (pointed bar; n≥25) secretion by static incubations for 48 hours. Ad-CMV-hIns infected cells serve as positive control for non regulated and unprocessed insulin secretion. Results indicate fold of increase (FOI) compared to untreated control liver cells.
Figure 21A:
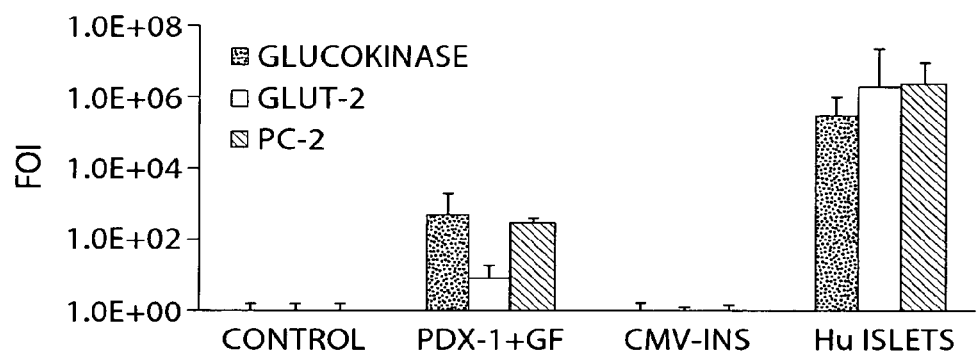
FIG. 21A is a bar chart showing the results of Quantitative RT-PCR (Real-Time) gene expression analyses performed using specific Taqman probes for the regulatory proteins Glucokinase, Glut-2 and Prohormone Convertase 2 (PC2), normalized to β-actin gene expression within the same cells, in Ad-CMV-PDX-1 and GF treated or control liver cells. Human islets serve as a positive control. Results indicate fold of increase (FOI) compared to (untreated) control liver cells (n≥10 in each experiment).

In order to analyze whether once transdifferentiated, adult human liver cells gain endocrine cells characteristics, these cells potential to store and process, the PDX-1 induced insulin was analyzed. FIG. 19 demonstrates the insulin and C-peptide secretion and the insulin content in PDX-1 treated cells. PDX-1 treatment alone resulted in 34.5±4.5 fold increase in immunoreactive insulin (IRI) content, 38.7±8.7 fold increase in IRI secretion and 7.5±2.1 fold increase in C-peptide secretion. Supplementing the culture media by GF substantially augmented the PDX-1 effect on the process; IRI content raised to 91.3±20.3 fold increase, its secretion was 74.5±33.3 fold increased and C-peptide secretion was 33.9±14.6 fold increased compared to untreated liver cells. The effect of PDX-1 on the process was compared to that of ectopic expression of human proinsulin (using the Ad-CMV-hIns recombinant adenovirus). While most of the IRI produced in cells treated by Ad-CMV-hIns was released, much of the IRI in PDX-1 treated cells is retained within the cells. The modest secretion of C-peptide upon Ad-CMV-hIns treatment could be attributed to pre-existing endopeptidases such as furin in liver cells. Importantly, the induction of prohormone convertase 2 was evident only upon PDX-1 treatment but not in Ad-CMV-hIns treated liver cells (FIG. 21a).

Figure 20A:
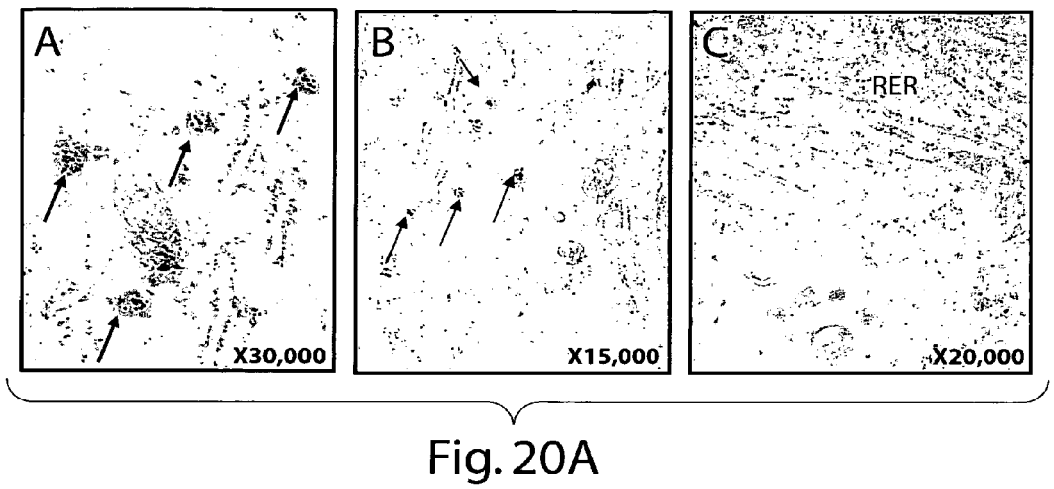
FIG. 20A is a series of photographs showing insulin secretory granules in PDX-1 treated adult human liver cells. Electron microscopy of insulin immunogold histochemistry in adult human liver cells treated with (A, B) or without (C) Ad-CMV-PDX-1 and growth factors. Arrows, immunogold particles concentrated in secretory granules which appear in PDX-1 treated liver cells.
Figure 20B:
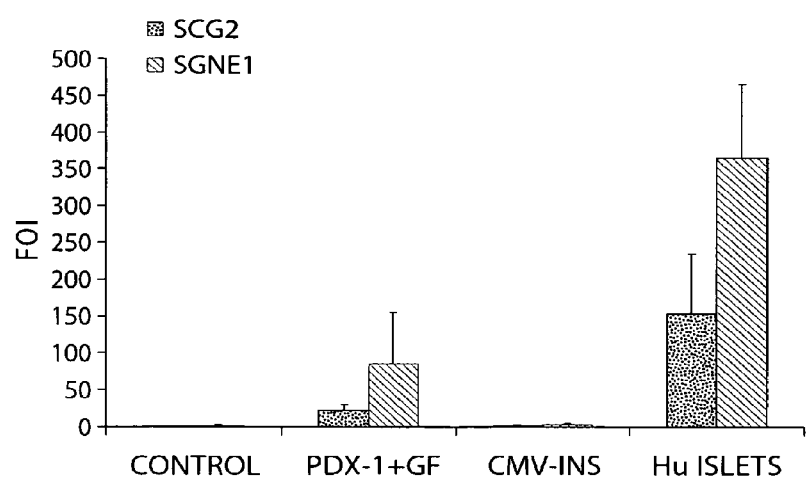
FIG. 20B is a bar chart showing the results of quantitative RT-PCR (Real-Time) gene expression analyses performed using specific Taqman probes for the specific endocrine secretory granule molecule markers Secretogrannin2 (SCG2) and Secretory Granule Neuroendocrine 1 (SGNE1), normalized to β-actin gene expression within the same cells, in Ad-CMV-PDX-1 and GF treated or untreated adult liver cells. Human islets serve as a positive control. Results indicate fold of increase (FOI) compared to that of untreated control liver cells (n≥12 in each experiment).

Electron microscopic analysis of immunogold histochemistry using antibodies against insulin revealed that the insulin is stored in secretory granules (FIG. 20a). These granules did not contain a characteristic dense core as in intact pancreatic islets in-vivo, but resembled these present in the β-cell lines that may contain a lower level of insulin storage. The endocrine phenotype was associated with the specific induction of neuroendocrine vesicles specific gene expression. Specific expression of SCG-2 (Secretogranin-2) and SGNE1 (Secretory granule neuroendocrine-1, FIG. 21b) was observed only in PDX-1 treated cells but not upon Ad-CMV-hIns treatment.

These data taken together suggest that adult human liver cells treated by PDX-1 and soluble factors undergo a wide and efficient transdifferentiation process into pancreatic hormones producing cells, that resembles many features characteristic to pancreatic endocrine cells.

EXAMPLE 26

Glucose Sensing Ability of Transdifferentiated Adult Human Liver Cells

Glucose sensing ability and the coupling between glucose sensing and insulin secretion is the hallmark of pancreatic β-cell function.

Figure 21B:
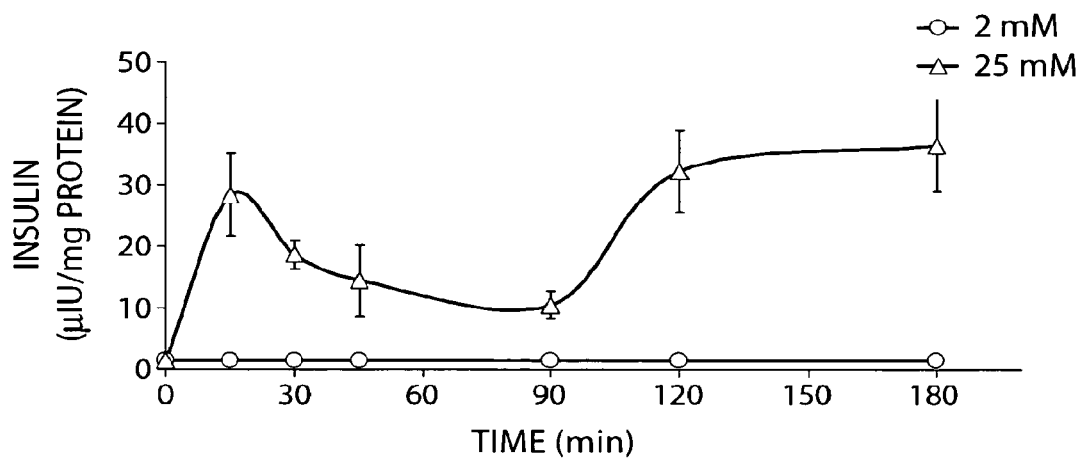
FIG. 21B is a graph depicting insulin secretion in a time course (15-180 minutes) at 2 mM (o) or 25 mM (.) glucose concentrations in PDX-1 and GF treated adult human liver cells.
Figure 21C:
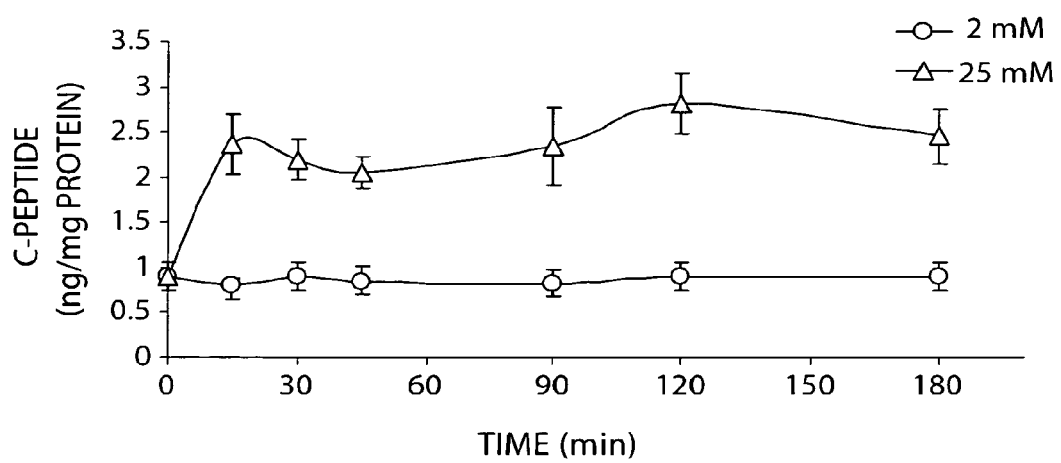
FIG. 21C is a graph depicting C-peptide secretion in a time course (15-180 minutes) at 2 mM (o) or 25 mM (.) glucose concentrations in PDX-1 and GF treated adult human liver cells.
Figure 21D:
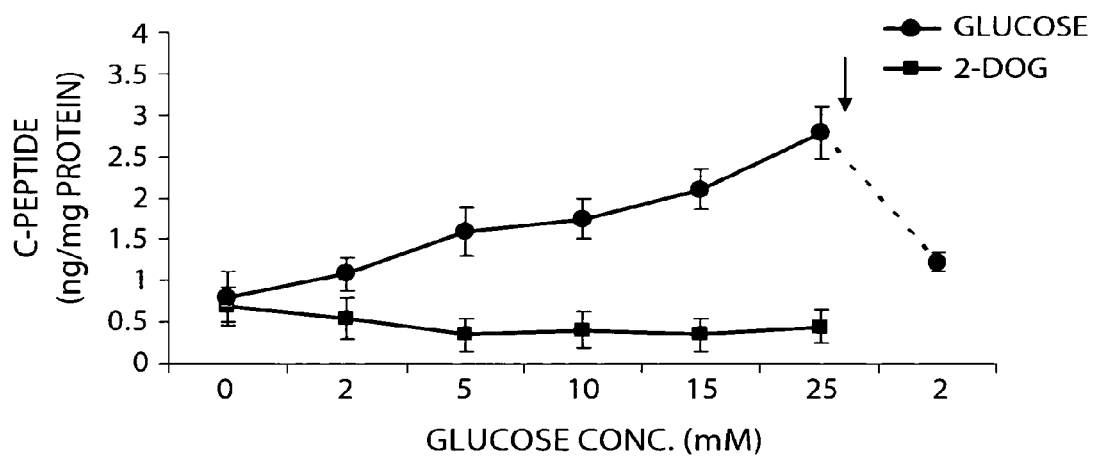
FIG. 21D is a graph depicting C-peptide dose response secretion at 0-25 mM Glucose (.) or 2-DOG (.) concentrations. The arrow and dotted line indicate exchanging the 25 mM Glucose treatment into 2 mM Glucose. (b-d): n=6 in 3 different experiments.

It was demonstrated that PDX-1 induced transdifferentiated liver cells express GLUT-2 and glucokinase (GK, FIG. 21a) genes and secrete insulin in a glucose regulated manner. Exposure of PDX-1 treated adult human liver cells to 25 mM glucose results in an immediate and profound increase in insulin secretion (FIG. 21b). Time course analysis of glucose stimulated insulin (FIG. 21b) and C-peptide (FIG. 21c) secretion, revealed similar bi-phasic dynamic characteristics as that in pancreatic β-cells, with an immediate and sharp first peak followed by a prolonged second peak of secretion. Once the glucose trigger was removed, insulin secretion immediately decreased (FIG. 21d). The decrease in extra-cellular insulin levels 60-90 minutes after the initial glucose trigger (FIG. 21b), was more profound than in C-peptide secretion (FIG. 21c) and may represent extensive uptake of the secreted insulin by liver cells in the heterogeneous culture. Glucose dose response reveals a shift to the right compared to normal pancreatic β-cells, since maximal C-peptide secretion occurs at 25 mM glucose (FIG. 21d) compared to maximal insulin secretion at 8-16 mM in normal pancreatic islets. Importantly, the coupling between the glucose sensing ability to insulin secretion occurs in transdifferentiated liver cells in the same mode as in normal pancreatic β-cells: glucose should be metabolized in order to exert its effect on insulin secretion. A non-metabolizable glucose analog; 2-deoxy-glucose (2-DOG), did not trigger C-peptide secretion in transdifferentiated liver cells (FIG. 21d). As expected, ectopic expression of human insulin driven by a constitutive promoter (Ad-CMV-hIns) did not result in glucose regulated secretion of the prohormone. These data indicate that the glucose sensing ability and its coupling to insulin secretion are a consequence of the transdifferentiation process.

EXAMPLE 27

Figure 22A:
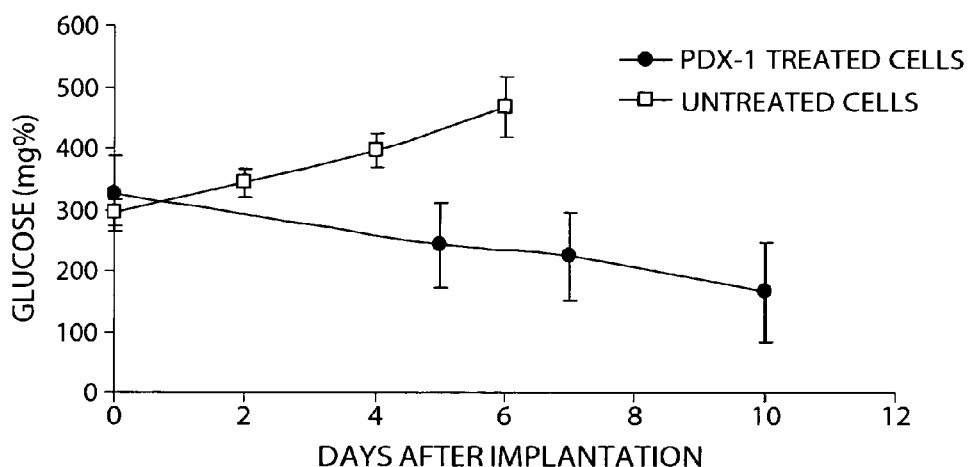
FIG. 22A is a graph showing PDX-1 treated liver cells correct hyperglycemia in SCID-NOD mice. Diabetic SCID-NOD mice were implanted with adult human liver cells treated with (.; n=9) or without (□; n=5) Ad-CMV-PDX-1 and growth factors under the kidney capsule. Glucose levels at the indicated days after transplantation are presented in mg %. Asterisks denote a significant difference (p<0.01) between the glucose levels of the Ad-CMV-PDX-1 treated implanted mice and the control cell implanted mice.
Figure 22B:
FIG. 22B are a series of photographs showing immuno-histochemistry staining for Pdx-1 (A) and insulin (B) in the kidney capsule sections, 10 days after implantation of Ad-CMV-PDX-1 treated adult liver cells. Insulin staining of the same SCID-NOD mouse pancreas (C).
Figure 22C:
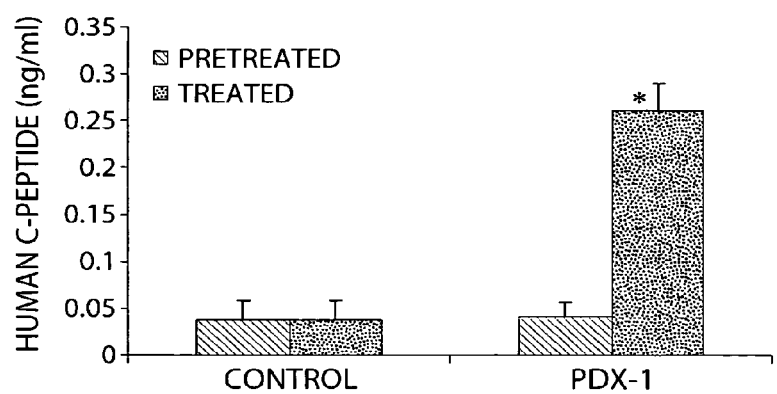
FIG. 22C is a bar chart showing Human C-peptide levels in serum of the implanted and control mice were measured by ELISA before the implantation experiment (0 days, pre-treated; grey bar) and at the end of the experiment (10 days, treated; black bar). Asterisks (*) denote a significant difference (p<0.01) between human C-peptide serum levels of Ad-CMV-PDX-1 treated cell implanted mice and the same diabetic mice prior to human cells implantation.
Figure 23:
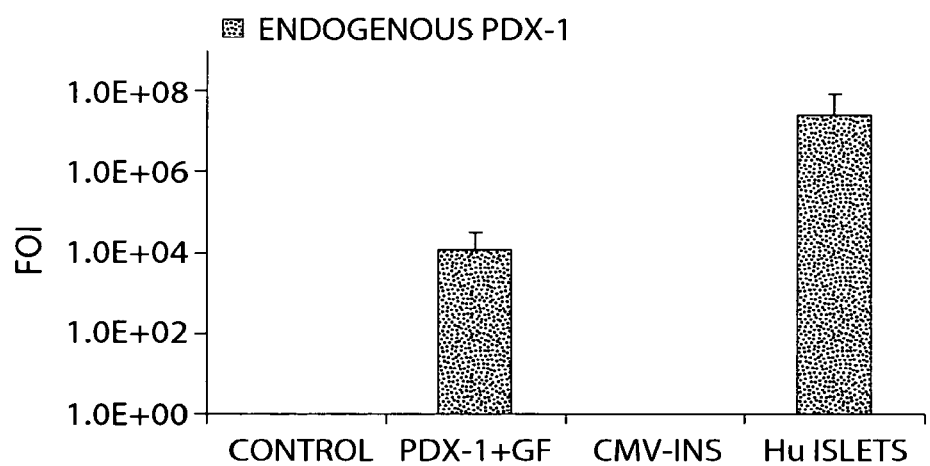
FIG. 23 is a bar chart showing ectopic expression of rat-PDX-1 induces the expression of the endogenous human PDX-1 in liver cells. Adult primary liver cells were treated by Ad-CMV-PDX-1 supplemented with growth factors and analyzed for endogenous human-PDX-1 gene expression. Results indicate fold of increase (FOI) compared to untreated control liver cells.

Transdifferentiated Adult Human Liver Cells Ameliorate Hyperglycemia in Diabetic Mice To determine the ability of transdifferentiated adult human liver cells to replace β-cell function, the cells were transplanted into immunodeficient, SCID-NOD mice, which were rendered diabetic by STZ treatment. FIG. 22 demonstrates that whereas control treated mice remained hyperglycemic, mice implanted by adult human liver cells treated by PDX-1, exhibited a gradual and significant decrease in blood glucose levels. Immunohistochemical analysis reveals that while these mice pancreata were empty of insulin, human liver cells implanted under the kidney capsule stained positive for PDX-1 and insulin (FIG. 18b). Human C-peptide could be detected in the serum of STZ-treated mice that were implanted by PDX-1 treated human liver cells. Human C-peptide levels were significantly 6-7-fold increased and averaged 0.26±0.03 ng/ml, compared to 0.04±0.02 ng/ml (P<0.01), in both normal SCID-NOD and the STZ-treated control mice (FIG. 22c). Serum mouse insulin levels in human cells implanted mice remained unchanged and were significantly lower (0.16±0.03 ng/ml) than in control normoglycemic SCID-NOD mice (0.45±0.03 ng/ml). Taken together; these findings indicate that the hyperglycemia in the implanted mice was normalized by human insulin that was secreted from the transdifferentiated human liver cells. These results establish the capacity of PDX-1 treated transdifferentiated adult human liver cells to function as surrogate β-cells in-vivo.

EXAMPLE 28

Figure 24A:
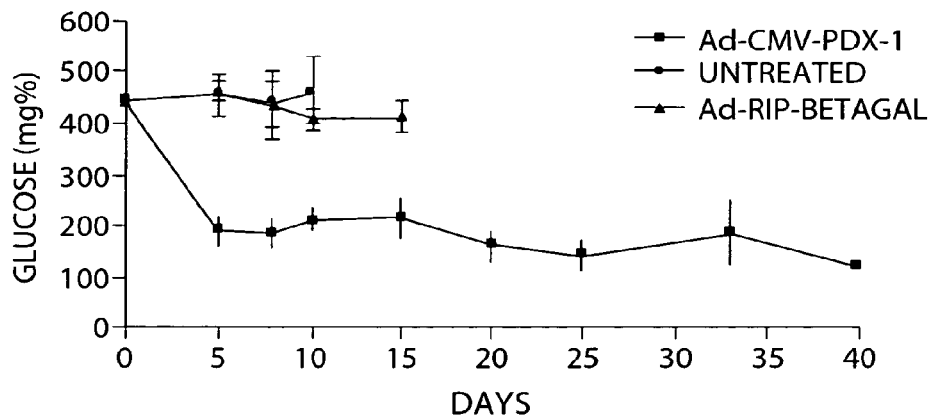
FIG. 24A is a chart depicting blood glucose levels in diabetic CAD-NOD mice treated with Ad-CMV-PDX-1. Control untreated or b-gal treated mice ▲, PDX-1 treated mice (.)
Figure 24B:
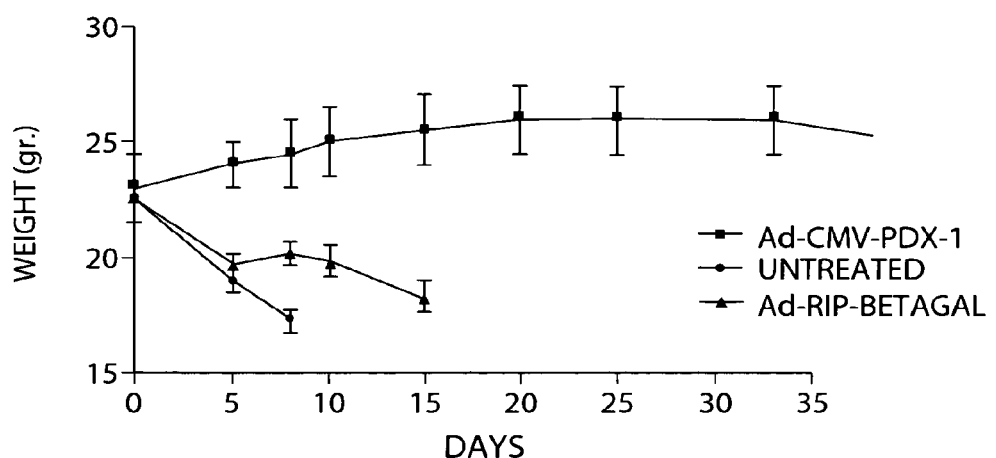
FIG. 24B is a bar chart depicting body weight diabetic CAD-NOD mice treated with Ad-CMV-PDX-1. Control untreated or b-gal treated mice ▲, PDX-1 treated mice (.)
Figure 24C:
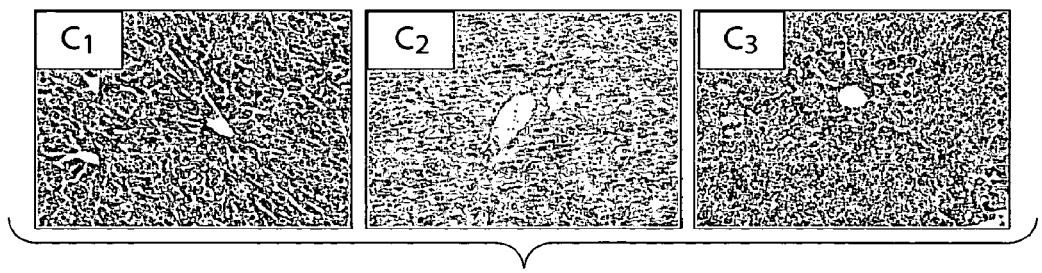
FIG. 24C is a series of photographs showing glycogen storage in Ad-CMV-PDX-1 treated diabetic mice. C1, treated mice; C2 non-treated mice; C3 pre-diabetic NOD mice.
Figure 25A:
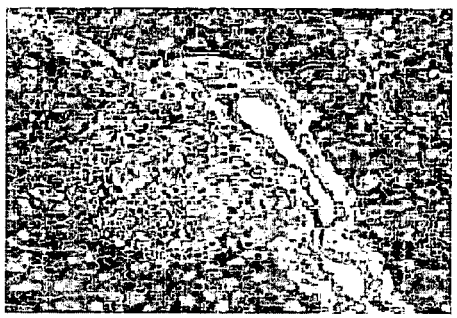
FIG. 25 are a series of photographs depicting immuno-histochemical staining of pancreas and liver in CAD-NOD mice. A, CAD-NOD mice negatively stained for insulin; B, control nondiabetic mice; C insulin in liver of PDX-1 treated mice; D, liver form non-treated diabetic mice.
Figure 25B:
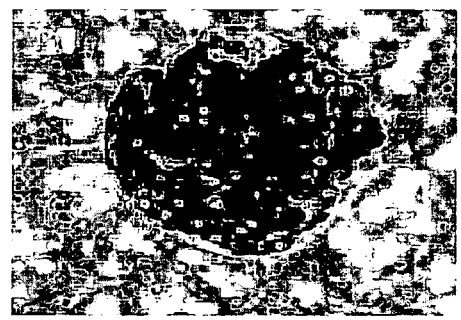
Figure 25C:
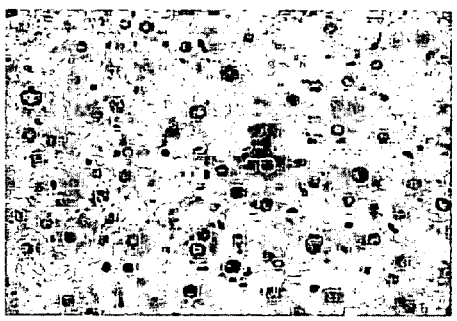
Figure 25D:

PDX-1 Induced Liver to Pancreas Transdifferentiation Reverts Hyperglycemia in CAD-NOD Mice To test the effect of PDX-1 induced liver-to-pancreas transdifferentiation on overt autoimmune diabetes, diabetic NOD mice were treated with Ad-CMV-PDX-1 or Ad-Rip-βGal as previously described. A group of mice was left untreated as a control. Blood glucose levels and body weight, to asses the regulation of glucose metabolism were monitored. Non-treated mice and mice treated with Ad-Rip-βGal remained hyperglycemic, lost weight, and died within the first two weeks following treatment (FIG. 24). In contrast, 65% (20 out of 34 mice) of the mice treated with Ad-CMV-PDX-1 became normoglycemic within the first 5 days following treatment. However, this normoglycemia was transient in some mice. While 38% of the mice treated with PDX1 (13/34) remained normoglycemic 1 month after treatment, the other 20% (7/34) treated with Ad-CMV-PDX-1 became hyperglycemic 10-14 days after treatment (FIG. 24a), while maintaining stable body weight for the whole duration of the experiment (FIG. 24b).

These data suggest that the process of liver to pancreas transdifferentiation induced by PDX-1 reverses autoimmune diabetes (e.g. Type 1).

EXAMPLE 29

Synthesis and Regulation of Insulin in Ad-CMV-Pdx-1-Treated Diabetic Mice

Figure 26A:
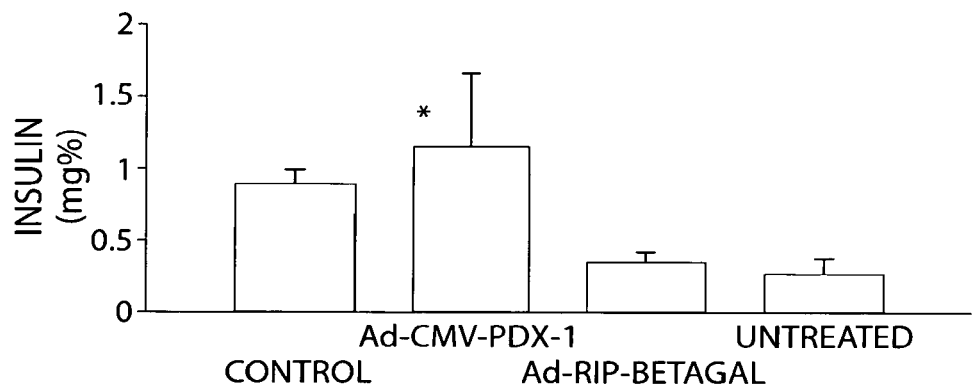
FIG. 26A is a bar chart depicting serum insulin levels of Ad-CMV-PDX-1 treated CAD-NOD mice.
Figure 26B:
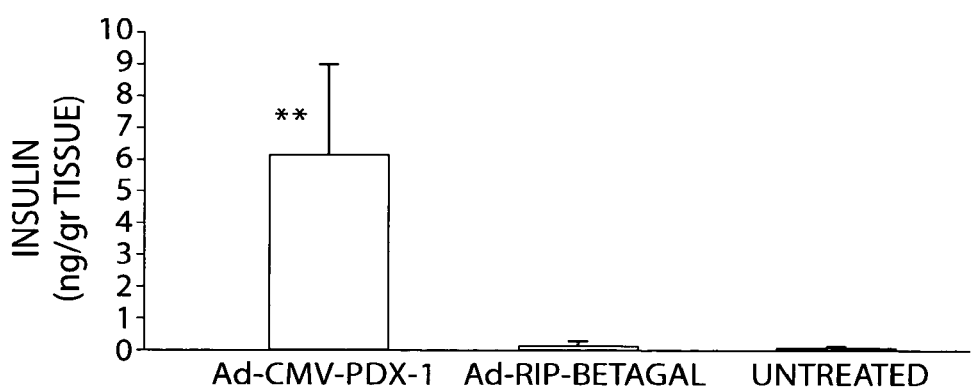
FIG. 26B is a bar chart depicting hepatic insulin levels of Ad-CMV-PDX-1 treated CAD-NOD mice.

Analysis by immunohistochemistry of pancreatic and hepatic insulin expression, revealed the presence of insulin-producing cells in the liver of mice treated with Ad-CMV-PDX-1, but not in their pancreas (FIG. 25). The hepatic insulin producing-cells were located close to central veins, as previously described. In addition, hepatic insulin content, and serum insulin levels were significantly higher in Ad-CMV-PDX-1-treated mice than in the control groups (FIG. 26). Thus, Ad-CMV-PDX-1 induced the expression of insulin in the liver and its secretion to the blood.

Figure 27:
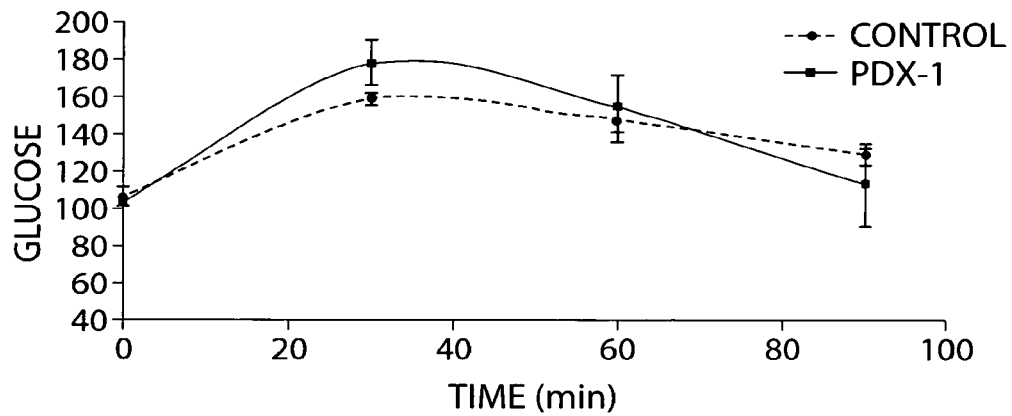
FIG. 27 is a graph depicting glucose tolerance of Ad-CMV-PDX-1 treated CAD-NOD mice.
Figure 28:
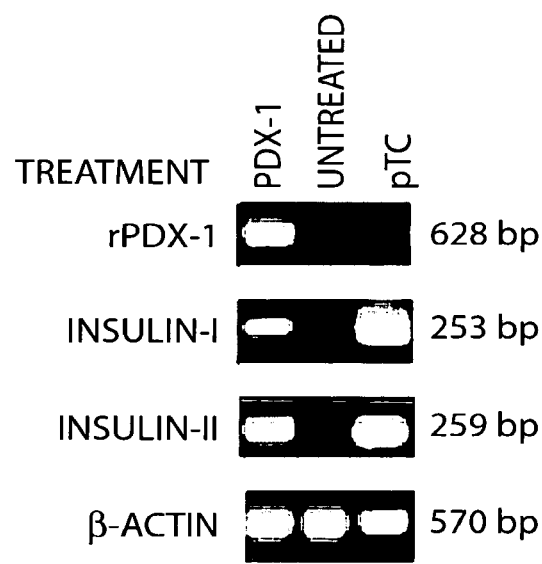
FIG. 28 is a photograph of RT-PCR and amplified products are resolved on agarose gel showing ectopic PDX-1 induced gene expression in CAD-NOD mouse livers.
Figure 29:
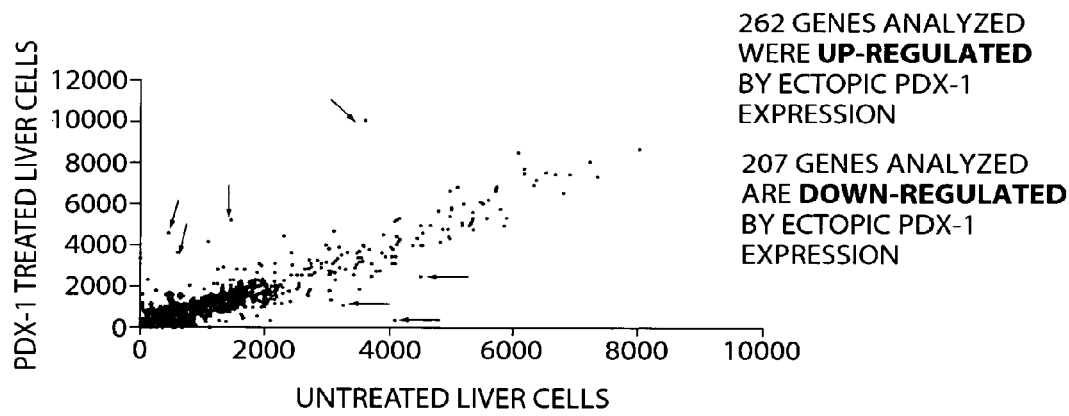
FIG. 29 is a scatter graph depicting PDX-1 induction of change of expression in about 500 genes, as analyzed by DNA microarray chip analysis of human liver cells treated by PDX-1 or by control.
Figure 31A:
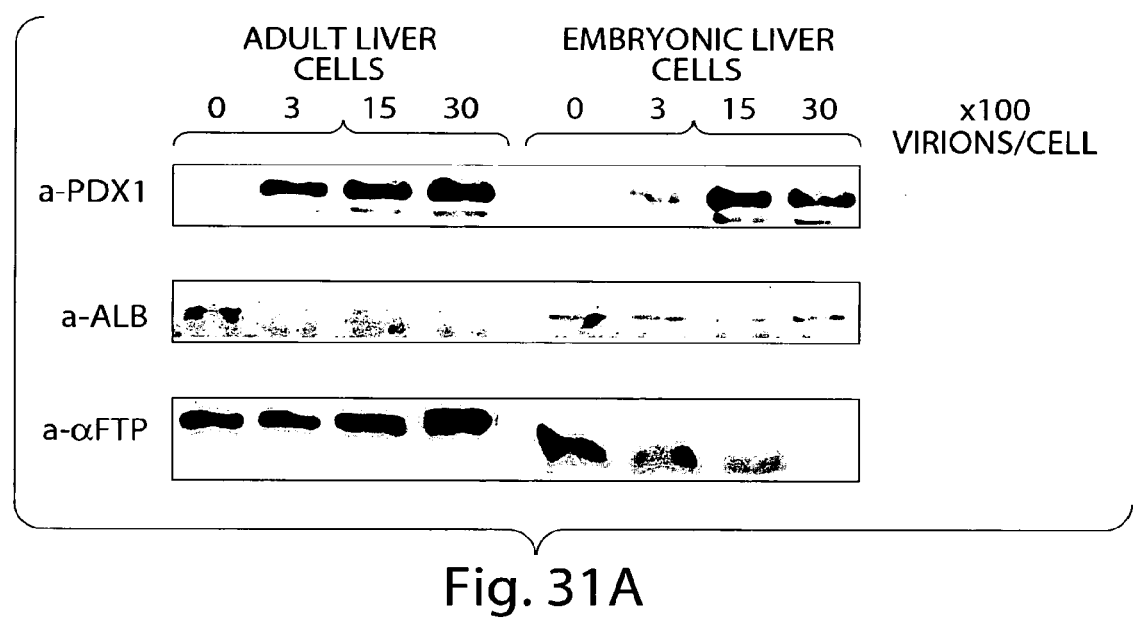
FIG. 31A is a photograph of a Western Blot showing PDX-1 repression of hepatic proteins, in mature (left) and Fetal (right) human hepatocytes, and the induction of dedifferentiation of adult human liver cells.
Figure 31B:
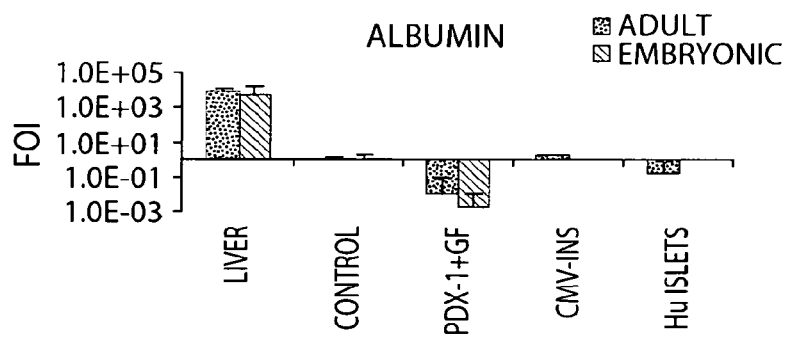
FIG. 31B is a bar chart showing PDX-1 repression of hepatic gene expression and protein production.
Figure 31C:
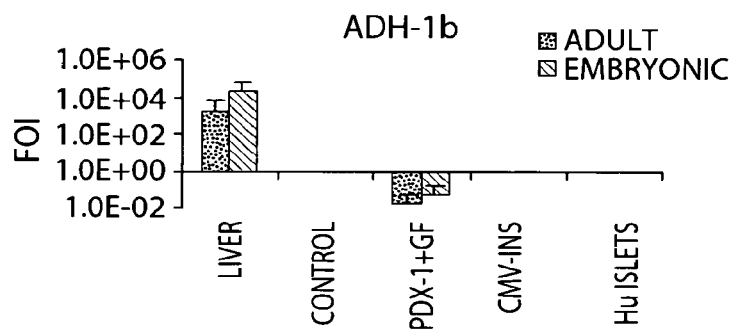
FIG. 31C is a bar chart showing PDX-1 repression of hepatic gene expression and protein production.
Figure 31D:
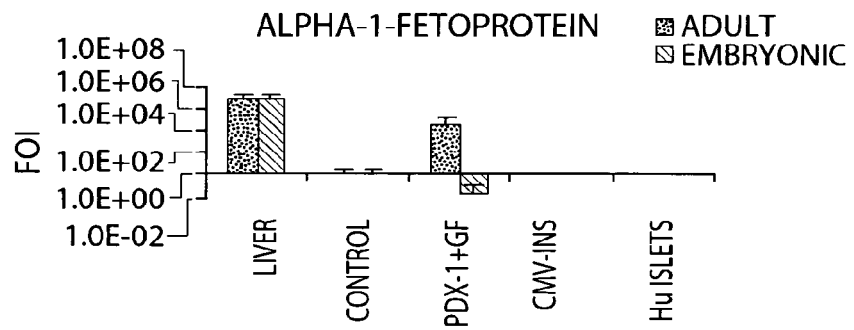
FIG. 31D is a bar chart showing PDX-1 induces dedifferation of mature liver cells as evident by the induction of embryonic markers.
Figure 31E:
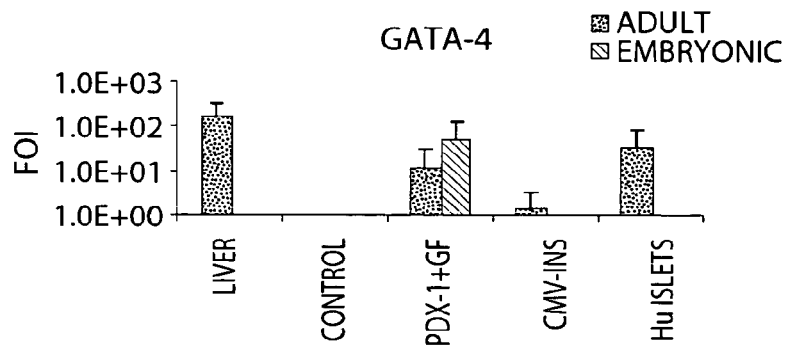
FIG. 31E is a bar chart showing PDX-1 induces dedifferation of mature liver cells as evident by the induction of embryonic markers.
Figure 32A:
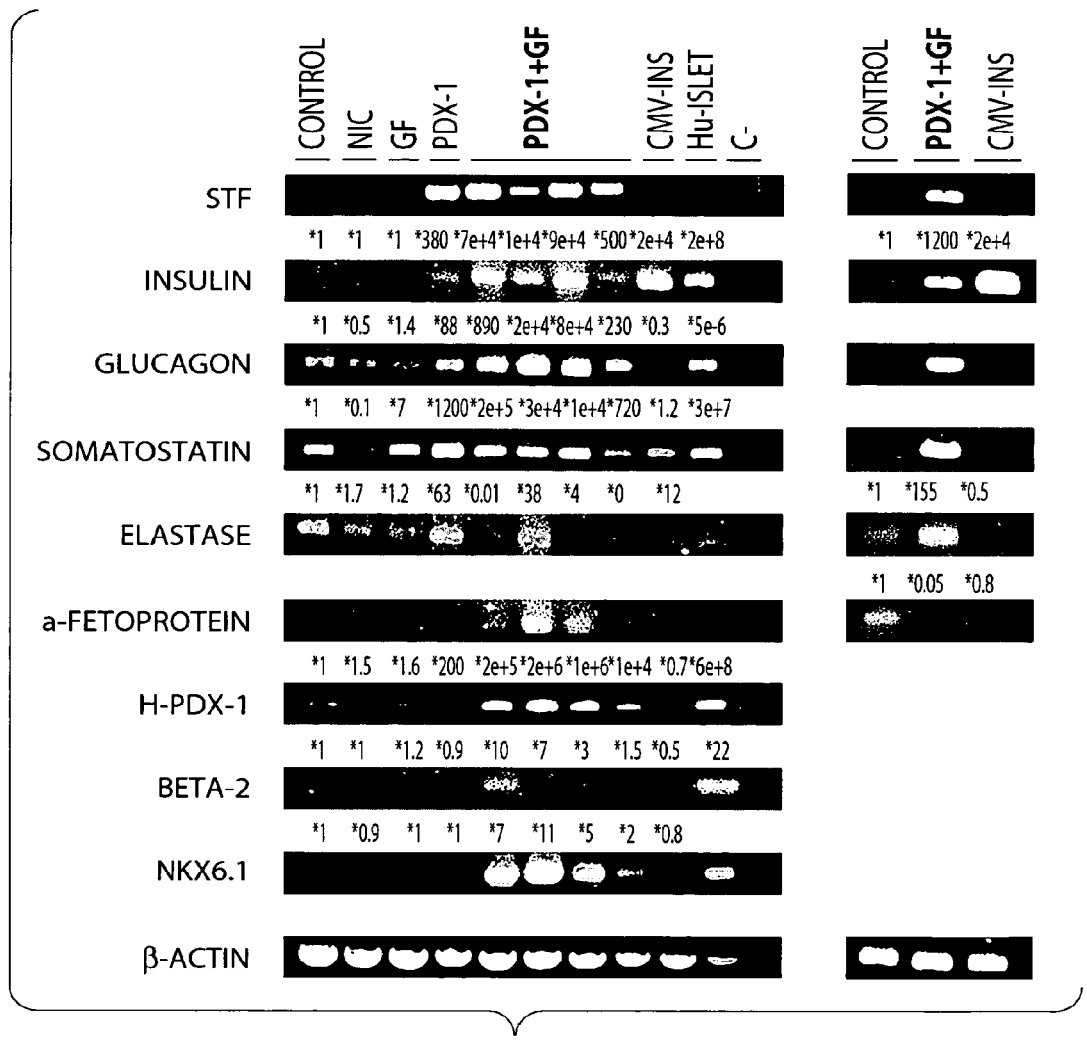
FIG. 32A is a photograph of a RT-PCR and amplified products are resolved on agarose gel showing ectopic PDX-1 induces pancreatic genes and pancreatic transcription factor expression in human liver cells in vitro.
Figure 32B:
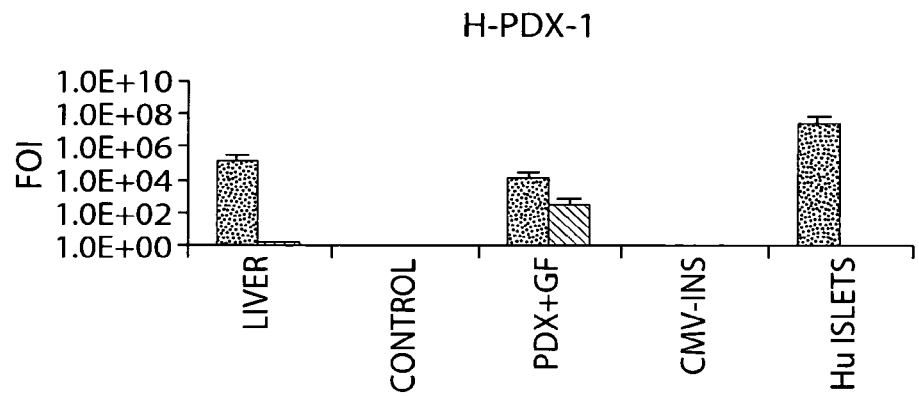
FIG. 32B is a bar chart showing ectopic PDX-1 induces endogenous, human PDX-1 expression in human liver cells in vitro.
Figure 32C:
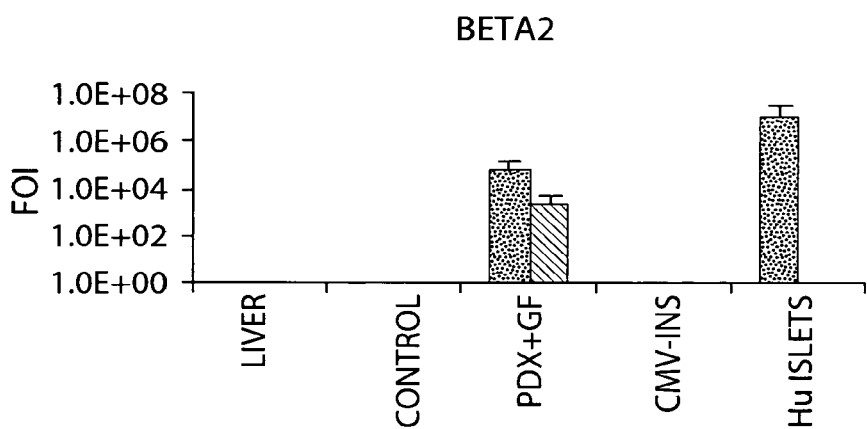
FIG. 32C is a bar chart showing ectopic PDX-1 induces beta2 expression in human liver) cells in vitro.
Figure 32D:
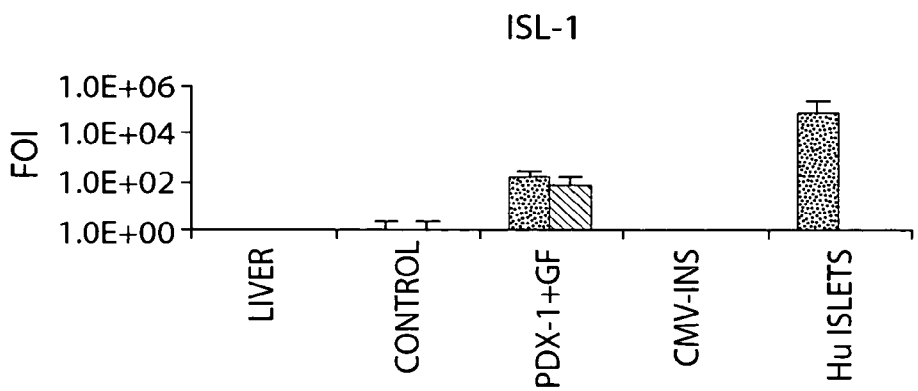
FIG. 32D is a bar chart showing ectopic PDX-1 induces Isl-1 expression in human liver cells in vitro.
Figure 32E:
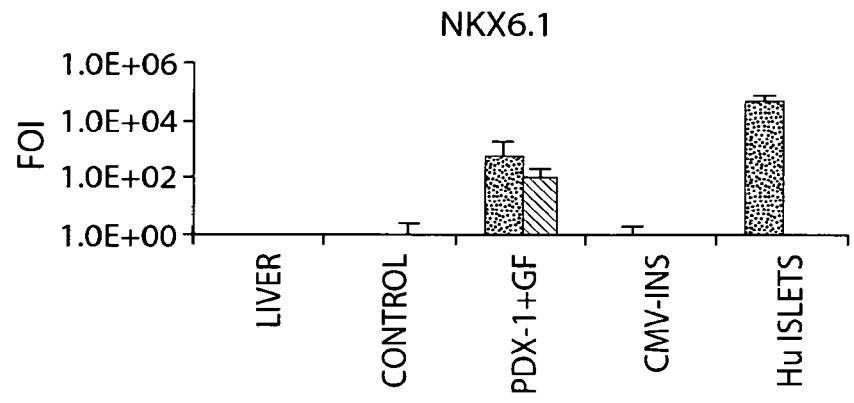
FIG. 32E is a bar chart showing ectopic PDX-1 induces Nkx6.1 expression in human liver cells in vitro.
Figure 32F:
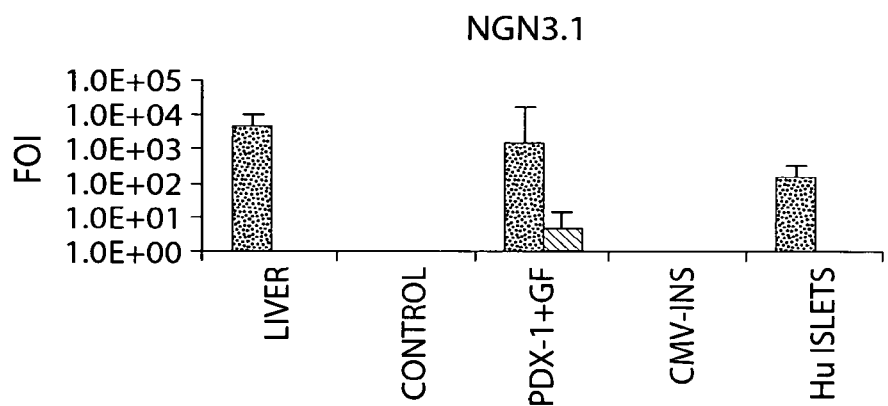
FIG. 32F is a bar chart showing ectopic PDX-1 induces Ngn3.1 expression in human liver cells in vitro.
Figure 32G:
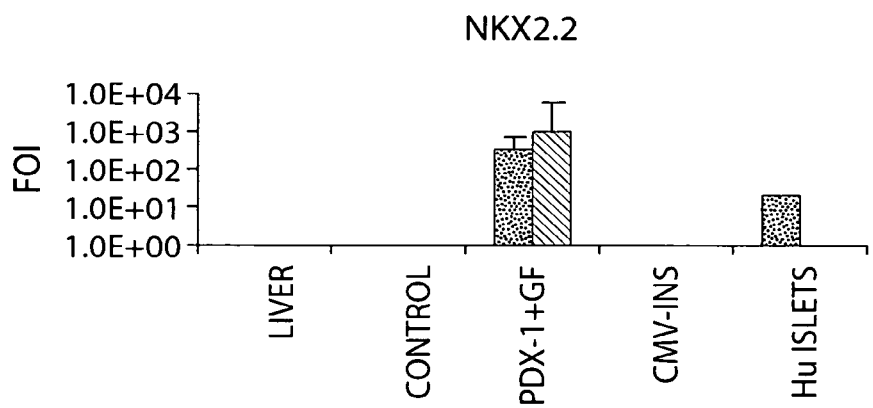
FIG. 32G is a bar chart showing ectopic PDX-1 induces Nkx2.2 expression in human liver cells in vitro.
Figure 33:
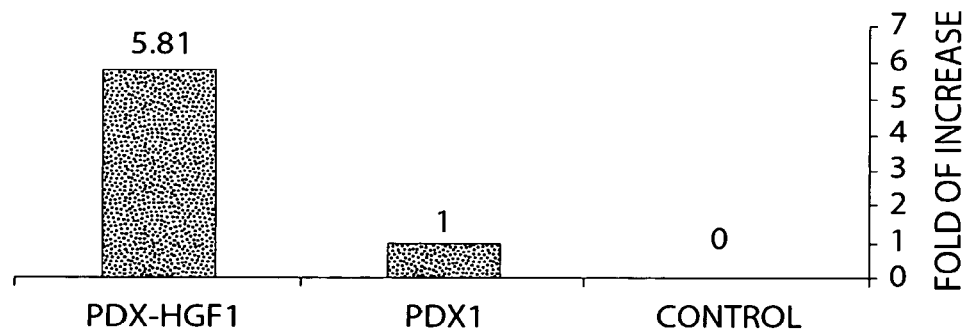
FIG. 33 is a bar chart showing ectopic PDX-1 induced insulin gene expression if augmented by hepatic growth factor-1.
Figure 34:
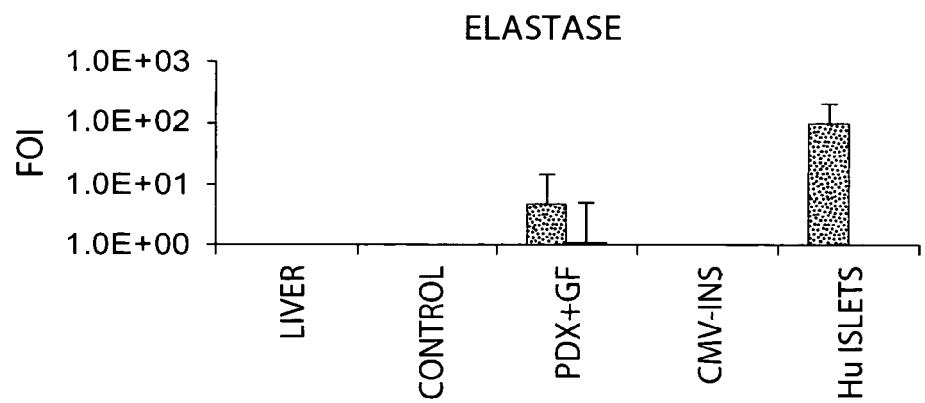
FIG. 34 is a bar chart showing ectopic PDX-1 induces elastase gene expression.
Figure 35:
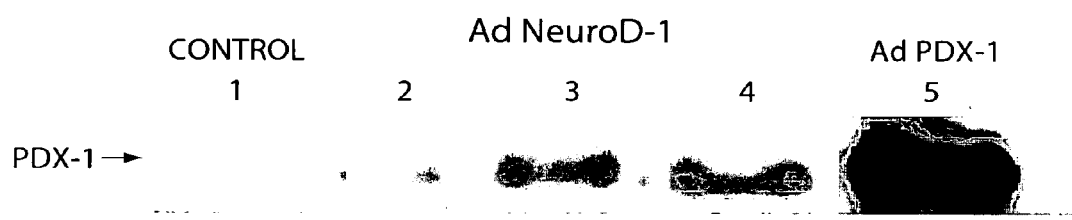
FIG. 35 is a Western blot analysis showing that ectopic NeuroD1 induces the endogenous Pdx-1 in liver cells.

To analyze the regulation of hepatic insulin release by blood glucose, glucose tolerance tests in 5 diabetic mice 2-3 weeks after they became normoglycemic following Ad-CMV-PDX-1 therapy were conducted. As controls, diabetic mice treated with Ad-CMV-βGal and healthy BALB/c mice were. No difference was seen in the rate of glucose clearance between healthy BALB/c and the Ad-CMV-PDX-1-treated mice, indicating that insulin secretion by liver transdifferentiated cells is indeed regulated by glucose (FIG. 27). In contrast, diabetic Ad-CMV-βGal-treated mice failed to show glucose clearance and remained hyperglycemic throughout the test. These data taken together indicate that PDX-1 induced functional liver to pancreas transdifferentiation occurs also in the mouse model of autoimmune. The PDX-1 induced normoglycemia was associated with the induction of insulin production in liver and its release in a glucose regulated manner.

EXAMPLE 30

PDX-1 Induced Developmental Shift of Bone Marrow Cells

To ability of ectopic PDX-1 to induce a developmental shift of bone marrow cells to functional pancreatic cells is determined as follows. AC133+ cells isolated from fresh and frozen human BM at purities greater than 90% are expanded in either (a) 24-well tissue culture plastic plates or (b) Teflon bags, in the continuous presence of IL-6, TPO, Flt-3 ligand, and SCF with or without TEPA for three weeks. The progenitor cell composition and potential are examined at the end of the treatment time and after long-term incubation in culture.

In order to optimize the infection and experimental conditions, the bifunctional adenovirus (AdRIP-GFP-CMV-PDX-1) is used to infect the cultures. Expression of the GFP-reporter gene as function of time after infection at $2-10^3$ MOI (number of viral particle divided by the number of cells in culture, MOI, multiplicity of infection). is followed The responding cells (that activate the insulin promoter and therefore express GFP) are sorted and cultured separately from non-responding cells for further analysis. A separated culture of control BM cells (either treated or untreated by TEPA) are treated by AdCMV-insulin as control for insulin production without transdifferentiation.

Gene expression is followed by RT-PCR. The levels of genes expression with time after the induction of the developmental shift, are analyzed by real time PCR using Real time PCR (ABI, USA) in a quantitative assay. The expression of pancreatic hormones, insulin, glucagon, somatostatin and prohormone convertases, and specific pancreatic transcription factors: BETA2, Isl-1, Nkx6.1, Pax4, and Pax6 and the endogenous PDX-1 are analyzed.

Hormones production is detected by immunohistochemistry using specific antibodies; guinea pig anti porcine-insulin; rabbit anti human-glucagon; rabbit anti human-somatostatin (all from DAKO A/S, Glostrup, Denmark). Production and secretion of insulin and glucagon is analyzed by commercially available RIA specific kits: Sensitive human insulin and C-peptide RIA kits and glucagon RIA kit, (Linco research ICN, Mo., USA). Glucose dose response and time course of pro/insulin synthesis and conversion to mature biological active insulin is resolved by reversed-phase HPLC as described (2), and by analyzing secretion of C-peptide into the culture medium using a specific human c-peptide RIA kit (Linco). The intracellular insulin content in the different glucose concentrations are analyzed.

The dynamics of the response of insulin secretion to glucose, in PDX-1 induced BM cells is analyzed in vitro and compared to that of ectopic insulin expression (AdCMV-hIns). Cells are incubated in different concentration of glucose in 6-well dishes, and a dose response and time course of IRI secretion to the medium will be measured by radioimmunoassay (RIA). Increased insulin secretion by forskolin/IBMX will indicate the induction of a regulated pathway for protein secretion in modulated liver cells. Sensitivity to glucose, but not to 2-DOG or L-glucose, indicates specific coupling of insulin secretion pathway to nutrient metabolism in the "modulated" liver cells Proliferation and transdifferentiated bone marrow cells capacity to control blood glucose levels and revert diabetes in diabetic SCID mice is analyzed to fully determine their capacity to mimic pancreatic b-cell function.

EXAMPLE 31

DNA Microarray Chip Analysis of Pdx-1 Treated Human Liver Cells

As shown in Figure DNA microarray analysis of PDX-1 treated human liver cells revealed over 500 genes that were either up-regulated if downregualted compared to control cells. Genes that were modulated in response to PDX-1 treatment includes pancreatic transcription factors (See, Table 5) and catalase and hepatic dismutase polypeptides (See, Table 6)

TABLE 5

Pancreatic Transcription Factors Induced in PDX-1 Treated Human Liver Cells

| | Liver | Pancreas | Cont | INS | PDX-1 | Panc/Liver | PDX/C |
|---|---|---|---|---|---|---|---|
| IPF1 | 1.8 | 7.1 | 2 | 1.3 | 3357 | 0.7 | 9.1 |
| PAX6 | 14.4 | 1761.7 | 6.4 | 6.5 | 6.9 | 7.3 | 0.4 |
| NKX2-2 | 12.5 | 836 | 1.6 | 0.7 | 1.4 | 6.5 | 0.1 |
| NEUROD1 | 13.7 | 634.9 | 8.3 | 12.7 | 3.3 | 5.4 | −1 |
| ISL1 | 3 | 595.1 | 3 | 10.1 | 11.1 | 6.4 | 2* |
| MEIS1 | 36.3 | 442.8 | 188.8 | 217.7 | 252.7 | 3.5 | 0.5 |
| MEIS2 | 73.6 | 396.4 | 120.9 | 147.8 | 116.1 | 2.4 | −0.2 |
| STAT1 | 240.3 | 255.5 | 637.7 | 1362.4 | 1458.9 | 0 | 1 |
| PBX3 | 78.2 | 201.7 | 133.7 | 170.5 | 182.7 | 1.4 | 0.3 |
| FOXA2 | 423.7 | 195 | 1.4 | 2.2 | 1.5 | −0.3 | 0.1 |
| PBX2 | 111.8 | 156.4 | 18.4 | 29.9 | 55.8 | 0.5 | 1 |
| GATA6 | 88.6 | 106.5 | 219.2 | 151.3 | 69.5 | 0 | −1 |
| FOXA1 | 88 | 50.3 | 20.3 | 9.8 | 19 | −1.1 | 0 |
| GATA4 | 48.6 | 37.8 | 86.4 | 95.8 | 59.3 | −0.9 | −0.4 |
| GLI2 | 16.3 | 33.1 | 45 | 51.4 | 67.3 | 0 | 0.5 |
| GLI3 | 52.5 | 16.4 | 80.5 | 94.3 | 98.8 | −1.7 | 0 |

*IS1-1 upregulated to the same levels by Ad-CMV-INS
Pancreatic genes upregulated by PDX-1 treatment are identified in Table 7.

TABLE 7

Pancreatic Genes Upregulated by PDX-1 treatment

| | | Liver | pancreas | ont | INS | PDX-1 | Panc/Liver | PDX/Cont |
|---|---|---|---|---|---|---|---|---|
| secretogranin II (chromogranin C) | SCG2 | 1.4 | 1735.3 | 0.9 | | 13 | 11.1 | 2.9 |
| transmembrane 4 superfamily member tetraspan NET-6 | NET-6 | 250.3 | 1429.7 | 4.8 | | 94. | 2.5 | 2.3 |
| regenerating islet-derived 1 alpha (pancreatic stone protein, pancreatic thread protein) | REG1A | 21.8 | 3857.5 | .9 | | 20. | 7.6 | 2.1 |
| secretagogin, EF-hand calcium binding protein | SCGN | 26.8 | 2080.8 | 0.1 | | 29. | 5.4 | 2.1 |
| secretory granule, neuroendocrine protein 1 (7B2 protein) | SGNE1 | 47.1 | 4793.1 | 10 | 1 | 376. | 6.3 | 1.8 |
| regulator of G-protein signalling 5 | RGS5 | 72.7 | 3585.3 | 2.8 | | 78. | 5.4 | 1.8 |
| tumor-associated calcium signal transducer 1 | TACSTD1 | 2.7 | 678.7 | .2 | | 11. | 9 | 1.7 |
| thrombospondin 4 | THBS4 | 11.4 | 629 | 5.6 | | 37. | 5.3 | 1.4 |
| p21 (CDKN1A)-activated kinase 3 | PAK3 | 48.8 | 742.3 | 2 | | 27. | 3.9 | 1.4 |
| protease, serine, 1 (trypsin 1) | PRSS1 | 28.1 | 2878.8 | .7 | | 3. | 7.2 | 1.3 |
| chromogranin A (parathyroid secretory protein 1) | CHGA | 25.6 | 4120.8 | 8.4 | | 36. | 5.6 | 1.1 |
| protocadherin 17 | PCDH17 | 83.5 | 768.3 | 1.1 | | 41. | 2.4 | 1.1 |
| serine protease inhibitor, Kazal type 1 | SPINK1 | 39.6 | 7719.1 | | | 6. | 6.3 | 1 |
| enolase 2, (gamma, neuronal) | ENO2 | 4.3 | 256.4 | 4.4 | 31 | 117.3 | 6 | 1.8 |
| protein tyrosine phosphatase, receptor type, N | PTPRN | 4.8 | 565.2 | 5.7 | 20.2 | 59.3 | 5.9 | 1.1 |
| amphiphysin (Stiff-Man syndrome with breast cancer 128 kDa autoantigen) | AMPH | 6.3 | 126.2 | .3 | 20.6 | 39.4 | 4.1 | 1.5 |
| neurobeachin | NBEA | 17.5 | 168.5 | 2.8 | 33.5 | 28.4 | 3.1 | 2.1 |
| protein kinase (cAMP-dependent, catalytic) inhibitor alpha | PKIA | 27 | 177.6 | 50.9 | 68.6 | 148.5 | 2.5 | 1.6 |
| chromosome 3 open reading frame 4 | C3orf4 | 32.3 | 131.8 | 93.1 | 152.7 | 240.1 | 2.3 | 1.2 |
| endothelin receptor type B | EDNRB | 37.1 | 280.3 | 94.4 | 101.9 | 593.8 | 2.3 | 2.6 |
| chromosome 1 open reading frame 9 | C1orf9 | 48.6 | 138.9 | 42.2 | 62.7 | 92.3 | 2.3 | 1.3 |
| synuclein, alpha (non A4 component of amyloid precursor) | SNCA | 33.5 | 146.6 | 21.2 | 34.4 | 110 | 2.3 | 2.3 |

TABLE 7-continued

Pancreatic Genes Upregulated by PDX-1 treatment

|  |  | Liver | pancreas | ont | INS | PDX-1 | Panc/Liver | PDX/Cont |
|---|---|---|---|---|---|---|---|---|
| regulator of G-protein signalling 2, 24 kDa | RGS2 | 87.4 | 553.4 | 58.6 | 122.8 | 335 | 2.3 | 2.2 |
| inhibin, beta A (activin A, activin AB alpha polypeptide) | INHBA | 49.3 | 13.6 | 174 | 470 | 1169 | −2 | 2.7 |

PDX-1 treatment in liver cultures down-regulated the expression of a variety of pancreatic genes. These pancreatic genes down-regulated by PDX-1 treatment are identified in Table 8.

TABLE 8

Pancreatic Genes Down-regulated by PDX-1 treatment

|  |  | liver | pancreas | cont | INS | PDX-1 | Panc/Liver | PDX/C |
|---|---|---|---|---|---|---|---|---|
| alcohol dehydrogenase 1B (class 1) | ADH1B | 1906.1 | 120.9 | 579.4 | 316.6 | 6.4 | −4.2 | −6.4 |
| G protein-coupled receptor 65 | GPR65 | 27 | 9.8 | 20.1 | 16.7 | 2.9 | −1.3 | −2.9 |
| D-aspartate oxidase | DDO | 56.1 | 8.9 | 27.2 | 18.3 | 2.8 | −2 | −2.7 |
| retinol dehydrogenase 5(11-cis and 9-cis) | RDH5 | 152.7 | 17.1 | 46.4 | 30.9 | 8.6 | −3.2 | −2.3 |
| retinoic acid receptor responder (tazarotene induced) | RARRES3 | 186 | 72.3 | 245.9 | 176.8 | 68.3 | −1.7 | −2.2 |
| Vascular cell adhesion molecule 1 | VCAM1 | 243.9 | 104.4 | 733.3 | 603.9 | 154.4 | −2.2 | −2.1 |
| Macrophage lectin 2 (calcium dependent) | HML2 | 74.2 | 18.9 | 19 | 15 | 2.9 | −2 | −1.8 |
| protein phosphatase 1, regulatory (inhibitor) subunit 3C | PPP1R3C | 639.8 | 180.6 | 1054.6 | 944 | 329.8 | −1.8 | −1.8 |
| sulfotransferase family, cytosolic, 1A, phenol-preferring, member 1 | SULT1A1 | 2415.8 | 381 | 673.8 | 386.7 | 177.8 | −2.5 | −1.7 |
| v-maf musculoaponeurotic fibrosarcoma oncogene homolog (avian) | MAF | 191.7 | 58.6 | 67.3 | 31.1 | 12.7 | −2 | −1.7 |
| biliverdin reductase B (flavin reductase (NADPH)) | BLVRB | 597.4 | 163.6 | 351.7 | 248.6 | 104.3 | −1.8 | −1.7 |
| Apolipoprotein L, 1 | APOL1 | 242 | 15.1 | 348.1 | 323.9 | 110.8 | −3.4 | −1.6 |
| p8 protein (candidate of metastasis | P8 | 584.2 | 195.2 | 1641.2 | 1322.3 | 425.5 | −1.5 | −1.5 |
| Phosphorylase, glycogen; liver | PYGL | 262.1 | 39.8 | 152.6 | 145.1 | 60.4 | −2.8 | −1.3 |
| Fc fragmen of IgG, receptor, transporter, alpha | FCGRT | 828.7 | 256 | 239.6 | 170.2 | 99.2 | −2.2 | −1.2 |
| Sulfotransferase family, cytosolic, 1A, phenol-preferring, member 3 | SULT1A3 | 855.5 | 342.3 | 272.5 | 215.2 | 128 | −1.5 | −1.2 |
| aldo-keto reductase family 1, member C3 (3-alpha hydroxysteroid dehydrogenase, type II) | AKR1C3 | 1308.5 | 96.2 | 246.6 | 202.4 | 132.2 | −3.6 | −1.1 |
| Sulfotransferase family, cytosolic, 1A, phenol-preferring, member 2; sulfotransferase family 1A, phenol-preferring, member 2 [Homo sapiens] | — | 940.8 | 199.3 | 259 | 212.2 | 130.9 | −2.1 | −1.1 |
| related RAS viral (r-ras) oncogene homolog 2 | RRAS2 | 228 | 67.1 | 451.5 | 415.2 | 183.6 | −2.1 | −1.1 |
| serine (or cysteine) proteinase inhibitor, clase F (alpha-2 anti-plasmin, pigment epithelium derived factor) | SERPINF1 | 2340.7 | 592.9 | 529.7 | 434.1 | 331.3 | −2.1 | −1 |
| retinoid X receptor, alpha | RXRA | 665.9 | 377.6 | 158.1 | 107.4 | 87.4 | −1.1 | −1 |
| Complement component 1, r subcomponent | C1R | 3610.9 | 290.3 | 1692 | 1407.8 | 971.9 | −3.8 | −1 |

TABLE 8-continued

| Pancreatic Genes Down-regulated by PDX-1 treatment | | | | | | | | |
|---|---|---|---|---|---|---|---|---|
| | | liver | pancreas | cont | INS | PDX-1 | Panc/Liver | PDX/C |
| calcium regulated heat stable protein 1, 24kDA | CARHSP1 | 612.5 | 54.1 | 275.3 | 203.4 | 151.6 | −2.6 | −1 |
| Follistin | FST | 135.4 | 38.4 | 98.5 | 117.5 | 51.6 | −1.7 | −1 |

The following abbreviations are used in the second column of Table 8: ADH1B=alcohol dehydrogenase 1B (class 1); GPR65=G protein-coupled receptor 65; DDO=D-aspartate oxidase; RDH5=retinol dehydrogenase 5 (11-cis and 9-cis); RARRES3=retinoic acid receptor responder (tazarotene induced) 3; VCAM=Vascular cell adhesion molecule 1; HML2=macrophage lectin 2 (calcium dependent); PPP1R3C=protein phosphatase 1, regulatory (inhibitor) subunit 3C; SULT1A1=sulfotransferase family, cytosolic, 1A, phenol-preferring, member 1; MAF=v-maf musculoaponeurotic fibrosarcoma oncogene homolog (avian); BLVRB=biliverdin reductase B (flavin reductase (NADPH)); APOL1=apolipoprotein L, 1; P8=p8 protein (candidate of metastasis 1); PYGL=phosphorylase, glycogen; liver; FCGRT=Fc fragment of IgG, receptor, transporter, alpha; SULT1A3=sulfotransferase family, cytosolic, 1A, phenol-preferring, member 3; AKR1C3=aldo-keto reductase family 1, member C3 (3-alpha hydroxysteroid dehydrogenase, type II); "sulfotransf-"=Sulfotransferase family, cytosolic, 1A, phenol-preferring, member 2; sulfotransferase family 1A, phenol-preferring, member 2 [*Homo sapiens*]; RRAS2=related RAS viral (r-ras) oncogene homolog 2; SERPINF1=serine (or cysteine) proteinase inhibitor, Glade F (alpha-2 antiplasmin, pigment epithelium derived factor); RXRA=retinoid X receptor, alpha; C1R=complement component 1, r subcomponent; CARHSP1=calcium regulated heat stable protein 1, 24 kDa; FST=follistatin.

EQUIVALENTS

From the foregoing detailed description of the specific embodiments of the invention, it should be apparent that unique methods of inducing pancreatic hormone production has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An in vitro method of increasing PDX-1 induction of a pancreatic islet cell phenotype or function in a population of human non-pancreatic primary cells, said method comprising the steps of:
   (1) contacting a population of human non-pancreatic primary cells with a composition comprising a nucleic acid encoding a PDX-1 polypeptide, wherein said PDX-1 is ectopically expressed within said cell population,
   (2) concurrently contacting said cell population with a composition comprising an effective amount of nicotinamide and epidermal growth factor; and
   (3) measuring the expression levels of PDX-1 in the contacted cells of step (2),
   wherein said concurrent contacting of said population with a composition comprising an effective amount of nicotinamide and epidermal growth factor increases PDX-1 induction of a pancreatic islet cell phenotype or function.

2. The method of claim 1, wherein said non-pancreatic cell population comprises a hepatic stem cell population.

3. The method of claim 1, wherein said non-pancreatic cell population comprises an adult cell population selected from the group consisting of a muscle cell population, a spleen cell population, a kidney cell population, a bone marrow cell population, a skin cell population, and a liver cell population.

4. The method of claim 1, wherein said increasing of PDX-1 induction of a pancreatic cell phenotype or function comprises at least two characteristics selected from the groups consisting of pancreatic islet specific gene expression, production of a pancreatic hormone, processing of a pancreatic hormone, storage of a pancreatic hormone and secretion of a pancreatic hormone.

5. The method of claim 4, wherein said pancreatic hormone is insulin, somatostatin, or glucagon, or any combination thereof.

6. The method of claim 4, wherein said islet cell gene expression profile in said population of human non-pancreatic primary cells comprises increased expression of PC1/3, insulin, glucagon or somatostatin, or any combination thereof, compared with expression in a control non-pancreatic cell population.

7. The method of claim 6, wherein said population of human non-pancreatic primary cells comprises sub-populations of cells, and wherein said islet cell gene expression of insulin, glucagon, or somatostatin, or any combination thereof, occurs in a same sub-population of cells.

8. The method of claim 6, wherein said population of human non-pancreatic primary cells comprises sub-populations of cells, and wherein said islet cell gene expression of insulin, glucagon, or somatostatin, or any combination thereof, occurs in different sub-populations of cells.

9. The method of claim 4, wherein insulin secretion is glucose-regulated.

\* \* \* \* \*

SEQUENCE LISTING

```
<160> NUMBER OF SEQ ID NOS: 47

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
tccaggtgcc tacaggattc tct                                               23

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
ccagtttgca ggctcgctgg                                                   20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
gctgcgtatg cacctcctgc                                                   20

<210> SEQ ID NO 4
```

```
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
ctttgtgaac caacacctgt gc                                             22

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
gcagatgctg gtacagcatt gt                                             22

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ttgccctctg ggagcccaaa                                                20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
cagatgctgg tgcagcactg                                                20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
tcttcctctg ggagtcccac                                                20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
cagatgctgg tgcagcactg                                                20

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
```
atggatgacg atatcgct                                                    18

<210> SEQ ID NO 11
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 11
atgaggtagt ctgtcaggt                                                   19

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 12
ctggttgtct ggacctctga gta                                              23

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 13
ccaacagcag aagtgagtgt gac                                              23

<210> SEQ ID NO 14
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 14
caagctcgct gggatcactg gagcag                                           26

<210> SEQ ID NO 15
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 15
gatgtgtctc tcggtcaagt tcaacatc                                         28

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
cctggctttg ggcggtgtca                                                  20

<210> SEQ ID NO 17
<211> LENGTH: 22
<212> TYPE: DNA

<213> ORGANISM: Artificial Sequence
<220> FEATURE:
<223> OTHER INFORMATION: synthetic oligonucleotide

<400> SEQUENCE: 17
ctcgggctcc agggcatcat tc                                             22

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18
accagcgact acagcaaata cctc                                           24

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 19
agcaatggcg acttcttctg g                                              21

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
gtgaccagct acaatcatag                                                20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
agttctccag ttggtagagg                                                20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
cgtaaagacc tctatgccaa                                                20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
agccatgcca aatgtgtcat                                                20

<210> SEQ ID NO 24
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 24
gatctgcccc ttgttaataa tctaatg                                27

<210> SEQ ID NO 25
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 25
gatccgccct taatgggcca aacggca                                27

<210> SEQ ID NO 26
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 26
atggatgacg atatcgct                                          18

<210> SEQ ID NO 27
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 27
atgaggtagt ctgtcaggt                                         19

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 28
ccaaaaccgt cgcatgaagt g                                      21

<210> SEQ ID NO 29
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 29
cagctcgcct ggtggctgt                                         19

<210> SEQ ID NO 30
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 30
ccttcgggcc ttagcgtgtc                                           20

<210> SEQ ID NO 31
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 31
cgcctgctgg tccgtattg                                            19

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
ttgccctctg ggagcccaaa                                           20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
cagatgctgg tgcagcactg                                           20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
tcttcctctg ggagtcccac                                           20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
cagatgctgg tgcagcactg                                           20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cagactccgt cagtttctgc                                           20

```
<210> SEQ ID NO 37
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 37
acaggatgtg aaagtcttcc a                                         21

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
atcattccca gcttcccaga                                           20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
cggttcctct tggtgttcat                                           20

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
ccacttgaga gctacacctg                                           20

<210> SEQ ID NO 41
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 41
ggattcccta tttggatcc                                            19

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
ctcaatggga gtttgttttg g                                         21

<210> SEQ ID NO 43
<211> LENGTH: 21
<212> TYPE: DNA
<213> ORGANISM: Artificial Sequence
<220> FEATURE:
<223> OTHER INFORMATION: synthetic oligonucleotide
```

```
-continued

<400> SEQUENCE: 43
gggggattag cactgaactc t                                              21

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
gggcacaaac agaccatcac                                                20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
gggatgggta agaaggtggt                                                20

<210> SEQ ID NO 46
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 46
gaaggttatc atctgccatc g                                              21

<210> SEQ ID NO 47
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 47
gggtggttcg ttctctatgt t                                              21
```